US012753138B2

(12) United States Patent
Browne et al.

(10) Patent No.: US 12,753,138 B2
(45) Date of Patent: Oct. 6, 2026

(54) AUTONOMOUS MODULAR FLARE GAS CONVERSION SYSTEMS AND METHODS

(71) Applicant: M2X Energy Inc., Rockledge, FL (US)

(72) Inventors: Joshua B. Browne, New York, NY (US); Bunmi Tolu Adekore, Somerville, MA (US); Paul E. Yelvington, Rockledge, FL (US); John Anthony Dean, Scotia, NY (US); Andrew Randolph, Salisbury, NC (US)

(73) Assignee: M2X Energy Inc., Rockledge, FL (US)

( * ) Notice: Subject to any disclaimer, the term of this patent is extended or adjusted under 35 U.S.C. 154(b) by 867 days.

(21) Appl. No.: 17/746,937

(22) Filed: May 17, 2022

(65) Prior Publication Data

US 2022/0388842 A1 Dec. 8, 2022

Related U.S. Application Data

(60) Provisional application No. 63/304,463, filed on Jan. 28, 2022, provisional application No. 63/213,129,
(Continued)

(51) Int. Cl.
*C07C 29/151* (2006.01)
*B01D 53/02* (2006.01)
(Continued)

(52) U.S. Cl.
CPC .......... *C07C 29/1518* (2013.01); *B01D 53/02* (2013.01); *B01D 53/229* (2013.01);
(Continued)

(58) Field of Classification Search
CPC ... C07C 29/1518; C07C 1/0485; B01D 53/02; B01D 53/229; B01D 2256/16;
(Continued)

(56) References Cited

U.S. PATENT DOCUMENTS

| | | | |
|---|---|---|---|
| 1,107,582 | A | 8/1914 | Brownlee |
| 2,362,151 | A | 11/1944 | Ostenberg |

(Continued)

FOREIGN PATENT DOCUMENTS

| | | |
|---|---|---|
| CN | 103216316 | 4/2015 |
| EP | 2028350 | 2/2009 |

(Continued)

OTHER PUBLICATIONS

Nov. 30, 2022, PCT, PCT/US2022/029707 Search and Opinion.
(Continued)

*Primary Examiner* — Anthony J Zimmer
*Assistant Examiner* — Syed T Iqbal
(74) *Attorney, Agent, or Firm* — Belvis Law, LLC.; Glen P. Belvis

(57) ABSTRACT

There are provided systems and methods for using fuel-rich partial oxidation to produce an end product from waste gases, such as flare gas. In an embodiment, the system and method use air-breathing piston engines and turbine engines for the fuel-rich partial oxidation of the flare gas to form synthesis gas, and reactors to convert the synthesis gas into the end product. In an embodiment the end product is methanol.

36 Claims, 26 Drawing Sheets

Related U.S. Application Data filed on Jun. 21, 2021, provisional application No. 63/197,898, filed on Jun. 7, 2021, provisional application No. 63/189,756, filed on May 18, 2021.

(51) Int. Cl.

| | |
|---|---|
| ***B01D 53/22*** | (2006.01) |
| ***B01J 12/00*** | (2006.01) |
| ***B01J 19/00*** | (2006.01) |
| ***C01B 3/02*** | (2006.01) |
| ***C01B 3/025*** | (2026.01) |
| ***C01B 3/36*** | (2006.01) |
| ***C01C 1/04*** | (2006.01) |
| ***C07C 1/04*** | (2006.01) |
| ***C10L 3/08*** | (2006.01) |
| ***F02C 3/30*** | (2006.01) |

(52) U.S. Cl.

CPC ........... *B01J 12/005* (2013.01); *B01J 19/004* (2013.01); *C01B 3/025* (2013.01); *C01B 3/36* (2013.01); *C01B 3/366* (2013.01); *C01C 1/0488* (2013.01); *C07C 1/0485* (2013.01); *C10L 3/08* (2013.01); *F02C 3/30* (2013.01); *B01D 2256/16* (2013.01); *B01J 2219/00182* (2013.01); *B01J 2219/00186* (2013.01); *C01B 2203/025* (2013.01); *C01B 2203/061* (2013.01); *C01B 2203/062* (2013.01); *C01B 2203/068* (2013.01); *C01B 2203/1241* (2013.01); *C01B 2203/1614* (2013.01); *C01B 2203/1628* (2013.01); *C01B 2203/82* (2013.01); *C10L 2200/0461* (2013.01); *C10L 2290/02* (2013.01); *C10L 2290/145* (2013.01); *F05D 2220/75* (2013.01)

(58) Field of Classification Search

CPC .................... B01J 12/005; B01J 19/004; B01J 2219/00182; B01J 2219/00186; C01B 3/025; C01B 3/36; C01B 3/366; C01B 2203/025; C01B 2203/061; C01B 2203/062; C01B 2203/068; C01B 2203/1241; C01B 2203/1614; C01B 2203/1628; C01B 2203/82; C01B 2203/04; C01B 2203/0405; C01B 2203/043; C01B 2203/06; C01B 2203/1258; C01B 2203/16; C01C 1/0488; C10L 3/08; C10L 2200/0461; C10L 2290/02; C10L 2290/145; F02C 3/30; F05D 2220/75

See application file for complete search history.

(56) References Cited

U.S. PATENT DOCUMENTS

| | | | | |
|---|---|---|---|---|
| 2,543,791 | A | 3/1951 | Malin | |
| 2,591,687 | A | 4/1952 | Eastman | |
| 2,846,297 | A | 8/1958 | Herwig | |
| 4,965,052 | A | 10/1990 | Lowther | |
| 6,174,460 | B1 | 1/2001 | Grunvald | |
| 7,040,270 | B2 | 5/2006 | Din | |
| 7,367,183 | B2 | 5/2008 | Eberspach | |
| 8,366,796 | B2 | 2/2013 | Mitchell | |
| 8,413,617 | B2 | 4/2013 | Simpson | |
| 8,574,501 | B1 | 11/2013 | Greer | |
| 8,677,949 | B2 | 3/2014 | Bromberg | |
| 8,793,981 | B2 | 8/2014 | Li | |
| 8,795,597 | B2 | 8/2014 | Conrad | |
| 8,857,405 | B2 | 10/2014 | Attard | |
| 8,858,900 | B2 | 10/2014 | Galloway | |
| 8,882,863 | B2 | 11/2014 | Modroukas | |
| 8,901,179 | B2 | 12/2014 | Raffaele | |
| 9,051,237 | B2 | 6/2015 | Peter | |
| 9,151,212 | B2 | 10/2015 | Dumser | |
| 9,169,773 | B2 * | 10/2015 | Bromberg | F02B 65/00 |
| 9,316,144 | B2 | 4/2016 | Gruber | |
| 9,353,674 | B2 | 5/2016 | Bunce | |
| 9,637,433 | B2 | 5/2017 | Zubrin | |
| 9,643,906 | B2 | 5/2017 | Zubrin | |
| 9,725,386 | B2 | 8/2017 | Zubrin | |
| 9,771,919 | B2 | 9/2017 | Kim | |
| 9,856,197 | B2 | 1/2018 | Zubrin | |
| 9,909,491 | B2 | 3/2018 | Bromberg | |
| 9,957,888 | B2 | 5/2018 | Lissianski | |
| 10,125,726 | B2 | 11/2018 | Henry | |
| 10,144,877 | B2 | 12/2018 | Ravikumar | |
| 10,161,296 | B2 | 12/2018 | Schock | |
| 10,184,374 | B2 | 1/2019 | Han | |
| 10,233,808 | B2 | 3/2019 | Backhaus | |
| 10,233,871 | B2 | 3/2019 | Hill | |
| 10,260,460 | B2 | 4/2019 | Singh | |
| 10,465,631 | B2 | 11/2019 | Lissianski | |
| 10,513,435 | B2 | 12/2019 | Edalati | |
| 10,654,023 | B2 | 5/2020 | Jahnke | |
| 10,669,220 | B2 | 6/2020 | Balthasar | |
| 10,787,959 | B2 | 9/2020 | Roychoudhury | |
| 10,815,123 | B2 | 10/2020 | Northrop | |
| 10,815,912 | B2 | 10/2020 | Bhosekar | |
| 10,865,709 | B2 | 12/2020 | Hwang | |
| 10,890,120 | B2 | 1/2021 | Hehle | |
| 10,907,559 | B2 | 2/2021 | Asai | |
| 10,947,934 | B2 | 3/2021 | Asai | |
| 11,131,277 | B2 | 9/2021 | Asai | |
| 11,168,045 | B2 | 11/2021 | Moreo | |
| 11,192,843 | B2 | 12/2021 | Badgandi | |
| 11,292,717 | B2 | 4/2022 | Vicari | |
| 11,649,201 | B2 | 5/2023 | Yelvington | |
| 11,649,777 | B2 | 5/2023 | Carpenter | |
| 11,845,712 | B2 | 12/2023 | Ridley | |
| 11,851,393 | B2 | 12/2023 | Early | |
| 12,264,122 | B2 | 4/2025 | Ridley | |
| 12,304,816 | B2 | 5/2025 | Barnett | |
| 2002/0131907 | A1 | 9/2002 | Iwasaki | |
| 2003/0119919 | A1 * | 6/2003 | Allam | F25J 3/04539 518/704 |
| 2005/0217178 | A1 | 10/2005 | Aoyama | |
| 2010/0126135 | A1 | 5/2010 | Digamber | |
| 2010/0175379 | A1 | 7/2010 | Liu | |
| 2010/0275891 | A1 | 11/2010 | Gruber | |
| 2012/0088850 | A1 * | 4/2012 | Rabovitser | C10G 2/30 208/46 |
| 2012/0103302 | A1 | 5/2012 | Attard | |
| 2013/0160734 | A1 | 6/2013 | Redtenbacher | |
| 2014/0373531 | A1 | 12/2014 | Wong | |
| 2015/0126628 | A1 | 5/2015 | Patience | |
| 2015/0300296 | A1 | 10/2015 | Mulye | |
| 2016/0053668 | A1 | 2/2016 | Loetz | |
| 2016/0152537 | A1 | 6/2016 | Zubrin et al. | |
| 2017/0174599 | A1 * | 6/2017 | Zubrin | C07C 41/01 |
| 2018/0086683 | A1 | 3/2018 | Sapienza | |
| 2019/0337876 | A1 | 11/2019 | Short | |
| 2020/0222874 | A1 | 7/2020 | Manenti | |
| 2021/0130272 | A1 | 5/2021 | Lepri | |
| 2022/0388842 | A1 | 12/2022 | Browne | |
| 2022/0401906 | A1 | 12/2022 | Dean | |
| 2022/0403272 | A1 | 12/2022 | Dean | |
| 2023/0064109 | A1 | 3/2023 | Lourenco | |
| 2023/0116003 | A1 | 4/2023 | Feinstein | |
| 2023/0212098 | A1 | 7/2023 | Yelvington | |
| 2023/0257330 | A1 | 8/2023 | Breidenstein | |
| 2023/0279802 | A1 | 9/2023 | Merical | |
| 2023/0286807 | A1 | 9/2023 | Yelvington | |
| 2023/0340919 | A1 | 10/2023 | Mercal | |
| 2024/0017235 | A1 | 1/2024 | Yelvington | |
| 2024/0017993 | A1 | 1/2024 | Dean | |
| 2024/0051824 | A1 | 2/2024 | Paravathikar | |

(56) References Cited

U.S. PATENT DOCUMENTS

| | | | |
|---|---|---|---|
| 2024/0124377 | A1 | 4/2024 | Yelvington |
| 2025/0042829 | A1 | 2/2025 | Muscionico |

FOREIGN PATENT DOCUMENTS

| | | |
|---|---|---|
| EP | 2998538 | 3/2016 |
| EP | 3037646 | 5/2016 |
| EP | 2606211 | 11/2022 |
| WO | WO 2015/138987 | 9/2015 |
| WO | WO 2024040124 | 2/2024 |
| WO | WO 2025022348 | 1/2025 |
| WO | WO 2025141340 | 7/2025 |

OTHER PUBLICATIONS

Nov. 4, 2022, PCT, PCT/US2022/029708 Search and Opinion.
Apr. 2016, Lim, et al, The Engine Reformer: Syngas Production in an Engine for Compact Gas-to-Liquids Synthesis; vol. 94, p. 623 (Canadian Journal of Chem Eng).
Feb. 2019, Medhat, et al, Frontiers in combustion techniques and burner designs for emissions control and CO2 capture: A review; Int J Energy Res 2019;1-.
Apr. 2015, Pederstad, et al, Improving utilization of assoicated gas in US tight oil fields (Carbon Limits AS).
(Down loaded) 2022, Nissan, VC-Turbo Engine (https://www.nissan-global.com/EN/INNOVATION/TECHNOLOGY/ARCHIVE/VC_TURBO_ENGINE/).
Apr. 2016, Emmauel, The Engine Reformer: Syngas Production in an Engine for Compact Gas-to-Liquids Synthesis.
Jun. 23, 2023, Third Party, Third Party submission in U.S. Appl. No. 17/746,927 (claims charts).
Jun. 23, 2023, Third Party, Third Party submission in U.S. Appl. No. 17/746,927 (List of References).
Jun. 2015, Lim THe Engine Reformer: Syngas Production in Engines Using Spark-Ignition and Metallic Foam Catalysts (pp. title-50).
Third Party submission in U.S. Appl. No. 17/746,927 (pp. 51-75).
Third Party submission in U.S. Appl. No. 17/746,927 (pp. 76-100).
Third Party submission in U.S. Appl. No. 17/746,927 (pp. 101-130).
Third Party submission in U.S. Appl. No. 17/746,927 (pp. 131-162).
Oct. 1, 1986. Chao, Thermodynamic Properties of Key Organic Oxygen Compounds in the Carbon Range C, to C, Part 2. Ideal Gas Properties.
1998, Chase, Journal of Physical and Chemical Reference Data Monograph No. 9 NIST-JANAF Thermochemical Tables Fourth Edition Part ,I Al—Co.
Jan. 2021, Methanol Institute, Innovation Outlook Renewable Methanol.
Mar. 2020, IEA, Reducing the environmental impact of oil and gas supply is a pivotal element of global energy transitions.
Jan. 20, 2016, Lim, The Engine Reformer: Syngas Production in an Engine for Compact Gas-to-Liquids Synthesis.
1956, Ing, Production of synthesis gas in the gasoline engine with simultaneous gain in work (Google Translation.
1956, Ing, Herstellung von Synthesegas im Otto-Motor beigleichzeitigerArbeitsgewinnung.
Jun. 25, 1963, Yamamoto, Production of Synthesis Gas by an Internal Combustion Engine.
1983, Picken, A Method for Estimating Overhaul Life of Internal Operating on Biogas and Methane.
Karim, Examination of Rich Mixture Operation of a Dual Fuel Engine.
Karim, The Production of Hydrogen by the Partial Oxidtion of Methane in a Dual Fuel Engine.
2001, Ogden, Examination of Rich Mixture Operation of a Dual Fuel Engine.
Oct. 6, 2005, McMillian, Experimental and modelng study of hydrogen/syngas production and particulate emissions from a.
2008, Karim, The production of hydrogen through the uncatalyzed partial oxidation of methane in an internal.
2014, Morsy, Modeling study on the production of hydrogen/syngas via partial oxidation using a homogeneous charge compression ignition engine fueled with.
2016, Lim, The Engline Reformer: Syngas Productlon in an Engine for Compact Gas-to-Liquids Synthesis.
Mar. 16, 2018, Tartakovsky, Fuel reforming in internal combustion engines.
Jan. 25, 2019, Banke, Power and syngas productlon from partial oxidation of fuel-rich methane/DME mixtures in an HCCI engine.
Apr. 2, 2019, Voice, Fuel and Engine Effects on Rich-Combustion Products as an Enabler of In-Cylinder Reforming.
Aug. 30, 2020, Atakan, Flexible energy conversion an storage via high-temperature gas-phase reactions: The piston engine as a polygeneration.
Apr. 14, 2020, Wang, Extend Syngas Yield through Increasing Rich Limit by Stratified Air Injection in a Single Cylinder Engine.
2020, Paykani, Synthesis gas as a fuel for internal combustion engines in transportation.
Jul. 14, 2005, Yelvington, On piston engines as hydrocarbon gas reformers for modular, distributed chemical production.
Browne, Economic analysis non-catalytic, partial-oxidation methane reformer using an internal combustion.
Idicheria, An Advanced Ignition System for High Efficiency Engines.
Karim (believed to be), Photo copy of book pages (54-72).
2017, L'Heureux, Repurposing mass-produced internal combustion engines Quantifying the value and use of low-cost internal.
2025, Shin, CFD modeling of non-catalytic, partial-oxidation engine reformer for flare mitigation.
South West Research Institute (SwRI), Diesel Cylinder Head Design up to 250 Bar Peak Cylinder Pressure.

* cited by examiner

| Equipment | Shaft (kW) Power |
|---|---|
| Inlet Air Compressor | 92.4 |
| Syngas Compressor | 961.3 |
| Recycle Compressor | 2.0 |
| **Total Compressor Power, Gross** | **1055.7** |
| Turbo-Expander | -292.5 |
| **Total Compressor Power, Net** | **763.2** |

| Engine Backpressure (Bar) | PR, Stage | PR, Total | Syngas Compressor (kW) | Compressors, Total (kW) | % Change |
|---|---|---|---|---|---|
| 2 | 2.924 | 25.0 | 1231.2 | 1325.6 | – |
| 3 | 2.554 | 16.7 | 961.3 | 1055.7 | -20.4% |
| 4 | 2.321 | 12.5 | 860.3 | 954.6 | -28.0% |

(Typical Ranges of Wobbe Number vs Fuel Heating Value)

Global Warming Potential (GWP) Values Relative to $CO_2$

| Industrial Designation or Common Name | Chemical Formula | GWP Values for 100-Year Time Horzon | | |
|---|---|---|---|---|
| | | Second Assessment Report (SAR) | Fourth Assessment Report (AR4) | Fifth Assessment Report (AR5) |
| **Carbon Dioxide** | $CO_2$ | 1 | 1 | 1 |
| **Methane** | $CH_4$ | 21 | 25 | 28 |
| **Nitrous Oxide** | $N_2O$ | 310 | 298 | 265 |

FIG. 22

AUTONOMOUS MODULAR FLARE GAS CONVERSION SYSTEMS AND METHODS

This application: (i) claims under 35 U.S.C. § 119(e)(1) the benefit of the filing date of, and claims the benefit of priority to, U.S. provisional application Ser. No. 63/189,756 filed May 18, 2021; (ii) claims under 35 U.S.C. § 119(e)(1) the benefit of the filing date of, and claims the benefit of priority to, U.S. provisional application Ser. No. 63/213,129 filed Jun. 21, 2021; (iii) claims under 35 U.S.C. § 119(e)(1) the benefit of the filing date of, and claims the benefit of priority to, U.S. provisional application Ser. No. 63/197,898 filed Jun. 7, 2021; and (iv) claims under 35 U.S.C. § 119(e)(1) the benefit of the filing date of, and claims the benefit of priority to, U.S. provisional application Ser. No. 63/304,463 filed Jan. 28, 2022, the entire disclosure of each of which are incorporated herein by reference.

BACKGROUND OF THE INVENTION

Field of the Invention

The present inventions relate to new and improved methods, devices and systems for recovering and converting waste gases, such as flare gas, into useful and economically viable materials.

The term "flare gas" and similar such terms should be given their broadest possible meaning, and would include gas generated, created, associated or produced by, or from, oil and gas production, hydrocarbon wells (including shall, conventional and unconventional wells), petrochemical processing, refining, landfills, waste water treatment, dairies, livestock production, and other municipal, chemical and industrial processes. Thus, for example, flare gas would include stranded gas, associated gas, landfill gas, vented gas, biogas, digester gas, small-pocket gas, and remote gas.

Typically, the composition of flare gas is a mixture of different gases. The composition can depend upon the source of the flare gas. For instance, gases released during oil-gas production mainly contain natural gas. Natural gas is more than 90% methane ($CH_4$) with ethane and smaller amounts of other hydrocarbons, water, $N_2$ and $CO_2$ may also be present. Flare gas from refineries and other chemical or manufacturing operations typically can be a mixture of hydrocarbons and in some cases $H_2$. Landfill gas, biogas or digester gas typically can be a mixture of $CH_4$ and $CO_2$, as well as small amounts of other inert gases. In general, flare gas can contain one or more of the following gases: methane, ethane, propane, n-butane, isobutane, n-pentane, isopentane, n-hexane, ethylene, propylene, 1-butene, carbon monoxide, carbon dioxide, hydrogen sulfide, hydrogen, oxygen, nitrogen, and water.

The majority of flare gas is produced from smaller, individual point sources, such as a number of oil or gas wells in an oil field, a landfill, or a chemical plant. Prior to the present inventions flare gas, and in particular flare gas generated from hydrocarbon producing wells, and other smaller point sources, was burned to destroy it, in some instances may have been vented directly into the atmosphere. This flare gas could not be economically recovered and used. The burning or venting of fare gas, both from hydrocarbon production and other endeavors, raises serious concerns about pollution and the production greenhouse gases.

As used herein unless specified otherwise, the terms "syngas" and "synthesis gas" and similar such terms should be given their broadest possible meaning and would include gases having as their primary components a mixture of $H_2$ and CO; and may also contain $CO_2$, $N_2$, and water, as well as, small amounts of other materials.

As used herein unless specified otherwise, the term "product gas" and similar such terms should be given their broadest possible meaning and would include gasses having $H_2$, CO and other hydrocarbons, and typically significant amounts of other hydrocarbons, such as methane.

As used herein unless specified otherwise, the term "reprocessed gas" includes "syngas", "synthesis gas" and "product gas".

As used herein unless specified otherwise, the terms "partial oxidation", "partially oxidizing" and similar such terms mean a chemical reaction where a sub-stoichiometric mixture of fuel and air (i.e., fuel rich mixture) is partially reacted (e.g., combusted) to produce a syngas. The term partial oxidation includes both thermal partial oxidation (TPOX), which typically occurs in a non-catalytic reformer, and catalytic partial oxidation (CPOX). The general formula for a partial oxidation reaction is $$C_nH_m + \frac{n}{2}O_2 \longrightarrow nCO + \frac{m}{2}H_2$$

As used herein unless specified otherwise, the term "$CO_2e$" is used to define carbon dioxide equivalence of other, more potent greenhouse gases, to carbon dioxide (e.g., methane and nitrous oxide) on a global warming potential basis of 100 years, based on Intergovernmental Panel on Climate Change (IPCC) Fifth Assessment Report (AR5) methodology. The term "carbon intensity" is taken to mean the lifecycle $CO_2e$ generated per unit mass of a product.

As used herein, unless specified otherwise, the terms % and mol % are used interchangeably and refer to the moles of a first component as a percentage of the moles of the total, e.g., formulation, mixture, material or product.

As used herein unless specified otherwise, the recitation of ranges of values herein is merely intended to serve as a shorthand method of referring individually to each separate value falling within the range. Unless otherwise indicated herein, each individual value within a range is incorporated into the specification as if it were individually recited herein.

Generally, the term "about" as used herein unless stated otherwise is meant to encompass the greater of a variance or range of ±10% or the experimental or instrument error associated with obtaining the stated value.

As used herein, unless stated otherwise, room temperature is 25° C., and standard temperature and pressure is 15° C. and 1 atmosphere (1.01325 bar).

Unless specifically provided otherwise, all entropy values, including entropy states, entropy points, specific entropy points, and specific entropy values, that are discussed in the specification and shown in the Figures, in particular the T-S diagrams, are based upon, or use as a reference state absolute zero (i.e., 0° K, −273.15° C.) and 1 atmosphere.

Related Art and Terminology

In the production of natural resources from formations within the earth a well or borehole is drilled into the earth to the location where the natural resource is believed to be located. These natural resources may be a hydrocarbon reservoir, containing natural gas, crude oil and combinations of these; the natural resource may be fresh water; it may be a heat source for geothermal energy; or it may be some other natural resource that is located within the ground.

These resource-containing formations may be a few hundred feet, a few thousand feet, or tens of thousands of feet below the surface of the earth, including under the floor of a body of water, e.g., below the sea floor. In addition to being at various depths within the earth, these formations may cover areas of differing sizes, shapes and volumes.

Typically, and by way of general illustration, in drilling a well an initial borehole is made into the earth, e.g., the surface of land or seabed, and then subsequent and smaller diameter boreholes are drilled to extend the overall depth of the borehole. In this manner as the overall borehole gets deeper its diameter becomes smaller; resulting in what can be envisioned as a telescoping assembly of holes with the largest diameter hole being at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 30" conductor may or may not be cemented into place. During this drilling operation a riser is generally not used and the cuttings from the borehole, e.g., the earth and other material removed from the borehole by the drilling activity are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A BOP (blow out preventer) is then secured to a riser and lowered by the riser to the sea floor; where the BOP is secured to the wellhead. From this point forward all drilling activity in the borehole takes place through the riser and the BOP.

It should be noted that riserless subsea drilling operations are also contemplated.

For a land-based drill process, the steps are similar, although the large diameter tubulars, 30"-20" are typically not used. Thus, and generally, there is a surface casing that is typically about 13⅜" diameter. This may extend from the surface, e.g., wellhead and blow out preventer (BOP), to depths of tens of feet to hundreds of feet. One of the purposes of the surface casing is to meet environmental concerns in protecting ground water. The surface casing should have sufficiently large diameter to allow the drill string, product equipment such as an electronic submersible pump (ESP) and circulation mud to pass through. Below the casing one or more different diameter intermediate casings may be used. (It is understood that sections of a borehole may not be cased, which sections are referred to as open hole.) These can have diameters in the range of about 9" to about 7", although larger and smaller sizes may be used, and can extend to depths of thousands and tens of thousands of feet. Inside of the casing and extending from a pay zone, or production zone of the borehole up to and through the wellhead on the surface is the production tubing. There may be a single production tubing or multiple production tubings in a single borehole, with each of the production tubing endings being at different depths.

Fluid communication between the formation and the well can be greatly increased by the use of hydraulic fracturing techniques. The first uses of hydraulic fracturing date back to the late 1940s and early 1950s. In general, hydraulic fracturing treatments involve forcing fluids down the well and into the formation, where the fluids enter the formation and crack, e.g., force the layers of rock to break apart or fracture. These fractures create channels or flow paths that may have cross sections of a few micron's, to a few millimeters, to several millimeters in size, and potentially larger. The fractures may also extend out from the well in all directions for a few feet, several feet and tens of feet or further. It should be remembered that the longitudinal axis of the well in the reservoir may not be vertical: it may be on an angle (either slopping up or down) or it may be horizontal. For example, in the recovery of shale gas and oil the wells are typically essentially horizontal in the reservoir. The section of the well located within the reservoir, i.e., the section of the formation containing the natural resources, can be called the pay zone.

As used herein, unless specified otherwise, the terms “hydrocarbon exploration and production”, “exploration and production activities”, “E&P”, and “E&P activities”, and similar such terms are to be given their broadest possible meaning, and include surveying, geological analysis, well planning, reservoir planning, reservoir management, drilling a well, workover and completion activities, hydrocarbon production, flowing of hydrocarbons from a well, collection of hydrocarbons, secondary and tertiary recovery from a well, the management of flowing hydrocarbons from a well, and any other upstream activities.

As used herein, unless specified otherwise, the term “earth” should be given its broadest possible meaning, and includes, the ground, all natural materials, such as rocks, and artificial materials, such as concrete, that are or may be found in the ground.

As used herein, unless specified otherwise “offshore” and “offshore drilling activities” and similar such terms are used in their broadest sense and would include drilling activities on, or in, any body of water, whether fresh or salt water, whether manmade or naturally occurring, such as for example rivers, lakes, canals, inland seas, oceans, seas, such as the North Sea, bays and gulfs, such as the Gulf of Mexico. As used herein, unless specified otherwise the term “offshore drilling rig” is to be given its broadest possible meaning and would include fixed towers, tenders, platforms, barges, jack-ups, floating platforms, drill ships, dynamically positioned drill ships, semi-submersibles and dynamically positioned semi-submersibles. As used herein, unless specified otherwise the term “seafloor” is to be given its broadest possible meaning and would include any surface of the earth that lies under, or is at the bottom of, any body of water, whether fresh or salt water, whether manmade or naturally occurring.

As used herein, unless specified otherwise, the term “borehole” should be given it broadest possible meaning and includes any opening that is created in the earth that is substantially longer than it is wide, such as a well, a well bore, a well hole, a micro hole, a slimhole and other terms commonly used or known in the arts to define these types of narrow long passages. Wells would further include exploratory, production, abandoned, reentered, reworked, and injection wells. They would include both cased and uncased wells, and sections of those wells. Uncased wells, or section of wells, also are called open holes, or open hole sections.

Boreholes may further have segments or sections that have different orientations, they may have straight sections and arcuate sections and combinations thereof. Thus, as used herein unless expressly provided otherwise, the "bottom" of a borehole, the "bottom surface" of the borehole and similar terms refer to the end of the borehole, i.e., that portion of the borehole furthest along the path of the borehole from the borehole's opening, the surface of the earth, or the borehole's beginning. The terms "side" and "wall" of a borehole should to be given their broadest possible meaning and include the longitudinal surfaces of the borehole, whether or not casing or a liner is present, as such, these terms would include the sides of an open borehole or the sides of the casing that has been positioned within a borehole. Boreholes may be made up of a single passage, multiple passages, connected passages, (e.g., branched configuration, fishboned configuration, or comb configuration), and combinations and variations thereof.

Boreholes are generally formed and advanced by using mechanical drilling equipment having a rotating drilling tool, e.g., a bit. For example, and in general, when creating a borehole in the earth, a drilling bit is extending to and into the earth and rotated to create a hole in the earth. To perform the drilling operation the bit must be forced against the material to be removed with a sufficient force to exceed the shear strength, compressive strength or combinations thereof, of that material. The material that is cut from the earth is generally known as cuttings, e.g., waste, which may be chips of rock, dust, rock fibers and other types of materials and structures that may be created by the bit's interactions with the earth. These cuttings are typically removed from the borehole by the use of fluids, which fluids can be liquids, foams or gases, or other materials know to the art.

As used herein, unless specified otherwise, the term "drill pipe" is to be given its broadest possible meaning and includes all forms of pipe used for drilling activities; and refers to a single section or piece of pipe. As used herein the terms "stand of drill pipe," "drill pipe stand," "stand of pipe," "stand" and similar type terms should be given their broadest possible meaning and include two, three or four sections of drill pipe that have been connected, e.g., joined together, typically by joints having threaded connections. As used herein the terms "drill string," "string," "string of drill pipe," string of pipe" and similar type terms should be given their broadest definition and would include a stand or stands joined together for the purpose of being employed in a borehole. Thus, a drill string could include many stands and many hundreds of sections of drill pipe.

As used herein, unless specified otherwise, the terms "formation," "reservoir," "pay zone," and similar terms, are to be given their broadest possible meanings and would include all locations, areas, and geological features within the earth that contain, may contain, or are believed to contain, hydrocarbons.

As used herein, unless specified otherwise, the terms "field," "oil field" and similar terms, are to be given their broadest possible meanings, and would include any area of land, sea floor, or water that is loosely or directly associated with a formation, and more particularly with a resource containing formation, thus, a field may have one or more exploratory and producing wells associated with it, a field may have one or more governmental body or private resource leases associated with it, and one or more field(s) may be directly associated with a resource containing formation.

As used herein, unless specified otherwise, the terms "conventional gas", "conventional oil", "conventional", "conventional production" and similar such terms are to be given their broadest possible meaning and include hydrocarbons, e.g., gas and oil, that are trapped in structures in the earth. Generally, in these conventional formations the hydrocarbons have migrated in permeable, or semi-permeable formations to a trap, or area where they are accumulated. Typically, in conventional formations a non-porous layer is above, or encompassing the area of accumulated hydrocarbons, in essence trapping the hydrocarbon accumulation. Conventional reservoirs have been historically the sources of the vast majority of hydrocarbons produced. As used herein, unless specified otherwise, the terms "unconventional gas", "unconventional oil", "unconventional", "unconventional production" and similar such terms are to be given their broadest possible meaning and includes hydrocarbons that are held in impermeable rock, and which have not migrated to traps or areas of accumulation.

Global Warming and Environmental Concerns

The relative harm to the environment by the release of waste gases when compared to $CO_2$ an established highly problematic gas, are shown FIG. 22.

The environmental impact in terms of global warming potential of methane slippage from flare gas and venting cannot be overstated. According to a 2019 International Energy Agency (IEA) report, about 200 billion cubic meter (bcm) of waste or flair gas were combusted or vented into the atmosphere in 2018. About 50 bcm of gas were vented, and about 150 bcm were combusted in flares. Combustion is intended to convert hydrocarbons to $CO_2$, but their peak efficiency is 98%, and that efficiency drops in the presence of wind. The combination of inefficient combustion and venting results in total $CO_2e$ emissions of about 1.4 gigatons of $CO_2$, which amounts to about 2.7% of all anthropogenic sources of $CO_2$ per year.

This Background of the Invention section is intended to introduce various aspects of the art, which may be associated with embodiments of the present inventions. Thus, the forgoing discussion in this section provides a framework for better understanding the present inventions, and is not to be viewed as an admission of prior art

SUMMARY

There has been a long-standing, expanding and unmet need, for systems, devices and methods to convert otherwise uneconomic hydrocarbon-based fuel, e.g., flare gas, to value-added, easily transported products (such as methanol, ethanol, mixed alcohols, ammonia, dimethyl-ether, F-T liquids, and other fuels or chemicals). The present inventions, among other things, solve these needs by providing the articles of manufacture, devices, systems and processes taught, and disclosed herein.

Thus, there is provided a system for converting flare gas into an end product, the system having: a reformer stage and a synthesis stage; the reformer stage comprising: an intake for receiving a flow of a flare gas; an intake for receiving a flow of air; a mixer for combining the flow of air and the flow of the flare gas; wherein the mixer is configured to provide a mixture having a rich fuel/air equivalence ratio; an air breathing reformer, configured to operate under rich fuel/air conditions; wherein the reformer is configured to operate in a partial oxidation combustion window; whereby the reformer is configured to convert the mixture into a syngas; a line for flowing the syngas to the synthesis stage; the synthesis stage having: a line for receiving a flow of syngas from the reformer stage; a synthesis unit configured to receive the syngas and convert the syngas into an end product; a control system configured to operate the reformer stage at a predetermined partial oxidation temperature and a predetermined partial oxidation pressure; and the synthesis stage at a predetermined synthesis temperature and a predetermined synthesis pressure.

In addition, there is provided a system for converting a flare gas to an end product, the system having: a flare gas source, defining a starting specific entropy; an oxygen source, wherein the oxygen source comprises air; a fuel/air mixture defining a starting specific entropy; a control system; an air-breathing reformer; the reform in conjunction with the control system, configured to partially oxidize a mixture of the oxygen source and the flare gas; thereby providing a reprocessed gas flow comprises a syngas; a synthesis unit in conjunction with the control system configured to provide a first product stream comprising an end product; wherein the end product stream and an exhaust product stream define a final specific entropy; the control system configured to operate the system wherein the starting specific entropy and the final specific entropy are less than about 1 kJ/kg° C. of each other; and, wherein during operation the system is configured to produces less than 2.0 kg of $CO_2$ per kg of flare gas received.

Further, there is provided a continuous method of converting a flare gas to methanol, the method including: receiving a flare gas flow from a source, wherein: the flare gas flow has a rate of about 50,000 scfd to about 30,000,000 scfd; the flare gas flow has a composition, wherein the composition varies over time; compressing the flare gas flow to provide a compressed flare gas flow, wherein the compressed flare gas flow has a pressure of about 8 bar to about 60 bar; mixing the compressed flare gas flow with air to provide a rich fuel/air mixture; partially oxidizing the rich fuel/air mixture at a temperature of from about 700° C. to about 1,200° C. in a reformer to provide a reprocessed gas flow; wherein the reprocessed gas flow having a syngas having a syngas composition; passing the reprocessed gas flow through a deoxygenation reactor, whereby any excess oxygen is removed from the reprocessed gas flow, thereby providing a deoxygenated reprocessed gas flow; removing water from the deoxygenated reprocessed gas flow to thereby provided a syngas flow; controlling the pressure and the temperature of the syngas flow to provide a predetermined synthesis temperature and synthesis pressure of the syngas flow; flowing the syngas flow at the predetermined synthesis temperature and synthesis pressure into a synthesis unit; converting the syngas flow in the synthesis unit to thereby provide a first product stream having methanol; and, removing a material from the first product stream, the material having hydrogen; to thereby provide a second product stream; wherein the second product stream having at least about 80% methanol, and is thereby at least about 80% pure.

Yet further, there is provided a continuous method of converting a flare gas to methanol, the method including: receiving a flare gas flow from a source, wherein the flare gas flow has a rate of flow; receiving an air flow from an intake; mixing the flare gas flow with air flow to provide a fuel/air mixture; wherein the fuel/air mixture defines a starting specific entropy; flowing the fuel/air mixture, having a pressure of about 8 bar to 60 bar, into a reformer, partially oxidizing the rich fuel/air mixture at a temperature of from about 700° C. to about 1,200° C. in the reformer to provide a reprocessed gas flow; wherein the reprocessed gas flow having a syngas having a syngas composition; controlling the pressure and the temperature of the reprocessed gas flow to provide a predetermined synthesis temperature and a predetermined synthesis pressure of the syngas flow; converting the reprocessed gas flow in the synthesis unit at the predetermined synthesis temperature and synthesis pressure in a synthesis unit to thereby provide a first product stream having methanol; wherein the first product stream and an exhaust product stream thereby defining a final specific entropy; and, wherein the starting specific entropy and the final specific entropy are less than about 1 kJ/kg° C. of each other.

Additionally, there is provided a system for converting a flare gas to an end product, the system having: a flare gas source, defining a starting specific entropy; an air source; a fuel/air mixture defining a starting specific entropy; a control system; an air-breathing reformer; the reform in conjunction with the control system, configured to partially oxidize a mixture of the air and the flare gas; thereby providing a reprocessed gas flow comprises a syngas; a synthesis unit in conjunction with the control system configured to provide a first product stream comprising an end product; wherein the end product stream and an exhaust product stream define a final specific entropy; the control system configured to operate the system wherein the starting specific entropy and the final specific entropy are less than about 1 kJ/kg° C. of each other; and, wherein during operation, the system is configured to be net carbon-negative, whereby during operation the system produces less than about −20 kg CO2e per kg of end product provided.

Still in addition, there is provided a system for converting a flare gas to an end product, the system having: a flare gas source, defining a starting specific entropy; an air source, a fuel/air mixture defining a starting specific entropy; a control system; an air-breathing reformer; the reform in conjunction with the control system, configured to partially oxidize a mixture of the air and the flare gas; thereby providing a reprocessed gas flow comprises a syngas; a synthesis unit in conjunction with the control system configured to provide a first product stream comprising an end product; wherein the end product stream and an exhaust product stream define a final specific entropy; the control system configured to operate the system wherein the starting specific entropy and the final specific entropy are less than about 1 kJ/kg° C. of each other; wherein during operation, the system is configured to be net carbon-negative, whereby during operation the system produces less than about −20 kg CO2e per kg of end product provided; and, wherein during operation the system is configured to produces less than 2.0 kg of $CO_2$ per kg of flare gas received.

In addition, there is provided a method of converting a flare gas to an end product, the method including: receiving a flare gas from a source; forming a mixture of the flare gas and an oxygen source, wherein the oxygen source having air, thereby defining a fuel/air mixture; wherein the fuel/air mixture defines a starting specific entropy; partially oxidizing the fuel/air mixture at a predetermined reformer temperature; thereby providing a reprocessed gas flow having a syngas having a syngas composition; converting the reprocessed gas flow in a synthesis unit to thereby provide a first product stream having an end product; wherein the first product stream and an exhaust product stream thereby defining a final specific entropy; and, wherein the starting specific entropy and the final specific entropy are less than about 1 kJ/kg° C. of each other.

Still further, there is provided a carbon-neutral method of converting a flare gas to an end product, the method including: (a) receiving a flow of a flare gas from a source; (b)

compressing the flare gas; (c) partially oxidizing the flare gas to provide a reprocessed gas; and, (d) converting the reprocessed gas into an end product; wherein steps (a) to (d) produce less than 2.0 kg of $CO_2$ per kg of flare gas received.

Yet additionally, there is provided a net-carbon negative method of capturing and converting flare gas to an end product comprising methanol, the method including: (a) receiving a flow of a flare gas from a source; (b) compressing the flare gas to a predetermined partial oxidation pressure; (c) mixing the flare gas with air, to provide a fuel mixture, where the fuel mixture has a fuel/air equivalence ratio of greater than 1; (d) partially oxidizing the flare gas at a predetermined partial oxidation temperature to provide syngas, wherein the syngas has a ratio of $H_2/CO$ that is from about 1 to about 3; (e) converting the syngas into an end product at a predetermined synthesis temperature and a predetermined synthesis pressure; wherein the end product comprises methanol; and, wherein steps (a) to (e) are net carbon-negative, whereby these steps produce less than about −20 kg CO2e per kg of methanol produced.

Additionally, there is provided a carbon-neutral method of making an end product, the method including: (a) partially oxidizing the flare gas to provide a reprocessed gas; (b) converting the reprocessed gas into an end product; wherein steps (a) to (b) produce less than 2.0 kg of $CO_2$ per kg of flare gas partially oxidized; and, wherein steps (a) to (b) are net carbon-negative, whereby these steps produce less than about −20 kg CO2e per kg of end product produced.

Still further there is provided, a method of converting a flare gas to an end product, the method including: (a) receiving a flare gas from a source; (b) forming a mixture of the flare gas and an oxygen source, wherein the oxygen source primarily comprises air, thereby defining a fuel/air mixture, wherein the fuel/air mixture defines a starting specific entropy; (c) partially oxidizing the fuel/air mixture at a predetermined reformer temperature; thereby providing a reprocessed gas flow comprises a syngas having a syngas composition; (d) converting the reprocessed gas flow in a synthesis unit to thereby provide a first product stream comprising an end product and an exhaust product stream; thereby defining a final specific entropy; wherein the starting specific entropy and the final specific entropy are less than about 1 kJ/kg° C. of each other; and, wherein steps (a) to (d) produce less than 2.0 kg of $CO_2$ per kg of flare gas received.

Moreover, there is provided a system for converting flare gas into an end product, the system having: a reformer stage and a synthesis stage; the reformer stage including: an intake for receiving a flow of a flare gas; an intake for receiving a flow of air; an air breathing reformer, configured to operate under rich fuel/air conditions; wherein the reformer is configured to operate in a partial oxidation combustion window; whereby the reformer is configured to convert mixture of flare gas and air into a syngas; a line for flowing the syngas to the synthesis stage; the synthesis stage including: a line for receiving a flow of syngas from the reformer stage; a synthesis unit configured to receive the syngas and convert the syngas into an end product; and, a control system configured to operate the reformer stage at a predetermined partial oxidation temperature and a predetermined partial oxidation pressure; and the synthesis stage at a predetermined synthesis temperature and a predetermined synthesis pressure.

Moreover, there is provided a method of converting a flare gas to an end product, the method including: (a) receiving a flare gas from a source; (b) forming a mixture of the flare gas and an oxygen source, wherein the oxygen source primarily comprises air, thereby defining a fuel/air mixture, wherein the fuel/air mixture defines a starting specific entropy; (c) partially oxidizing the fuel/air mixture at a predetermined reformer temperature; thereby providing a reprocessed gas flow comprises a syngas having a syngas composition; (d) converting the reprocessed gas flow in a synthesis unit to thereby provide a first product stream comprising an end product and an exhaust product stream; thereby defining a final specific entropy; wherein the starting specific entropy and the final specific entropy are less than about 1 kJ/kg° C. of each other; and, wherein steps a) to d) are net carbon-negative, whereby these steps produce less than about −20 kg CO2e per kg of end product provided.

Furthermore, there is provided a method of converting a flare gas to an end product, the method comprises: (a) receiving a flare gas from a source; (b) forming a mixture of the flare gas and an oxygen source, wherein the oxygen source primarily comprises air, thereby defining a fuel/air mixture, wherein the fuel/air mixture defines a starting specific entropy; (c) partially oxidizing the fuel/air mixture at a predetermined reformer temperature; thereby providing a reprocessed gas flow comprises a syngas having a syngas composition; (d) converting the reprocessed gas flow in a synthesis unit to thereby provide a first product stream comprising an end product and an exhaust product stream; thereby defining a final specific entropy; wherein the starting specific entropy and the final specific entropy are less than about 1 kJ/kg° C. of each other; wherein steps a) to d) produce less than 2.0 kg of $CO_2$ per kg of flare gas received; and, wherein steps (a) to (d) are net carbon-negative, whereby these steps produce less than about −20 kg CO2e per kg of end product provided.

Yet additionally, there is provided these systems, methods and devices having one or more of the following features: wherein the reformer is a reciprocating engine; and the reciprocating engine has one, more than one, or all of: a compression ratio in the range of about 8:1 to about 17:1; an inlet manifold air temperature of ambient temperature to about 300° C.; an inlet manifold air pressure of ambient to about 5 bar; a spark timing between TDC and 50 degrees before TDC; and, an engine speed for from about 8,000 rpm to about 1,500 rpm.

Additionally, there is provided these systems, methods and devices having one or more of the following features: wherein the reformer is a reciprocating engine; and the reciprocating engine has at least one of: a compression ratio in the range of about 8:1 to about 17:1; an inlet manifold air temperature of ambient temperature to about 300° C.; an inlet manifold air pressure of ambient to about 5 bar; a spark timing between TDC and 50 degrees before TDC; or, an engine speed for from about 8,000 rpm to about 1,500 rpm;

Yet additionally, there is provided these systems, methods and devices having one or more of the following features: wherein the reformer comprises a gas turbine assembly; and the gas turbine assembly has one, more than one, or all of: a first partial oxidation combustor; a two-stage combustion process; a gas turbine combustor; and, a combustion cycle time of from 5 to 50 milliseconds.

In addition, there is provided these systems, methods and devices having one or more of the following features: wherein the reformer comprises a gas turbine assembly; and the gas turbine assembly has at least one of: a first partial oxidation combustor; a two-stage combustion process; a gas turbine combustor; or, a combustion cycle time of from 5 to 50 milliseconds.

Still further, there is provided these systems, methods and devices having one or more of the following features: has a hydrogen separation unit to provide a stream of a recovered hydrogen to the system; has a hydrogen separation unit to provide a stream of a recovered hydrogen for mixing with the syngas; has a hydrogen separation unit to provide a stream of a recovered hydrogen for mixing with the syngas; and wherein the control system is configured to control the mixing of the recovered hydrogen with the syngas to provide a predetermined $H_2$ to CO ratio.

Additionally, there is provided these systems, methods and devices having one or more of the following features: wherein the air breathing reformer comprises a reciprocating engine having a variable compression ratio; and, further has: a sensor system to detect ignition/combustion behavior over a range from pre-ignition to misfire; and configured to send a detected ignition/combustion behavior information; wherein the control system is in control communication with the sensor system and the engine; wherein the control system is configured to adjust the engine compression ratio based on the detected ignition/combustion behavior information; and, thereby the control system is configured to adjust the compression ratio in response to a variability in a composition of the flare gas.

Further, there is provided these systems, methods and devices having one or more of the following features: has a fuel conditioning system to remove liquids and contaminants harmful to a downstream component, thereby providing a conditioned fuel source; has a separation assembly associated with the synthesis unit, wherein a byproduct is selectively removed from the synthesis unit in situ; has a separation assembly associated with the synthesis unit, wherein a byproduct is selectively removed from the synthesis unit by a liquid or gaseous sweep; wherein the byproduct is water; wherein the separation assembly comprises at least one of a device for membrane separation, a device for absorption, a device for adsorption, or a device for distillation; has a separation assembly associated with the synthesis unit, wherein the end product is selectively removed from the synthesis unit in situ; has a separation assembly associated with the synthesis unit, wherein the end product is selectively removed from the synthesis unit by a liquid or gaseous sweep; wherein the end product is methanol; wherein the separation assembly comprises at least one of a device for membrane separation, a device for absorption, a device for adsorption, or a device for distillation.

Yet additionally, there is provided these systems, methods and devices having one or more of the following features: wherein the engine is a compression ignition engine; wherein the engine is a spark ignition engine; wherein the engine is an opposed-piston free-piston linear internal combustion engine; wherein the engine is a crankshaft-driven opposed-piston internal combustion engine with a crankshaft phaser to rotate a phasing of one piston relative to the other thereby modifying overall compression ratio; wherein the engine is a conventional spark-ignited reciprocating engine, wherein the engine is configured for a variable effective compression ratio utilizing camshaft phasers to rotate intake and exhaust camshafts to thereby affect a valve opening and closing; wherein the engine is configured for a variable effective compression ratio utilizing a variable lift, a duration valvetrain, or both to affect a valve opening and closing; and, wherein the engine comprises a multi-link system configured to rotate a crankshaft, and comprising an actuator motor configured to change an endpoint of the multi-link system.

Moreover, there is provided these systems, methods and devices having one or more of the following features: including passing the flare gas flow through a first heat exchanger, wherein the first heat exchanger is receiving the reprocessed gas flow from the reformer; whereby the flare gas flow is heated; including controlling the partial oxidation in the reformer; whereby the composition of the syngas in the reprocessed gas flow does not change with the varying composition of the flare gas flow; wherein the predetermined synthesis temperature is from about 200° C. to about 300° C.; wherein the predetermined synthesis pressure is from about 30 bar to about 100 bar; wherein the predetermined synthesis temperature is from about 200° C. to about 300° C. and the predetermined synthesis pressure is from about 30 bar to about 100 bar; wherein second product stream having at least 93% methanol and is thereby at least 93% pure; wherein second product stream having from 90% to 95% methanol and is thereby from 90% to 95% pure; wherein the reformer having an air-breathing reformer; wherein the reformer having one or more of a gas turbine engine, a combustion box, an internal combustion engine, an otto cycle reciprocating engine, a diesel cycle reciprocating engine; wherein the rich fuel/air mixture has a fuel/air equivalence ratio of from 1.1 to about 4; wherein the rich fuel/air mixture has a fuel/air equivalence ratio of from about 1.5 to about 3.0; wherein the rich fuel/air mixture has a fuel/air equivalence ratio of from about 1.5 to about 2.5; wherein a ratio of $H_2$ to CO in the syngas is from about 1.0 to about 2.0; wherein a ratio of $H_2$ to CO in the syngas is from 0.8 to 2.5; wherein a ratio of $H_2$ to CO in the syngas is from about 2 to about 3; wherein a ratio of $H_2$ to CO in the syngas is from 1.1-2.5; wherein a ratio of $H_2$ to CO is less than 3; wherein a ratio of $H_2$ to CO is less than 2.5; wherein the reformer is a reciprocating engine; and the reciprocating engine has one, more than one, or all of: a compression ratio in the range of about 8:1 to about 17:1; an inlet manifold air temperature of ambient temperature to about 300° C.; an inlet manifold air pressure of ambient to about 5 bar; and, a spark timing between TDC and 50 degrees before TDC; an engine speed from about 1,500 rpm to about 8,000 rpm; wherein the reformer is selected from the group consisting of a two-stroke reciprocating engine and a four-stroke reciprocating engine; wherein the reformer is a gas turbine assembly; and the gas turbine assembly has one, more than one, or all of: a first partial oxidation combustor; a two-stage combustion process; a gas turbine combustor; and, a combustion cycle time of from 5 to 50 milliseconds; comprising capturing and using heat generated from the partial oxidation of the rich fuel/air mixture, wherein the heat is used in the continuous method of converting a flare gas to methanol; wherein the flare gas flow has a rate of about 50,000 scfd to about 30,000,000 scfd; wherein the flare gas flow has a rate of greater than about 200,000 scfd; wherein the flare gas flow has a rate of greater than about 200,000 scfd; wherein the flare gas flow has a composition, where in the composition varies over time; wherein the partial oxidation of the flare gas is conducted at a specific entropy of greater than about 7.1 kJ/kg° C., wherein a reference state for the specific entropy is based upon −273.15° C. and 1 atmosphere; wherein the partial oxidation of the flare gas is conducted at a specific entropy of greater than about 7.5 kJ/kg° C., wherein a reference state for the specific entropy is based upon −273.15° C. and 1 atmosphere; wherein the partial oxidation of the flare gas is conducted at a specific entropy of greater than about 8.0 kJ/kg° C., wherein a reference state for the specific entropy is based upon −273.15° C. and 1 atmosphere; wherein the partial oxidation of the flare gas is conducted at a specific entropy of about 7.1 kJ/kg° C. to about 8.6 kJ/kg, wherein a reference state for the specific entropy is based upon −273.15° C. and 1 atmosphere; including providing the fuel/air mixture at a predetermined reformer pressure, to a reformer, wherein the partial oxidation is conducted in the reformer at the predetermined reformer temperature; including controlling the pressure and the temperature of the reprocessed gas flow to provide a predetermined synthesis temperature and a predetermined synthesis pressure of the reprocessed gas flow; wherein the end product is selected from the group consisting of methanol, ethanol, ammonia, mixed alcohols, dimethyl-ether, and F-T liquids; wherein the end product consist of methanol; wherein the end product consists essentially of methanol; wherein the predetermined temperatures and pressures comprises one, more than one, or all of: (i) the predetermined partial oxidation temperature is from about 700° C. to about 1,200° C.; (ii) the predetermined partial oxidation pressure is from about 1 bar to about 70 bar; (iii) the predetermined synthesis temperature is from about 200° C. to about 300° C.; and, (iv) the predetermined synthesis pressure is from about 30 bar to about 100 bar; wherein a variation in a composition of the flare gas does not change a composition of the end product; and wherein the variation in the composition of the flare gas does not require a change in one or more than one, of the predetermined synthesis temperature, the predetermined synthesis pressure, and the predetermined reformer temperature, and the predetermined reformer temperature; wherein a byproduct is selectively removed from the synthesis unit in situ; wherein a byproduct is selectively removed from the synthesis unit by a liquid or gaseous sweep; wherein the byproduct is water; wherein the selected removal is by at least one of membrane separation, absorption, adsorption, or distillation; wherein the end product is selectively removed from the synthesis unit in situ; wherein the end product is selectively removed from the synthesis unit by a liquid or gaseous sweep; wherein the end product is methanol; wherein the selected removal is by at least one of membrane separation, absorption, adsorption, or distillation; wherein the source of the flare has a composition as set out in Tables 1 and 2; and wherein the source of the flare has a varying composition, wherein the varying composition is within the range of compositions set out in Tables 1 and 2.

Still further, there is provided these systems, methods and devices having one or more of the following features: wherein the step of partially oxidizing the flare gas, comprises combusting a mixture of the flare gas and a source of oxygen; wherein the oxygen source comprises air, and the mixture has a fuel/air equivalence ratio of greater than 1; wherein the oxygen source comprises air, and the mixture has a fuel/air equivalence ratio of from 1.1 to about 4; wherein the oxygen source comprises air, and the mixture has a fuel/air equivalence ratio of from about 1.5 to about 3.0; using, water, steam, or both in the step of partially oxidizing the flare gas; wherein the step of partially oxidizing the flare gas occurs in an air-breathing reformer; wherein the step of partially oxidizing the flare gas takes place in a reformer stage of a liquid-to-gas system; and wherein, the reformer stage comprises one or more of a gas turbine engine, a combustion box, and a reciprocating engine; wherein the step of converting the reprocessed gas into an end product takes place under a predetermined synthesis temperature and a predetermined synthesis pressure; wherein the predetermined synthesis temperature is from about 200° C. to about 300° C.; wherein the predetermined synthesis pressure is from about 30 bar to about 100 bar; wherein the predetermined synthesis temperature is from about 200° C. to about 300° C. and the predetermined synthesis pressure is from about 30 bar to about 100 bar; wherein the step of partially oxidizing the flare gas takes place under a predetermined reformer temperature and a predetermined reformer pressure; wherein the predetermined reformer temperature is from about 700° C. to about 1,200° C.; wherein the predetermined reformer pressure is from about 1 bar to about 70 bar; wherein the predetermined reformer temperature is from about 700° C. to about 1,200° C.; and the predetermined reformer pressure is from about 1 bar to about 70 bar; wherein the step of converting the reprocessed gas into an end product takes place under a predetermined synthesis temperature and a predetermined synthesis pressure; and the predetermined synthesis temperature is from about 200° C. to about 300° C. and the predetermined synthesis pressure is from about 30 bar to about 100 bar; the step of removing an excess of oxygen from the reprocessed gas; wherein the reprocessed gas contains a synthesis gas; wherein the reprocessed gas consists of a synthesis gas; wherein a variation in a composition of the flare gas does not change a composition of the end product; wherein the step of converting the reprocessed gas into an end product takes place under a predetermined synthesis temperature and a predetermined synthesis pressure; wherein the step of partially oxidizing the flare takes place under a predetermined reformer temperature and a predetermined reformer pressure; wherein a variation in a composition of the flare gas does not change a composition of the end product; and wherein the variation in the composition of the flare gas does not require a change in one or more than one, of the predetermined synthesis temperature and the predetermined synthesis pressure; wherein the step of converting the reprocessed gas into an end product takes place under a predetermined synthesis temperature and a predetermined synthesis pressure; wherein the step of partially oxidizing the flare takes place under a predetermined reformer temperature and a predetermined reformer pressure; wherein a variation in a composition of the flare gas does not change a composition of the end product; and wherein the variation in the composition of the flare gas does not require a change in one or more than one, of the predetermined synthesis temperature, the predetermined synthesis pressure, and the predetermined reformer temperature; wherein less than 1.0 kg of $CO_2$ per kg of flare gas processed is produced; wherein less than 0.5 kg of $CO_2$ per kg of flare gas is produced; wherein less than 0.1 kg of $CO_2$ per kg of flare gas processed is produced; wherein less than 0.05 kg of $CO_2$ per kg of flare gas processed is produced; wherein the reprocessed gas comprises a syngas; wherein the reprocessed gas consists essentially of a syngas; wherein the reprocessed gas consists of a syngas; where the end product is a liquid; wherein the end product is selected from the group consisting of methanol, ethanol, mixed alcohols, ammonia, dimethyl-ether, and F-T liquids; wherein the end product contains methanol; wherein the end product consists essentially of methanol.; wherein steps (a) to (d) or (a) to (e) are net carbon-negative, whereby these steps produce less than about −20 kg CO2e per kg of end product produced; wherein steps (a) to (d) or (a) to (e) are net carbon-negative, whereby these steps produce less than about −40 kg CO2e per kg of end product produced; wherein steps (a) to (d) or (a) to (e) are net carbon-negative, whereby these steps produce less than about −100 kg CO2e per kg of end product produced; wherein steps (a) to (d) or (a) to (e) are net carbon-negative, whereby these steps produce from about −20 kg CO2e to about −150 kg CO2e, per kg of methanol produced.; wherein steps (a) to (d) or (a) to (e) are net carbon-negative, whereby these steps produce from about −40 kg CO2e to about −130 kg CO2e, per kg of methanol produced; and, wherein the predetermined temperatures and predetermined pressures includes one, more than one, or all of: (i) the predetermined partial oxidation temperature is from about 900° C. to about 1,150° C.; (ii) the predetermined partial oxidation pressure is from about 1 bar to about 70 bar; (iii) the predetermined synthesis temperature is from about 200° C. to about 300° C.; and, (iv) the predetermined synthesis pressure is from about 30 bar to about 100 bar.

Yet additionally, there is provided these systems, methods and devices having one or more of the following features: wherein less than about −40 kg CO2e per kg of end product produced; wherein less than about −100 kg CO2e per kg of end product produced; wherein from about −20 kg CO2e to about −150 kg CO2e, per kg of methanol produced; wherein from about −40 kg CO2e to about −130 kg CO2e, per kg of methanol produced; wherein less than 1.0 kg of CO2 per kg of flare gas is produced; wherein less than 0.5 kg of CO2 per kg of flare gas is produced; wherein less than 0.1 kg of CO2 per kg of flare gas is produced; wherein less than 0.05 kg of CO2 per kg of flare gas is produced; wherein the partial oxidation of the flare gas is conducted at a specific entropy of greater than about 7.1 kJ/kg° C., wherein a reference state for the specific entropy is based upon −273.15° C. and 1 atmosphere; wherein the partial oxidation of the flare gas is conducted at a specific entropy of greater than about 7.5 kJ/kg° C., wherein a reference state for the specific entropy is based upon −273.15° C. and 1 atmosphere; w herein the partial oxidation of the flare gas is conducted at a specific entropy of greater than about 8.0 kJ/kg° C., wherein a reference state for the specific entropy is based upon −273.15° C. and 1 atmosphere; wherein the partial oxidation of the flare gas is conducted at a specific entropy of about 7.1 kJ/kg° C. to about 8.6 kJ/kg° C., wherein a reference state for the specific entropy is based upon −273.15° C. and 1 atmosphere.

Moreover, there is provided these systems, methods and devices having one or more of the following features: wherein the starting specific entropy and the final specific entropy are less than about 0.5 kJ/kg° C. of each other; wherein the starting specific entropy and the final specific entropy are less than 0.3 kJ/kg° C. of each other; and, wherein the starting specific entropy and the final specific entropy are less than 0.2 kJ/kg° C. of each other.

Moreover, there is provided these systems, methods and devices having one or more of the following features: wherein the reformer is a reciprocating engine; and the reciprocating engine has one, more than one, or all of: a compression ratio in the range of about 8:1 to about 17:1; an inlet manifold air temperature of ambient temperature to about 300° C.; an inlet manifold air pressure of ambient to about 5 bar; to about 300° C.; a spark timing that is between TDC and 50 degrees before TDC; and, an engine speed for from about 8,000 rpm to about 1,800 rpm; wherein the reformer is selected from the group consisting of a two-stroke reciprocating engine and a four-stroke reciprocating engine; wherein the reformer is a gas turbine assembly; and the gas turbine assembly has one, more than one, or all of: a first partial oxidation combustor; a two-stage combustion; a gas turbine combustor; and, a combustion cycle time of from 5 to 50 milliseconds.

Still further there is provided these systems, methods and devices having one or more of the following features: wherein the rich fuel/air mixture has a fuel/air equivalence ratio of from 1.1 to about 4; wherein the rich fuel/air mixture has a fuel/air equivalence ratio of from about 1.5 to about 3.0; wherein the rich fuel/air mixture has a fuel/air equivalence ratio of from about 1.5 to about 2.5; wherein the ratio of $H_2$ to CO in the syngas is from about 1.0 to about 2.0; wherein the ratio of $H_2$ to CO in the syngas is from 0.8 to 2.5; wherein the ratio of $H_2$ to CO in the syngas is from about 2 to about 3; wherein the ratio of $H_2$ to CO in the syngas is from 1.1-2.5; wherein the ratio of $H_2$ to CO is less than 3; wherein the ratio of $H_2$ to CO is less than 2.5.

BRIEF DESCRIPTION OF THE DRAWINGS

FIG. 22 is a table showing global warming potential values.

Figure 1:
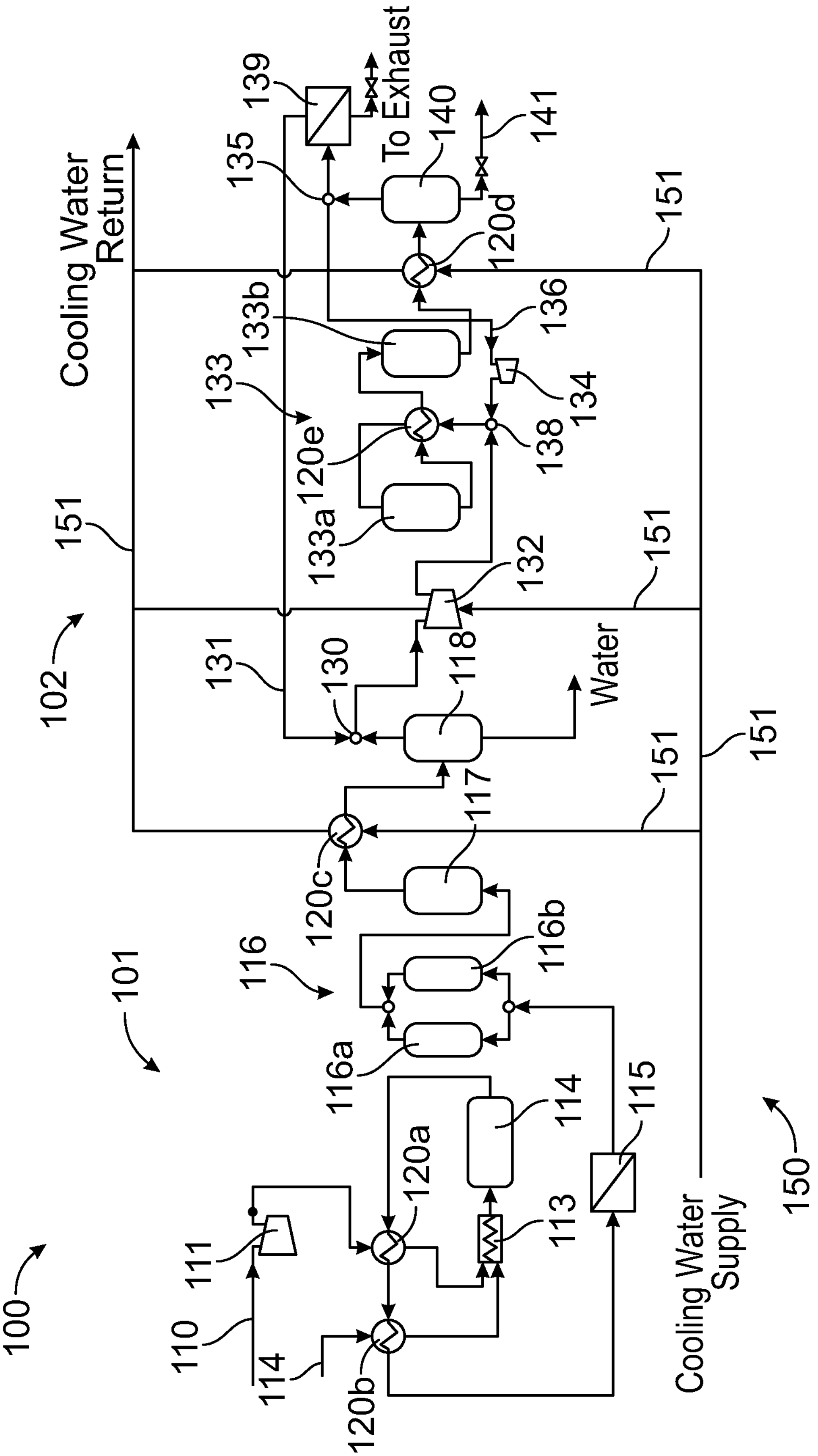
FIG. 1 is a schematic flow diagram of an embodiment of a system and process in accordance with the present inventions.

The T-S diagrams of these Figures, are all plotted and depicted on graphs having the same axes. The Specific Entropy axis (x axis) is in units of kJ/kg° C., and describes the entropy per unit mass of air. The Temperature axis (y axis) is in ° C. and describes the fluid temperature, assumed to have properties similar to air. The relationship between temperature and lines of constant pressure are governed by the physical properties of the fluid.

DESCRIPTION OF THE PREFERRED EMBODIMENTS

The present inventions generally relate to systems, devices and methods to recover in an economical fashion usable materials from waste gas, e.g., flare gas. In general, embodiments of the present inventions relate to systems, devices and methods, to achieve such recovery at smaller, isolated or remote locations or point sources for the waste gas.

In general, embodiments of the present inventions relate to methods, devices and systems for utilizing flare gas to produce a reprocessed gas and then utilizing that reprocessed gas to provide useful and economically viable materials. In particular, embodiments of the present inventions relate to methods, devices and system for producing, recovering and processing reprocessed gas to provide useful and economically viable materials.

Embodiments of the present inventions have a reciprocating engine, a gas turbine engine or both, to produce reprocessed gas, preferably syngas. These embodiments can be modular and can easily and readily be positioned at difficult to access locations, locations with limited area for placement of the systems, and combinations and variations of these, where flare gas typically is generated.

Systems and Processes—Generally

Generally, embodiments of the present systems and methods can be associated with a source of hydrocarbon fuel. The hydrocarbon fuel can be a solid, a liquid, a gas, a slurry and combinations and variations of these. Preferably, the hydrocarbon fuel is a waste gas, and in particular a flare gas. The system is in fluid communication with the hydrocarbon fuel source, by way of for example, pipes, conduits tubulars, hoses and the like, and in this manner the hydrocarbon fuel is provided to the system. The hydrocarbon source can be an active source, in that the hydrocarbons are actively flowing, e.g., flowing from a borehole in the earth, a producing hydrocarbon well, a refinery, or a chemical plant. The hydrocarbon source can be a static source, in that the hydrocarbons are contained in, and obtained from, a holding or collected source, e.g., a holding tank, a tank farm, a tank truck, a rail car, a barge, a container and the like. The source of hydrocarbon fuel can be combinations and variations of active sources, and static sources Generally, the hydrocarbon fuel source, e.g., flare gas, and an oxygen source, e.g., air, are feed to a reformer unit, where the hydrocarbon fuel source is converted through preferably a controlled and predetermined combustion into reprocessed gas, e.g., syngas. This reformer stage of the general system and method, can also have equipment for handling and processing the incoming hydrocarbon fuel source, e.g., flare gas and oxygen source, e.g., air, as well as, equipment to process the reprocessed gas, e.g., syngas, such as for example, valves, controllers, compressors, sensors and monitors, temperature control systems, mixers, filters and screens, separators, equipment to remove water, guard beds, guard bed reactors, deoxo reactors, and other handling and processing equipment and methods. It being understood that some or all of the reprocessed gas, e.g., syngas, processing equipment and methods can be in stages, or located in the general system places other than the reformer stage.

Generally, the reformer, and the reformer stage, are preferably operating in a predetermined manner to optimize the composition of reprocessed gas, e.g., syngas, that is obtained, such that the reprocessed gas, e.g., syngas, has a predetermined composition that is determined for optimum performance in its conversion to a value-add product, e.g., methanol, ethanol, ammonia, dimethyl-ether, F-T liquids, and other fuels or chemicals, and combination and variations of these.

Generally, the reprocessed gas, e.g., syngas, from the reformer is provided to a synthesis unit, e.g., a methanol unit, where the reprocessed gas, e.g., syngas, is converted to a value-add product, e.g., methanol, ethanol, ammonia, dimethyl-ether, F-T liquids, and other fuels or chemicals, and combination and variations of these. Preferably, the value-add product is collected and stored as a liquid. It being understood that the value-add product can be gaseous, or in some other state. This synthesis stage, e.g., methanol synthesis stage, can have other equipment and methods for processing and handling the incoming reprocessed gas, e.g., syngas, as well as, for handling and processing the value-add product, e.g., methanol, including for example, valves, controllers, compressors, sensors and monitors, mixers, filters and screens, temperature control systems, separators, equipment to remove water and other handling and processing equipment and methods. The pressure of the reprocessed gas, e.g., syngas, can be, and preferably is controlled, e.g., compressed, prior to being provided to the synthesis unit, e.g., methanol unit, when forming the value-add product, e.g., methanol.

Generally, the systems and methods may have additional separation and processing equipment, for example, to remove hydrogen from the value-add product, e.g., methanol. In these embodiments, preferably the hydrogen can be used to generate electricity to operate the system, as well as, potentially other devices, e.g., excess electricity is produced by the system.

The stages can be in a single system, in a single integrated system, in separate systems, in two or more modular systems and combinations and variations of these.

Generally, the systems and methods have control systems. The control systems can include computers having possessors, memory and data storage. The control systems further can include controllers, e.g., program logic controllers ("PLC"), input/output ("I/O"), sensors, graphic user interface (GUI) and communication protocols and capabilities, e.g., web servers, cellular, satellite. In embodiments, the control system includes a blockchain for authenticating the operation of the system and method, e.g., mass balance of method and operation, and to validate, encrypt and authentic data related to carbon capture, reduction of greenhouse gases, carbon credits, and the like.

Thus, the preferred embodiments of the present systems relate to liquid-to-gas systems and methods, e.g., flare gas to methanol.

In general, the reformer can be one or more devices or assembly of devices that combusts the waste gas, e.g., flare gas, under controlled and predetermined conditions to provide a reprocessed gas. Preferably one or more of the temperature, pressure, and composition for the reprocessed gas is optimized for use in the synthesis stage, and the controlled and predetermined conditions for operation of the reformer are optimized to provide this optimized temperature, pressure, and composition of the reprocessed gas. Thus, and in general, the reformer can have one or more combustion device, a combustion box, engine, internal combustion engine, reciprocating engine, rotary engine, gasoline engine (i.e., spart ignition), diesel engine (i.e., compression ignition), jet engine, turbine engine, gas turbine engine, air-breathing engine, air breathing combustion device and combinations and variations of these, as well as other peripheral or ancillary devices and equipment.

Embodiments of the present inventions can be used to take uneconomic hydrocarbon-based fuels at a well-head and remote locations that are primarily gaseous hydrocarbons and convert them to a more valuable easily condensable or liquid compounds, such as methanol. One source of fuel could be associated gas or flare gas, which is produced as a byproduct at oil wells. Another source is flare gas produced by industrial processes, such as refinery flare gas. Another source could be biogas from landfill or anaerobic digesters.

In general, the embodiments of the present systems and methods use waste gas that is preferably flare gas. Examples of the composition of flare gas that any of the reformers of the present systems and methods can process into reprocessed gas, which is then processed by the synthesis units into a value-added product (e.g., methanol, ethanol, ammonia, dimethyl-ether, F-T liquids, and other fuels or chemicals) are set forth in Table 1 and Table 2. The flare gasses can have one or more, and all of the constituents or components in one or more of the various amounts set forth in these tables.

TABLE 1

Examples of flare glass compositions

| Gas Constituent | | % of Constituent | | |
|---|---|---|---|---|
| Name | Formula | Min. | Max | Average |
| Methane | $CH_4$ | 7.17 | 82.0 | 43.6 |
| Ethane | $C_2H_6$ | 0.55 | 13.1 | 3.66 |
| Propane | $C_3H_8$ | 2.04 | 64.2 | 20.3 |
| n-Butane | $C_4H_{10}$ | 0.199 | 28.3 | 2.78 |
| Isobutane | $C_4H_{10}$ | 1.33 | 57.6 | 14.3 |
| n-Pentane | C5H12 | 0.008 | 3.39 | 0.266 |
| Isopentane | C5H1; | 0.096 | 4.71 | 0.530 |
| neo-Pentane | $CSH_{12}$ | 0.000 | 0.342 | 0.017 |
| n-Hexane | $C_6H_{14}$ | 0.026 | 3.53 | 0.635 |
| Ethylene | $C_2H_4$ | 0.081 | 3.20 | 1.05 |
| Propylene | $C_3H_6$ | 0.000 | 42.5 | 2.73 |
| 1-Butene | $C_4H_8$ | 0.000 | 14.7 | 0.696 |
| Carbon monoxide | CO | 0.000 | 0.932 | 0.186 |
| Carbon dioxide | $CO_2$ | 0.023 | 2.85 | 0.713 |
| Hydrogen sulfide | $H_2S$ | 0.000 | 3.80 | 0.256 |
| Hydrogen | $H_2$ | 0.000 | 37.6 | 5.54 |
| Oxygen | $O_2$ | 0.019 | 5.43 | 0.357 |
| Nitrogen | $N_2$ | 0.073 | 32.2 | 1.30 |
| Water | $H_2O$ | 0.000 | 14.7 | 1.14 |

TABLE 2

Examples of biogas types of flare gas compositions

| | Source of biogas type flare gas | | | | |
|---|---|---|---|---|---|
| Constituent | Municipal waste | Wastewater | Agricultural/ Animal waste | Waste from food industry | Landfill |
| $CH_4$ (vol %) | 50-60 | 55-77 | 50-75 | 68-75 | 35-70 |
| $C0_2$ (vol %) | 34-38 | 36-38 | 37-38 | 26 | 15-60 |
| | | 19-33 | 19-33 | | |
| | | 30-45 | 30-50 | | |
| | | 35-45 | 30-40 | | |

TABLE 2-continued

| Examples of biogas types of flare gas compositions | | | | | |
|---|---|---|---|---|---|
| | Source of biogas type flare gas | | | | |
| Constituent | Municipal waste | Wastewater | Agricultural/ Animal waste | Waste from food industry | Landfill |
| $N_2$ (vol %) | 0-5 | | <1 | | <1-40 |
| | | <2 | <1-2 | | |
| | | <1 | <3 | | |
| $0_2$ (vol %) | 0-1 | <0.5 | <0.5 | | <0.2-5 |
| $H_2$(vol %) | | | | | 0-5 |
| CO (vol %) | | | | | 0-3 |
| $H_2S$ (ppm) | 70-650 | 63-3,000 | 3-7,000 | 280-<21,500 | 0-20,000 |
| Aromatic (mg/m$^3$) | 0-200 | | | | 30-1,900 |
| Ammonia | | | 50-100 mg/m$^3$ | | 5 ppm |
| Halogenated compounds (mg/m$^3$) | 100-800 | | | | 1-2,900 |
| Benzene (mg/m$^3$) | | 0.1-0.3 | 0.7-1.3 | | 0.6-2.3 |
| Toluene (mg/m$^3$) | | 2.8-11.8 | 0.2-0.7 | | 1.7-5.1 |
| Siloxanes (ppmv) | | 1.5-15 | <0.4 | | 0.1-4 |
| Non-methane organics (% dry weight) | | | | | 0-0.25 |
| Volatile organics (% dry weight) | | | | | 0-0.1 |

Figure 20A:
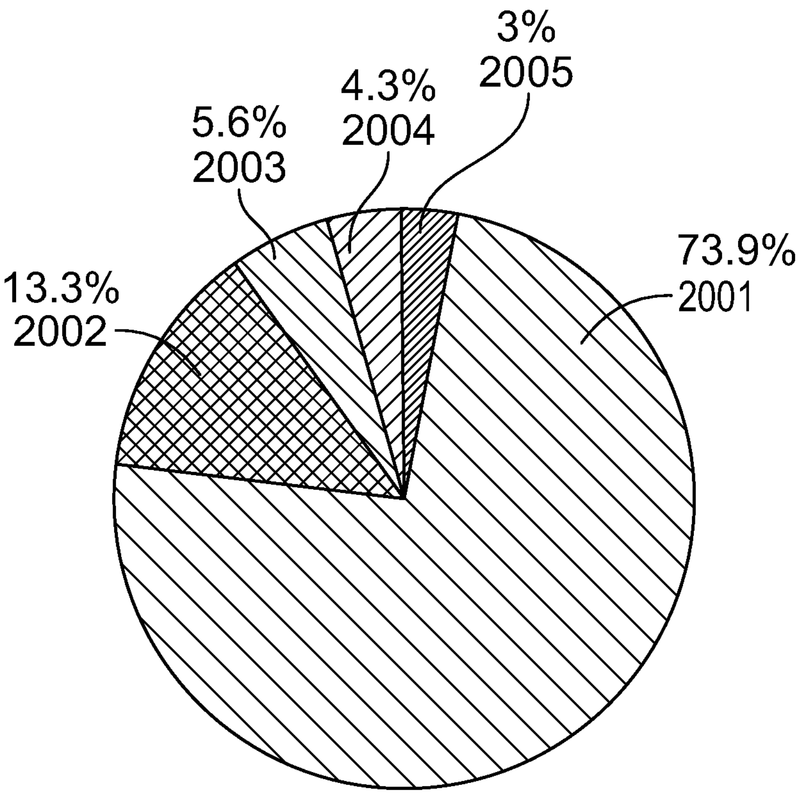
FIG. 20A is a pie chart showing the composition of an embodiment of a lean flare gas that can be processed by the present systems and methods in accordance with the present inventions.
Figure 20B:
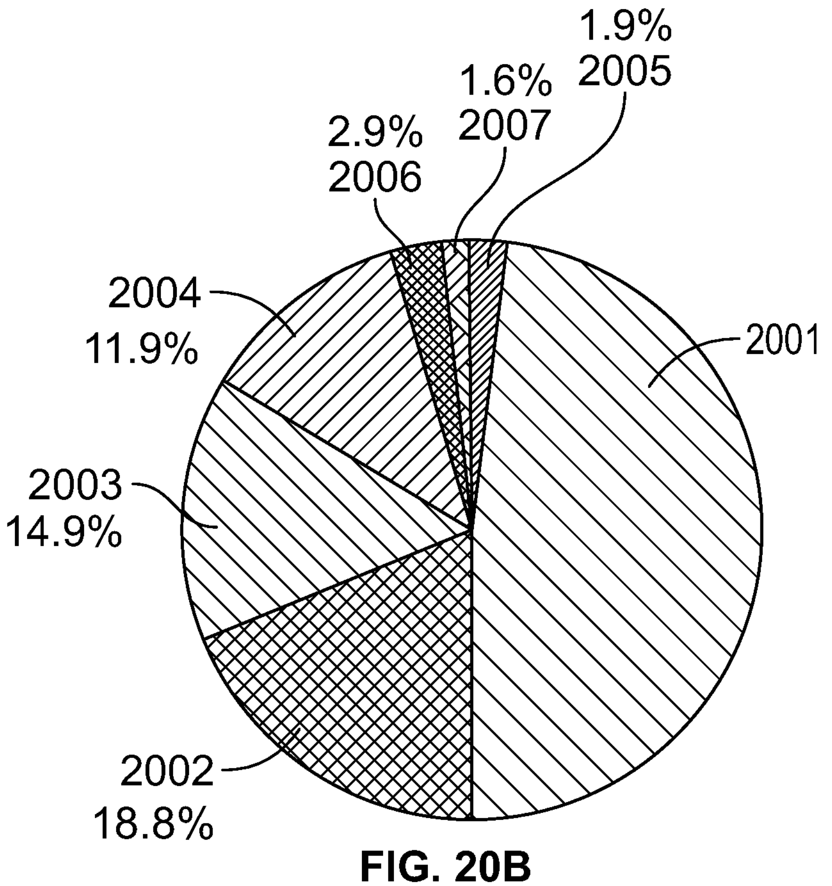
FIG. 20B is a pie chart showing the composition of an embodiment of a rich flare gas that can be processed by the present systems and methods in accordance with the present inventions.
Figure 21:
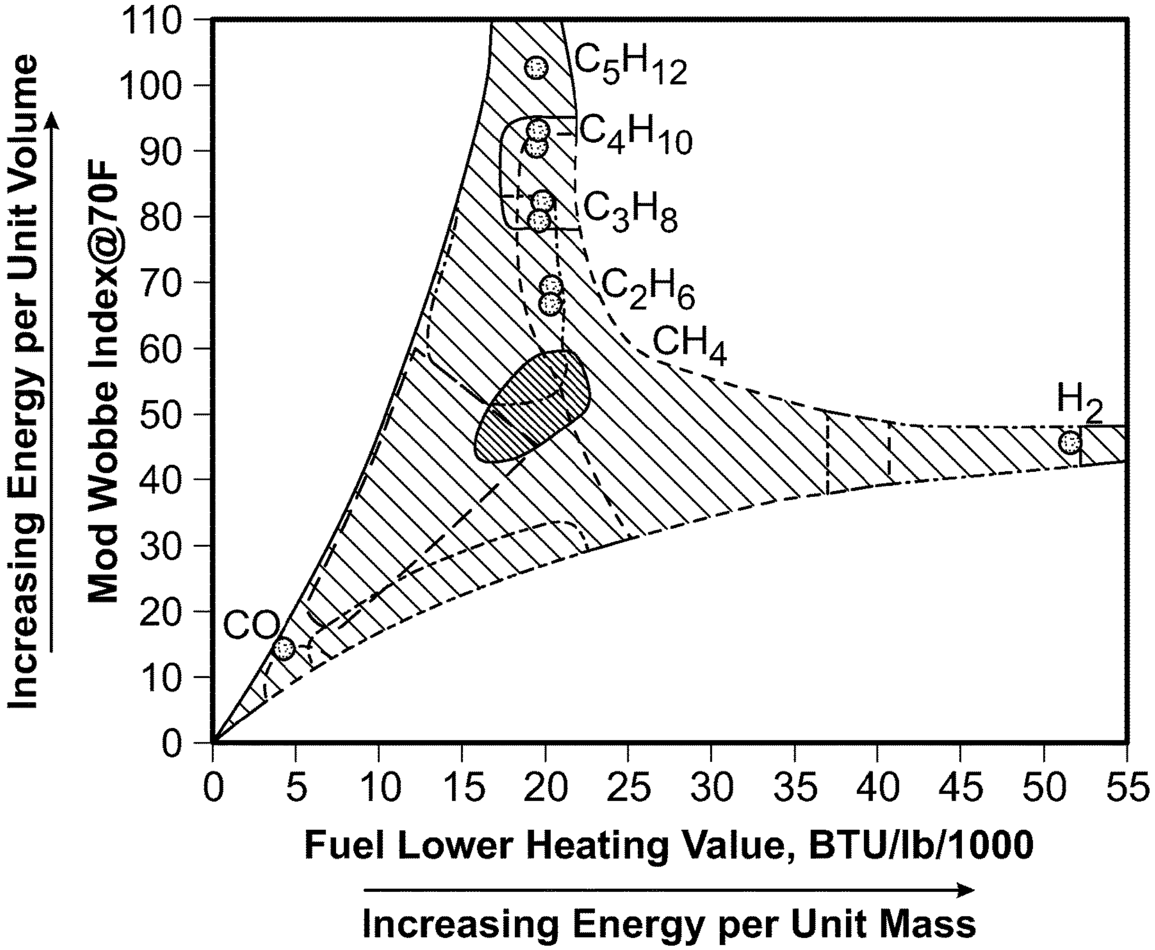
FIG. 21 is a graph showing the Wobbe number versus fuel heating value for various components and variations of flare gas that can be processed by embodiments of the present systems and methods in accordance with the present inventions.

FIGS. 20A and 20B also provide the compositions of flare gas that can occur and are processed by embodiments of the present inventions. FIG. 20A shows a typical composition of a lean flare gas, and FIG. 20B shows a typical composition of a rich flare gas. The lean and rich flare gases can have methane 2001, ethane 2002, propane 2003, butanes 2004, impurities 2005, the rich flare gas can also include pentanes 2006 and hexanes and heavier hydrocarbons 2007. FIG. 21 is a graph showing the Wobbe number vs fuel heating value for various components and variations of flare gases that can occur and are processed by embodiments of the present inventions.

These compositions (e.g., Table 1, Table 2, FIG. 20A, 20B, 21) represent compositions, and variations in compositions that the present systems and methods can utilize for gas-to-liquids synthesis (e.g., fare gas to liquid methanol) in embodiments of the present systems and methods in general, as well as embodiments of small modular systems.

The present inventions, including the embodiments of the Examples, can use and reprocess flare gases falling within any of the ranges of compositions and constituents set forth in Table 1, Table 2 and combinations of the compositions and ranges in these tables, as well as, other compositions and ranges of components. One of the reasons that these gases are non-economic is that the flare gas, composition is highly variable. Thus, the composition of the flare gas can change from source-to-source, from day-to-day at the same source (transients), from season-to-season (e.g., bio-gases), and over time as the source (e.g., well) ages. These variations have effects on combustion properties such as: heating value, cetane number (delay in time of ignition of fuel), and octane number (resistance to pre-ignition due to compression). Embodiments of the present reformers address these changes and provide the ability to operate in a consistent and efficient manner to process these varying flare gas compositions at a source site to provide a reprocessed gas, e.g., syngas, and preferably provide a consistent, predetermined and both syngas, with respect to the composition and temperature of the syngas.

Turning to FIG. 1 there is shown a generalized embodiment of a system and method for the conversion of a waste gas, e.g., flare gas, into a value-added product, e.g., methanol. The system 100 has a reformer stage 101 and a synthesis stage 102. The system 100 has an air intake 110, that feeds air through into a compressor 111, which compresses the air. The compressed air is feed through heat exchanger 120*a* into a mixer 113. The system has a waste gas, e.g., flare gas, intake 114. The waste gas flows through a heat exchanger 120*b* into the mixer 113. The mixer 113, provides a predetermined mix of air and waste gas, as taught and disclosed in this specification, to a reformer 114.

The fuel-air mixture that is formed in mixer 113 is preferably rich, more preferably having an overall fuel/air equivalence ratio ($\phi$ or ER) greater than 1, greater than 1.5, greater than 2, greater than 3, from about 1.5 to about 4.0, about 1.1 to about 3.5, about 2 to about 4.5, and about 1.1 to about 3, and greater values.

It being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing" reformers, and air breathing engines as used herein are understood to also include engines using air modified with the addition of water, oxygen or both.

The reformer 114 combusts the predetermined mixture of waste gas and air (e.g., flare gas and air) to form a reprocessed gas (e.g., syngas). The syngas flows through heat exchangers 120*a*, 120*b* and into a filter 115, e.g., a particulate filter.

After passing through the filter 115, the reprocessed gas (e.g., syngas) flows to a guard bed reactor assembly 116, having two guard bed reactors 116*a*, 116*b*. The guard bed reactor 116 has materials, e.g., catalysts, that remove contaminates and other materials from the syngas that would harm, inhibit or foul later apparatus and processes in the system. For example, the guard bed reactor 116 may contain catalyst or other materials to remove sulfur (e.g., iron sponge, zinc oxide or similar) and halogenated compounds.

After leaving the guard bed reactor 116, the reprocessed gas (e.g., syngas) flows to a deoxo reactor 117. The deoxo reactor 117 removes excess oxygen from the reprocessed gas (e.g., syngas) by oxidizing combustible compounds in the mixture such as methane, CO, and $H_2$, where the oxygen is converted to water. Catalyst for the deoxo reaction are platinum, palladium, and other active materials supported on alumina or other catalyst support materials.

The system 100 has a cooling system 150, which uses a cooling fluid, e.g., cooling water, that is flow through cooling lines, e.g., 151.

After leaving the deoxo reactor 117, the reprocessed gas (e.g., syngas) flows to heat exchanger 120*c*. The reprocessed gas (e.g., syngas) then flows from heat exchanger 120*c* to a water removal unit 118, e.g., a water knockout drum, demister, dryer, membrane, cyclone, desiccant or similar devices, where water is removed from the reprocessed gas (e.g., syngas). In general, the reprocessed gas (e.g., syngas) upon leaving unit 118 should have less than about 5% water by weight, less than about 2%, less than about 1% and less than about 0.1% water.

The overall (general) reaction for a rich fuel/air mixture to syngas is given by the equation:

$$ØCH_4+2[O_2+3.76\ N_2]\rightarrow aCO+bH_2+cCO_2+dH_2O+7.52\ N_2$$

Where stoichiometric coefficients a, b, c and are determined by the chemical kinetics, conservation of atomic species, and the reaction conditions.

In addition to syngas minor constituents in the gas exiting the reformer can include water vapor, $CO_2$, and various unburned hydrocarbons.

After leaving unit 118, the now dry reprocessed gas (e.g., syngas) is in the synthesis stage 102. In stage 102 the now dry reprocessed gas (e.g., syngas) flows to an assembly 130. Assembly 130 provides for the controlled addition of hydrogen from line 131 into the now dry reprocessed gas (e.g., syngas). In this manner the ratio of the syngas components can be adjusted and controlled to a predetermined ratio. The hydrogen is provided from hydrogen separate 139. The ratio adjusted dry reprocessed gas (e.g., syngas) leaves assembly 130 and flow to compressor 132. Compressor 132 compresses the reprocessed gas (e.g., syngas) to an optimum pressure as taught and disclosed in this specification, for use the synthesis unit 133. Preferably, the synthesis unit 133 is a two-stage unit with a first reactor unit 133*a* and a second reactor unit 133*b*. Each reactor is a pressure vessel where process gas flows through a catalyst bed in an exothermic reaction. The catalyst bed tubes are typically emersed in a pool of cooling water at a controlled temperature and pressure. Synthesis unit 133 also has heat exchanger 120*e*.

The synthesis unit 133 converts the ratio adjusted dry reprocessed gas (e.g., syngas) into a value-added product (e.g., methanol, ethanol, mixed alcohols, ammonia, dimethyl-ether, F-T liquids, and other fuels or chemicals). The value-added product (e.g, methanol, etc.) flows into to heat exchanger 120*d*. The value-added product (e.g, methanol, etc.) flows to a collection unit 140. The collection unit 140 collects the value-added product (e.g, methanol, etc.) and flows it through line 141 for sale, holding, or further processing.

Generally, the syngas is compressed to a pressure of about 15 to about 100 bar and preferably 30-50 bar, and about 25 to about 80 bar, at least about 10 bar, at least about 25 bar and at least about 50 bar, and greater and lower pressures. The temperature of the pressurized syngas is adjusted to a temperature of about 150° C. to about 350° C. and preferably 250° C., about 200° C. to about 300° C., about 250° C. to about 375° C., greater than 125° C., greater than 150° C., greater than 200° C., greater than 250° C., greater than 350° C., and less than 400° C., and higher and lower temperatures. The pressure and temperature-controlled syngas is then feed to reactors for transforming the syngas into a more useful, more easily transportable, and economically viable product such as methanol, ethanol, mixed alcohols, ammonia, dimethyl-ether, F-T liquids, and other fuels or chemicals. In a preferred embodiment methanol is produced using the reaction of syngas to methanol, reactions for hydrogenation of CO, hydrogenation of $CO_2$, and reverse water-gas shift using actively cooled reactors, such as a heat-exchanged reactor or boiling water reactor, and a copper containing catalyst such as $Cu/ZnO/Al_2O_3$ or the like. In general embodiments of the synthesis state can use the following reactions:

$$CO+2H_2\rightarrow CH_3OH\ \text{(CO hydrogenation)}$$

$$CO_2+3H_2\rightarrow CH_3OH+H_2O\ \text{(CO}_2\text{ hydrogenation)}$$

$$CO+H_2O\rightarrow CO_2+H_2\ \text{(reverse water-gas shift)}$$

Generally, and in preferred embodiments, the characteristic length scale of the reactors used in this system are sufficiently small (e.g., micro-channel or mini-channels) that they can be shaped into unconventional shapes and topologies using new 3D printing techniques for metals and other high-temperature materials, thus allowing compact packaging and tight control over reaction conditions. Other strategies for intensification of the downstream synthesis reactions can also be considered, such as selectively removing the product from the reactor in-situ, or in a closely coupled fashion, to shift the equilibrium-limited reaction to higher conversion. This process intensification may minimize the need for large recycle streams or allow the reaction to proceed at milder conditions (e.g., lower pressure) thereby increasing process safety margins.

Typically, in reacting the syngas to form the higher value product, unreacted $H_2$ is also produced. The $H_2$ can be collected and sold, or used to power the gas turbine or a second generator to produce additional electric power.

In general, the ratio of $H_2/CO$ in the syngas produced by the engine can be tailored to the downstream conversion process. For example, for methanol synthesis or Fischer-Tropsch (F-T) synthesis the ideal $H_2/CO$ ratio is 2-3. For ammonia synthesis or for hydrogen production, the maximum possible $H_2/CO$ ratio is desirable and can be enhanced by, for example, steam addition to promote the water-gas shift reaction. For ammonia and hydrogen production, the CO is not required by the downstream synthesis. As such, CO and $CO_2$ byproducts can be collected, sequestered, stored or utilized for other purposes.

The collection unit 140 also has a line that flows gas separated from the value-added product (e.g, methanol, etc.)

to valve 135, where it is sent to hydrogen separate 139, to a recycle loop 136 or both. Recycle loop has compressor 134 and valve 138 to feed the value-added product (e.g, methanol, etc.) back into the synthesis unit 133. Hydrogen separation can be achieved by via membrane separation or pressure swing absorption (PSA) or the like in the hydrogen separation unit 139.

Figure 2:
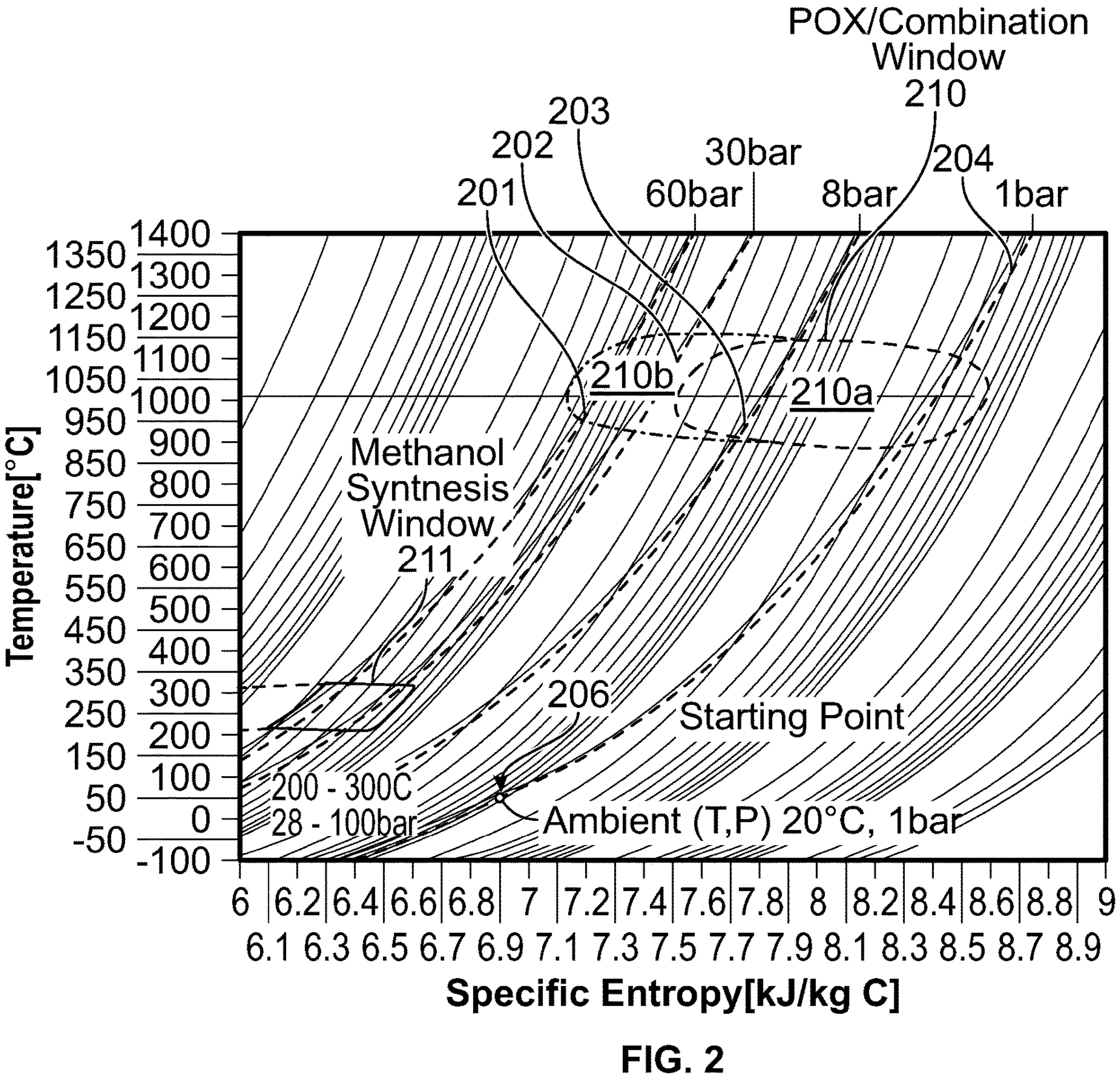
FIG. 2 is a T-S diagram of embodiments of the thermodynamic state points for converting waste, e.g., flare gas to syngas to value added products using an embodiment of an air-breathing process in accordance with the present inventions.

Turning to FIG. 2 there is shown a temperature-entropy (T-S) diagram for the general operation and thermodynamics for the operation of systems of the type shown in FIG. 1. The overall conversion process from waste gas, e.g., flare gas, to useful product, e.g., methanol, is described using the T-S diagram of FIG. 2. This diagram uses the properties of air, in an air standard approximation of the process. FIG. 2 outlines the general solutions and operation of systems such as shown in FIG. 1 from the point of thermodynamics, temperature and pressure. The diagram shows the starting point of the process at ambient conditions, the high temperature and the pressure conditions for rich, partial oxidation, in the reformer, and for high pressure lower temperature reactions for the synthesis of methanol. Thus, there is shown temperature vs entropy dashed line 201 for 60 bar pressure, dashed line 202 for 30 bar pressure, dashed line 203 for 8 bar pressure, and dashed line 204 for 1 bar pressure. (1 atmosphere is equivalent to 1.013 bar.) The temperature and pressure for the incoming air (e.g., FIG. 1, 110) and the waste gas (e.g., flare gas) is at point 206 (FIG. 2). The operating conditions for the reformer stage (e.g., FIG. 1, 101) is shown in zone 210 (FIG. 2). Zone 210 has temperatures above at and above 900° C. Zone 210 has two sub-zones, 210*a*, 210*b*. Sub-zone 210*a* is a lower pressure zone (from less than 1 bar to about 25 bar). Sub-zone 210*b* is a higher-pressure zone (from about 20 bar to about 100 bar), and in particular, a high pressure zone for rich, partial oxidation conditions in the reformer (e.g., FIG. 1, 114), which are the preferred condictiones for the embodiments of the present inventions. The optimum operation for the synthesis stage (e.g., FIG. 1, 131) is shown in zone 211 for methanal synthesis. The zone 211 is in a temperature of 200-300° C. and a pressure of about 20 bar to 100 bar. A preferred zone for methanol production is 200-300° C. and a pressure of 30-100 bar.

Thus, FIG. 2 is a graphic representation of conditions that may generally be used in a system to provide for the conversion of flare gas to an end product, in this case methanol, and to preferably do so with a neutral (i.e., provides all energy needed to operate the system and process, or positive, provides excess energy) energy balance. The Specific Entropy axis (x axis) is in units of kJ/kg C, and describes the entropy per unit mass of air. This type of diagram is a convenient way to show physical processes, such as compression and expansion (nearly vertical lines between pressure levels, and heat exchange (usually at near constant pressure). Ideal compression or expansion is isentropic, meaning no change in entropy, between two pressure levels. Compression with real equipment is non-isentropic as indicated by non-vertical lines. The Temperature axis (y axis) is in degrees C. and describes the fluid temperature, assumed to have properties similar to air. The relationship between temperature and lines of constant pressure are governed by the physical properties of the fluid. One of the benefits of the T-S diagram is that is allows a visual representation of the physical processes and the relationship between components.

The partial oxidation window 210 defines a region of temperature and pressure where the key partial-oxidation (POX) reactions take place to produce syngas. The region defines the reaction conditions that lead to reaction timescales that are commensurate with the combustion residence in reformers (e.g., a gas turbine, typically 5-50 ms). In general the POX reaction happens at much higher temperatures than that downstream synthesis (e.g., methanol) reactions, which means that the temperature needs to be reduced in a heat exchanger prior to the methanol reactor.

The methanol synthesis window 211 defines the region of temperature and pressure where the methanol synthesis reactions take place. The region defines the reaction conditions that lead to reasonable equilibrium conversion for this equilibrium-limited reaction. For this exothermic process, lower temperatures are favored for equilibrium conversion but are constrained on the low end by ensuring sufficient catalyst activity. Higher pressures yield higher equilibrium concentrations due to the net decrease in moles in the reaction but require the cost of compression and design for high pressure. While figure specifically shows a methanol synthesis window, it is understood that other possible downstream synthesis reactions, e.g. Fischer-Tropsch synthesis, require similar conditions.

In embodiments, the present systems, can be a mobile system that is contained in a shipping container frame that would fit on a single semi-truck trailer, length about 40 feet to about 60 feet, width about 6 feet to about 10 feet, and height of about 7 feet to about 15 feet. The system may also be in one, two or more separate shipping containers or open skid frames, which are then assembled into a flare gas recovery system at the location of the flare gas, e.g., an oil field, an oil well, an off-shore platform, or a floating production storage and offloading (FPSO) vessel.

In embodiments these mobile systems they are sized and configure to processes from flare gas flows of from about 250,000 scfd (standard cubic feet per day) to 30,000,000 scfd, from about 400,000 scfd to 30,000,000 scfd, from about 500,000 scfd to about 20,000,000 scfd, from about 600,000 scfd to about 15,000,000 scfd, from about 700,000 scfd to about 10,000,000 scfd, from about 1,000,000 scfd to about 25,000,000 scfd, greater than about 250,000 scfd, greater than about 500,000 scfd, greater than about 750,000 scfd, less than 10,000,000 scfd, less than 5,000,000 scfd, and less than 1,000,000 scfd, and larger and smaller flows. It further is contemplated that one, two or more of these mobile systems can be placed at a location associated with flare gas, such as an oil field, having a large number of wells, and the flare gas can be piped from several wells to these mobile systems. Thus, providing complete coverage, i.e., capture and recycling of all of the flare gas produced from the oil field.

Embodiments of the present inventions are useful in small-scale plants, using one or a plurality of syngas engines, targeting 600,000 scfd (standard cubic feet per day) of inlet gas. The size of such a plant could vary from 80,000 scfd to 3,000,000 scfd, or 20,000 scfd to 100,000 scfd.

Embodiments of the present inventions can be incorporated into one or more modular, interconnected skids or containers that are built at a central fabricator shop location and then installed at a field location. A small number of modules comprise the system and when connected at site they form an integrated system. The modular nature of the assembly enables application to remote locations under a range of inlet gas feed volumes, with a minimum of field labor.

In general, embodiments of these present systems and processes provide low carbon reprocessing of flare gas, and are preferably carbon neutral-to-negative and energy positive. In this manner embodiments of the present systems and processes capture the flare gas and convert the flare gas to an end product (e.g., methanol, ethanol, etc.) while generating sufficient energy (mechanical, electrical and both) to operate the system. In making the end product, the system is essentially carbon neutral-to-negative due to the combination of two effects: (1) Instead of being released as $CO_2$ and methane slippage, carbon from the flare gas is sequestered in the methanol thus displacing the flare gas emissions, and (2) instead of producing methanol by conventional means from natural gas or coal, that methanol is displaced by methanol produced from flare gas.

Thus, in embodiments the system and the process to produce an end product (e.g., methanol) provide a net negative CO2e for the process and the making of the end product. (As used in this specification CO2e and $CO_2$e are synonymous.) Thus, in preferred embodiments the process and resultant end product (e.g., methanol) has from about −40 kg CO2e to −130 kg CO2e, less than −20 kg CO2e, less than −40 kg CO2e, less than −60 kg CO2e, less than −100 kg CO2e and less than −130 kg CO2e per kg of downstream product (e.g, liquid methanol). It should be noted that the typical CO2e for methanol produced from natural gas is 2.1 kg CO2e per kg methanol (based on 45 kg CO2e per MMBTU methanol, 1,040 btu/scf natural gas, and 0.8 kg natural gas per $m^3$). CO2e (carbon dioxide equivalent) is based on a 20-year time horizon global warming potential for methane, based on the IPCC AR5 estimate for methane, and is 85× the global warming potential of $CO_2$.

Figure 23:
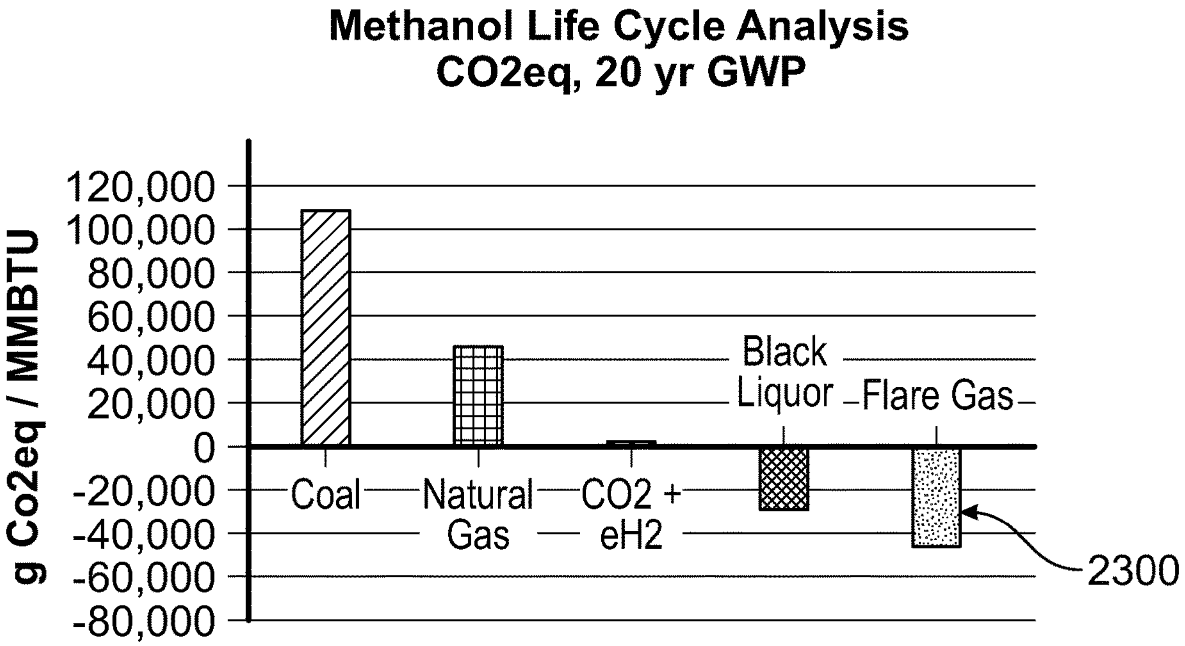
FIG. 23 is a chart comparing the CO2e for embodiments of methanol in accordance with the present inventions compared to methanol obtained from convention methods.

Thus, turning to FIG. 23 there is shown a graph showing the significant improvement, from among other things, an CO2e (and GWP) perspective, compared to conventional sources for methanol (coal, natural gas or $CO_2$+$H_2$ or black liquor). FIG. 23 shows the significant reduction in CO2e for the present inventions 2300, which methanol is obtained using the present systems and processes to convert flare gas into syngas into methanol.

More preferably, these reformers, the synthesis units and both can also produce sufficient energy to have excess energy available to operate other devices or for other purposes, e.g., oil field operations, computers having high electrical needs for processing complex algorithms, charging electric vehicles, battery storage, etc.

More preferably the control system (and sub-systems if any) operate the entire mobile system and processes. The mobile systems are configured for real time or near real time monitoring and control from a remote location, or on site.

In embodiments, these systems also have monitory and metering devices to monitor and control and memory devices to record the amount of flare gas processed, the amount of product produced and the amount, if any, of $CO_2$ produced. This information will be recorded in a secure manner for use or transmission to support carbon capture credits, or other regulatory or private equity or exchange transaction relating to $CO_2$.

More preferably the control system (and sub-systems if any) operate the entire mobile system and processes. The mobile systems are configured for real time or near real time monitoring and control from a remote location, or on site.

A block-chain based record of the carbon captured or carbon offset measurement will improve the quality of the measurement system through networked, secure record keeping. A blockchain-based carbon credit may then be sold as part of a cryptocurrency or other verifiable token in a voluntary carbon market as a carbon offset.

Reciprocating Engine Based Reformers—Generally

Embodiments of the present inventions have a reciprocating engine and methods of operating those engines to handle the variable combustion properties of the waste gas, e.g., flare gas, sources. Thus, and generally, in some embodiments the reformer 114 of FIG. 1 is a reciprocating engine. One of the reasons that these gases are non-economic is that the waste gas, e.g., flare gas, composition is highly variable. A consequence of composition variation is the resulting effect on combustion properties such as: heating value, cetane number (delay in time of ignition of fuel), and octane number (resistance to pre-ignition due to compression). These variations can occur from source-to-source, from day-to-day at the same source (transients), from season-to-season (particularly bio-gases), and over time as the source ages.

Conventional air-breathing reciprocating engines typically are designed to operate using fuels with a narrow fuel specification. For example, the compression ratio of automotive gasoline engines is selected for the quality of fuel used. The "regular' gasoline in the United States has an octane rating of 86-87. A higher performance (e.g., higher compression ratio) engine may require premium gasoline with octane rating of 91-94.

Embodiment of the present inventions use a commercial reciprocating engine (e.g., off the shelf engine) as the reformer to produce a reprocessed gas, e.g., syngas, by operating the reciprocating engine at rich conditions with high fuel-to-air ratio (equivalence ratio in the range 1.5 to 2.5). To allow the engine to operate off-design from its intended design point, and to operate satisfactorily using fuel that varies over a wide range of octane and cetane numbers, embodiments modify the operating engine parameters including compression ratio, inlet manifold air temperature, inlet manifold air pressure, and engine speed. These modifications apply to both compression ignition engines (diesel cycle) and spark ignition engines (otto cycle). For spark ignition engines, the spark timing can also be used to adapt the engine operation to fuel variation.

In embodiment of a modular system, the system and method utilize a nominally air-breathing engine that is operated under rich conditions to produce a reprocessed gas, e.g., syngas, from a waste gas, e.g., flare gas, source. Variation in composition of the fuel results in variation in combustion properties that effect engine operability. In particular, impacted operability parameters include, for example:

- Engine mis-fire—inability to transition from spark discharge to propagating flame, in one or more cylinders of an engine.
- Pre-ignition—Premature combustion of the fuel-air mixture in one or more of the cylinders in an engine.
- Auto-ignition (knock)—Spontaneous ignition of the fuel-air mixture ahead of the propagating flame.
- Low combustion efficiency—high levels of unburned fuel in the exhaust, due to exhaust valve opening before combustion propagation across the cylinder volume is complete, or unburned fuel in crevice volumes and quenching on cold surfaces, or can be related to misfire.

FIGS. 20A, 20B, and 21, as well as, Tables 1 and 2, show the range of compositions for the flare gas that can be processed by embodiments of the reciprocating engine reformers, including the embodiments of the Examples, into reprocessed gas, e.g., syngas.

These mixtures and their individual constituents represent wide range of octanes, with the heavier hydrocarbons having lower octane and hence a greater tendency to pre-ignite or auto-ignite. Specific values of octane number, a key measure of mixture reactivity, are shown in Table 3. Estimated values of octane number for the lean and rich gas in FIGS. 20A and 20B are shown in Table 3.

FIG. 21 shows how the fuel energy per unit volume varies with gas composition. This variation affects, and is address by the sizing and control of the fuel delivery system.

TABLE 3

(Octane numbers of individual constituents (Octane Number (research octane number = RON))

| Constituent | Octane (research/RON) | Octane (motor/MON) | AKI (R + M)/2 |
|---|---|---|---|
| Methane | 135 | 122 | 128.5 |
| Ethane | 108 | | |
| Propane | 112 | 97 | 104.5 |
| Butane | 93 | 90 | 91.5 |
| Pentane | 61.7 | 61.9 | 61.8 |
| Lean Associated Gas (table 1) | 126 (est) | | |
| Rich Associated Gas (table 1) | 117 (est) | | |

Turning to FIG. 21 it is shown that for gaseous fuels, changes in fuel composition also influence the energy content of the fuel, as quantified by fuel heating value per unit volume (Wobbe number). This figure shows typical ranges of Wobbe number vs fuel heating value for a range of fuel compositions.

Variation in fuel properties sets up a fundamental tension in the design of a reciprocating engine system, which embodiments of the present inventions address. On one hand, high compression ratio and high inlet air temperature are beneficial for the combustion characteristics to produce syngas with desired $H_2$/CO ratio (typical range about 1.0 to about 2.0, preferably 1.5 to 2.0) with low emission of unburned fuel. On the other hand, high compression ratio and high inlet air temperature can result in pre-ignition, or autoignition of the fuel-air mixture if the fuel becomes more reactive. Conversely, if the fuel becomes less reactive, increased compression ratio or inlet air heating would be beneficial. Thus, setting a specific design point for the engine is not compatible with smooth engine operation with fuel, e.g., flare gas, that has variable combustion properties.

In embodiments, the solution to this problem is modify the engine operating properties while the engine is operating. In embodiments, a combination of modified critical operating engine parameters including:

compression ratio (effective compression ratio or geometric compression ratio)

range 8:1 to 17:1 inlet manifold air temperature, range of ambient temperature to 300 C.

inlet manifold air pressure, ambient to 5 bar.

spark timing, TDC (top dead center, e.g. zero degrees) to MBT (minimum spark advance for best torque, e.g. 30 degrees typical, 15-45 degree range)

and engine speed, 800 rpm to engine max (eg. 1800 rpm)

the range of conditions above can be applied to a two-stroke or four-stroke reciprocating engine.

In embodiments, to detect if the engine is operating correctly, in a controller, and preferably an autonomous control system, a set of sensors can be used. This autonomous control system is preferable a part of, or in control communication with, the control system for the overall system (e.g., system 100 of FIG. 1), and can be for example a sub-system, a separate controller, and preferably is also in control communication with the general control system for the overall system. These sensors can include:

Knock detection (vibration-based sensors) mounted to the block or head

Lambda sensor (sensor that infers air to fuel ratio from exhaust gas composition, typically mounted downstream of exhaust valves)

Exhaust temperature (typically thermistor or thermocouple) mounted downstream of the exhaust valves.

Intake manifold temperature or pressure.

Fuel sensors including mass flow, dew point temperature, and heating value (e.g., calorimeter).

In an embodiment, of the reciprocating engine, the fuel-air mixture is rich, preferably having an overall fuel/air equivalence ratio (ϕ or ER) greater than 1, greater than 1.5, greater than 2, greater than 3, from about 1.5 to about 4.0, about 1.1 to about 3.5, about 2 to about 4.5, and about 1.1 to about 3, and greater values.

In embodiments of the reciprocating engine reformer, it being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing engines" defined herein are understood to also include engines using air modified with the addition of water or oxygen.

The reciprocating engine produces, a reprocessed gas, e.g, syngas, (as well as heat and mechanical energy, which can be used to power and operate the entire process) which is then filtered and heat from the syngas is recovered by a heat exchanger.

The overall (general) reaction for rich fuel/air mixture to syngas in a reciprocating engine is given by the equation:

$$ØCH_4+2[O_2+3.76\ N_2]\rightarrow aCO+bH_2+cCO_2+dH_2O+7.52\ N_2$$

Where stoichiometric coefficients a, b, c and are determined by the chemical kinetics, conservation of atomic species, and the reaction conditions.

In addition to syngas minor constituents in the gas exiting the reciprocating engine include water vapor, $CO_2$, and various unburned hydrocarbons.

Gas Turbine Engine Based Reformers—Generally

Embodiments of the present systems and methods, utilizing gas turbine reformers, generally relate to systems, devices and methods to convert otherwise uneconomic hydrocarbon-based fuel, e.g., flare gas to a to value-added, easily transported products (such as, methanol, ethanol, ammonia, dimethyl-ether, F-T liquids, and other fuels or chemicals, and combination and variations of these). These embodiments in general have a flare gas (i.e., fuel) conditioning system, an air-breathing gas engine, and a conditioning assembly that conditions the syngas for storage, shipping, later processing and combinations and variations of these. The flare gas is conditioned to remove impurities and materials that could be detrimental to later processing steps. The flare gas (e.g., fuel gas for the system) is then mixed with air and ignited in an engine.

Embodiments of the present inventions have a turbine engine, e.g., air breathing gas turbine engine, as the reformer to produce reprocessed gas, preferably syngas. Thus, and generally, in some embodiments the reformer 114 of FIG. 1 is a gas turbine engine. In some embodiments gas turbines are preferred under certain circumstances (such as larger magnitudes of wellhead flows), as they provide advantages over embodiments using reciprocating engines to produce syngas. The gas turbine-based systems are suitable for larger scale gas-to liquid (e.g., flare gas to methanol) applications where there are packaging limitations, e.g., on-site footprint limitations. Embodiments of the present systems are modular and can easily and readily be positioned at difficult to access locations, locations with limited area for placement of the systems, and combinations and variations of these, where for example flare gas is generated.

Further, the gas turbine-based system has the capability to handle, e.g., receive and process to an end product, flare gases having a wide and varying ranges of composition, which in some embodiments can provide an advantage over a reciprocating engine. Changes in flare gas (i.e., fuel) composition can change ignition characteristics and burning times. For a reciprocating engine with fixed compression ratio, such changes should be addressed to avoid the potential of damaging engine knocking or misfires and exhaust value over-heating, as well as other problems.

Gas turbine combustion systems can burn a wide variety of liquid and gaseous fuels, preferably provided they are suitably free of contaminants that would lead to corrosion or deposits. Also, the flame is continuously burning in a gas turbine, unlike reciprocating engines where ignition must occur in each cylinder during each power stroke. Moreover, gas turbines can operate continuously for about 8,000 hrs (up to 24,000 hrs for some models, and potentially longer), without shutdown, and extended intervals greater than 24,000 hrs for major overhaul. With more moving parts and more wear surfaces, reciprocating engines must typically be shutdown to replace lubricating fluids at about 2,000 to about 4,000 hours intervals, and major overhaul at about 8,000-12,000 hours.

One of the many advantages that a gas turbine system may have over a reciprocating engine system, in some embodiments, is that the flare gas components can vary and gas turbine performance is not affected. In general, flare gasses having compositions as set out in FIGS. 20A, 20B, 21, as well as, Tables 1 and 2, can be processed by the embodiments of gas turbine systems of the present inventions, including the Examples. However, some factors that still may play a part in performance of gas turbine system include: 1) margin to the dew point, i.e., superheat, of the flare gas of 10° C., ensuring gaseous inlet fuel, 2) keeping the heating value of the overall fuel is >400 BTU/scf., and 3) corrosive elements, such as Vanadium, are filtered out prior to combustion.

Embodiments of the present systems and methods, utilizing gas turbine reformers, generally relate to systems, devices and methods to convert otherwise uneconomic hydrocarbon-based fuel, e.g., flare gas to a to value-added, easily transported products (such as, methanol, ethanol, ammonia, dimethyl-ether, F-T liquids, and other fuels or chemicals, and combination and variations of these). These embodiments in general have a flare gas (i.e., fuel) conditioning system, an air-breathing gas turbine, and a conditioning assembly that conditions the syngas for storage, shipping, later processing and combinations and variations of these. The flare gas is conditioned to remove impurities and materials that could be detrimental to later processing steps. The flare gas is then compressed to a pressure of about 8 to about 35 bar (typically corresponding to about 1.2× the pressure ratio of the gas turbine air compressor), about 5 to about 40 bar, at least about 10 bar, at least about 20 bar and at least about 1.1× the pressure ratio of the gas turbine air compressor, from about 1.05× to about 1.8× the pressure ratio of the gas turbine air compressor and greater and smaller values. The compressed flare gas (i.e., fuel for the system) is then mixed with air and ignited in a gas turbine. The pressure of the air when mixed with the compressed fuel gas, preferably will be the same as the fuel gas. The temperature of the compressor discharge air is a known function of the inlet air temperature, the compression ratio, and the compressor efficiency, and the temperature of the compressed discharge air should be about 150° C. to about 600° C., about 150° C. to about 500° C., about 200° C. to about 400° C., greater than about 150° C., greater than about 300° C., and greater than about 500° C. The temperature of the compressed waste gas, e.g., flare gas, should be about 100° C. to about 300° C., about 150° C. to about 300° C., about 125° C. to about 200° C., greater than about 150° C., greater than about 200° C., and greater than about 250° C., and less than 350° C. and higher and lower values.

Generally, for embodiments of the gas turbine reformers, the fuel-air mixture is rich, preferably having an overall fuel/air equivalence ratio ($\phi$ or ER) 0.98 or greater, greater than 1, greater than 1.5, greater than 2, greater than 3, from about 1.5 to about 4.0, about 1.1 to about 3.5, about 2 to about 4.5, and about 1.1 to about 3, and greater values.

In embodiments of the gas turbine reformers, it is understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing engines" defined herein are understood to also include engines using air modified with the addition of water or oxygen.

Preferably the gas turbines are smaller sized units, from about 200 kW to about 5000 kW, from about 200 kW to about 2000 kW, and less than 6000 kW, less than 5000 kW, less than 3000 kW and less than 2000 kW, although larger and smaller sizes may be used.

The gas turbine produces syngas, (as well as heat and mechanical energy, which can be used to power and operate the entire process) which is then filtered and heat from the syngas is recovered by a heat exchanger.

The overall (general) reaction for rich fuel/air mixture to syngas in a gas turbine is given by the equation:

$$ØCH_4+2[O_2+3.76\ N_2]\rightarrow aCO+bH_2+cCO_2+dH_2O+7.52\ N_2$$

Where stoichiometric coefficients a, b, c and are determined by the chemical kinetics, conservation of atomic species, and the reaction conditions.

In embodiments of the systems initiation of combustion occurs at near ambient conditions in the combustion chamber of gas turbine when the shaft of the turbine is turned at low cranking speed.

An additional feature, for an embodiment of the combustion chamber is to stage the fuel addition to extend the rich limit of combustion. For example, in a forward part of the combustion chamber part of the fuel is mixed with air to produce a flame with very stable combustion (for example near stochiometric conditions). Downstream of that stable flame zone additional fuel is added to meet the overall equivalence ratio required to achieve the $H_2/CO$ ratio of the downstream process.

In addition to syngas minor constituents in the gas exiting the gas turbine include water vapor, $CO_2$, and various unburned hydrocarbons.

In general, embodiments of a partial-oxidation gas turbine comprise a compressor, combustor, and turbine. The compressor takes ambient air and raises the pressure. The compressor discharge air is mixed with excess fuel and partially oxidized in the combustor. The discharge of the combustor is expanded through the turbine to ambient conditions. The work produced by the turbine typically exceeds the work required to drive the compressor. A conceptual drawing of one embodiment of the partial-is shown in FIG. 7.

Figure 7:
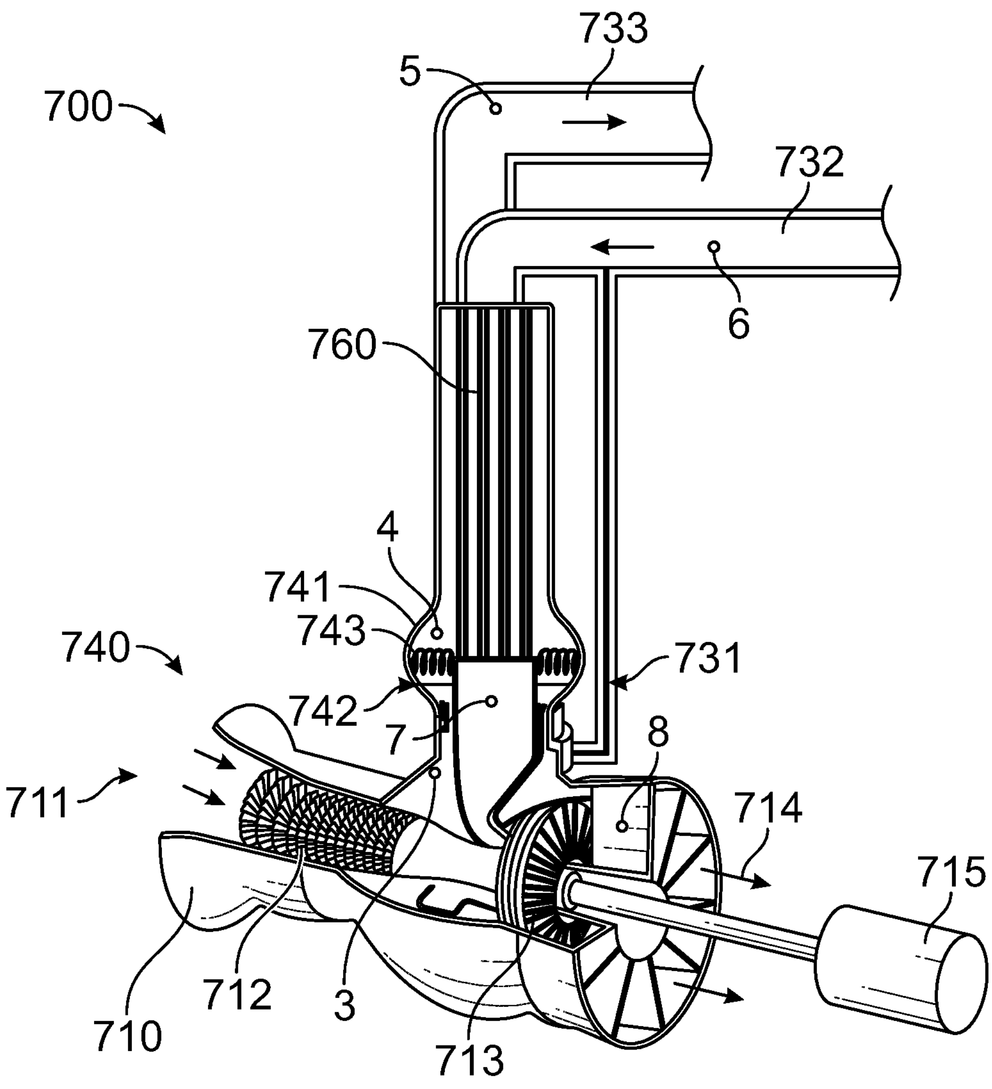
FIG. 7 is a partial cutaway perspective view of an embodiment of a gas turbine for use in an embodiment of a reformer stage in accordance with the present inventions.

Thus, turning to FIG. 7 the reformer gas turbine assembly 700. The gas turbine 700 has a gas turbine engine 710, (e.g., air breathing turbine engine) that has an air intake 711, a compressor 712, a turbine 713, and an exhaust flow 714. The gas turbine 710 has a shaft configured for rotation with the turbine and compressor that is connected to a motor or generator 715. The gas turbine 700 has two part or two stage combustor 740, that provides for partial oxidation combustion of the flare gas. The two stage combustor 740 has a first stage, which is a rich partial oxidation combustor 741 and a second stage, which is the gas turbine 710. The flare gas is injected at 742 and is partially combusted in reaction zone 743 of first stage combustor 741. The product of this partial combustion is directed into the gas turbine 710 where further combustion, with the incoming air from intake 711 occurs to provide syngas. Syngas is produced in 743 (inside the combustion chamber), flows up and through heat exchanger 760 and out line 733 to the synthesis stage. The post-reaction synthesis gas returns through line 732 from the synthesis unit. This flow is heated by the syngas produced in 743, and expanded through the turbine in 713. A portion of the flow of line 732 is unheated and flows through bypass line 731. This gas may have a high $N_2$ gas flow for use on seals and secondary cavities.

The numbers in circles in FIG. 7 relate to a location for a process condition, e.g., state points, discussed with respect to T-S diagrams relating to specific Examples and as discussed in the Examples.

EXAMPLES

The following examples are provided to illustrate various embodiments of the present waste gas conversion processes and systems. These examples are provided to illustrate various embodiments of the present gas-to-liquid conversion processes and systems. These examples are for illustrative purposes, may be prophetic, and should not be viewed as, and do not otherwise limit the scope of the present inventions.

The embodiments of these Examples 1 to 54 can have or utilize one or more of the embodiments, processes, methods, features, functions, parameters, components, or systems disclose and taught in the "Systems and Processes—Generally", "Reciprocating Engine Based Reformers—Generally", and "Gas Turbine Engine Based Reformers—Generally" sections of this specification, and combinations and variations of each of these; as well as, one or more of the embodiments, processes, methods, features, functions, parameters, components, or systems provided in one or more of the other Examples and other embodiments taught and disclosed in this specification.

Example 1

A system and process to convert otherwise uneconomic hydrocarbon-based fuel such as flare gas to value-added, easily transported products (such as methanol, ethanol, ammonia, dimethyl-ether, F-T liquids, and other fuels or chemicals) using an autonomous, modular system comprising the following elements: (1) a fuel conditioning system to meet requirements of downstream components; (2) an air-breathing gas turbine, modified to operate a rich, partial-oxidation reformer, to produce a syngas mixture with a $H_2/CO$ ratio suitable for synthesis of liquids; (3) a combination of integrated heat exchangers, compression system components, and heat exchangers to prepare the syngas for the downstream synthesis reactors; and (4) a downstream synthesis reactor system to produce useful liquid hydrocarbon products.

Example 2

A system and process to convert otherwise uneconomic hydrocarbon-based fuel such as flare gas to value-added, easily transported products (such as methanol, ethanol, ammonia, dimethyl-ether, F-T liquids, and other fuels or chemicals) using an autonomous, modular system comprising the following elements: (1) a fuel conditioning system to meet requirements of downstream components; (2) an air-breathing gas turbine, modified to operate a rich, partial-oxidation reformer, to produce a syngas mixture with a $H_2/CO$ ratio suitable for synthesis of liquids; (3) a combination of integrated heat exchangers, compression system components, and heat exchangers to prepare the syngas for the downstream synthesis reactors; (4) a downstream synthesis reactor system to produce useful liquid hydrocarbon products; and, (5) a hydrogen recycle loop to improve overall system process performance.

Example 3

The systems and process of Examples 1 and 2 can also have one, or more, or all of the following additional features: (6) optional substantially oxygen-free gas recirculation loop to cool and protect downstream components of the combustor, such as seals, bearings, and secondary cavities; (7) optional $O_2$ enrichment of the inlet stream to the gas turbine via membrane separation or partial air separation unit; (8) a recuperator heat exchanger (from (3)) and a turbo expander to recover energy from the high pressure exhaust gas from the downstream synthesis reactor; (9) integration of a closed-loop operating system with custom instrumentation; (10) a cloud-based remote monitoring system, including AI-trained anomaly detection for dynamic preventative maintenance and operations control; (11) optional offtake pathways to utilize byproducts, such as nitrogen, water, and $CO_2$ for reinjection, well recompletions, or other purposes; (12) optional water (or steam) injection into the rich combustor to improve $H_2/CO$ ratio and reduce carbon build-up on surfaces within the combustor and turbine.

Example 4

A gas-to-liquid system takes uneconomic hydrocarbon-based fuels, e.g., flare gas, at a well-head and remote locations that are primarily gaseous hydrocarbons and convert them to a more valuable easily condensable or liquid compounds, such as methanol. One source of source fuel could be associated gas or flare gas, which is produced as a byproduct at oil wells. Another source could be biogas from landfill or anaerobic digesters.

A small-scale plant, targeting 3,000,000 scfd (standard cubic feet per day) of inlet gas. The size of such a plant could vary from 300,000 scfd to 15,000,000 scfd. The plant is incorporated into one or more modular, interconnected skids or containers that are built at a central fabricator shop location and then installed at a field location. A small number of modules comprise the system and when connected at site they form an integrated system. The modular nature of the assembly enables application to remote locations under a range of inlet gas feed volumes, with a minimum of field labor. The modular nature further improves flexibility to deploy or redeploy these assets, reduces initial capital outlay and project financial risks, allows matching of the process throughput to the flare gas supply, and reduces time-to-market by allowing module fabrication and site preparation to occur in parallel.

Example 5

Figure 3:
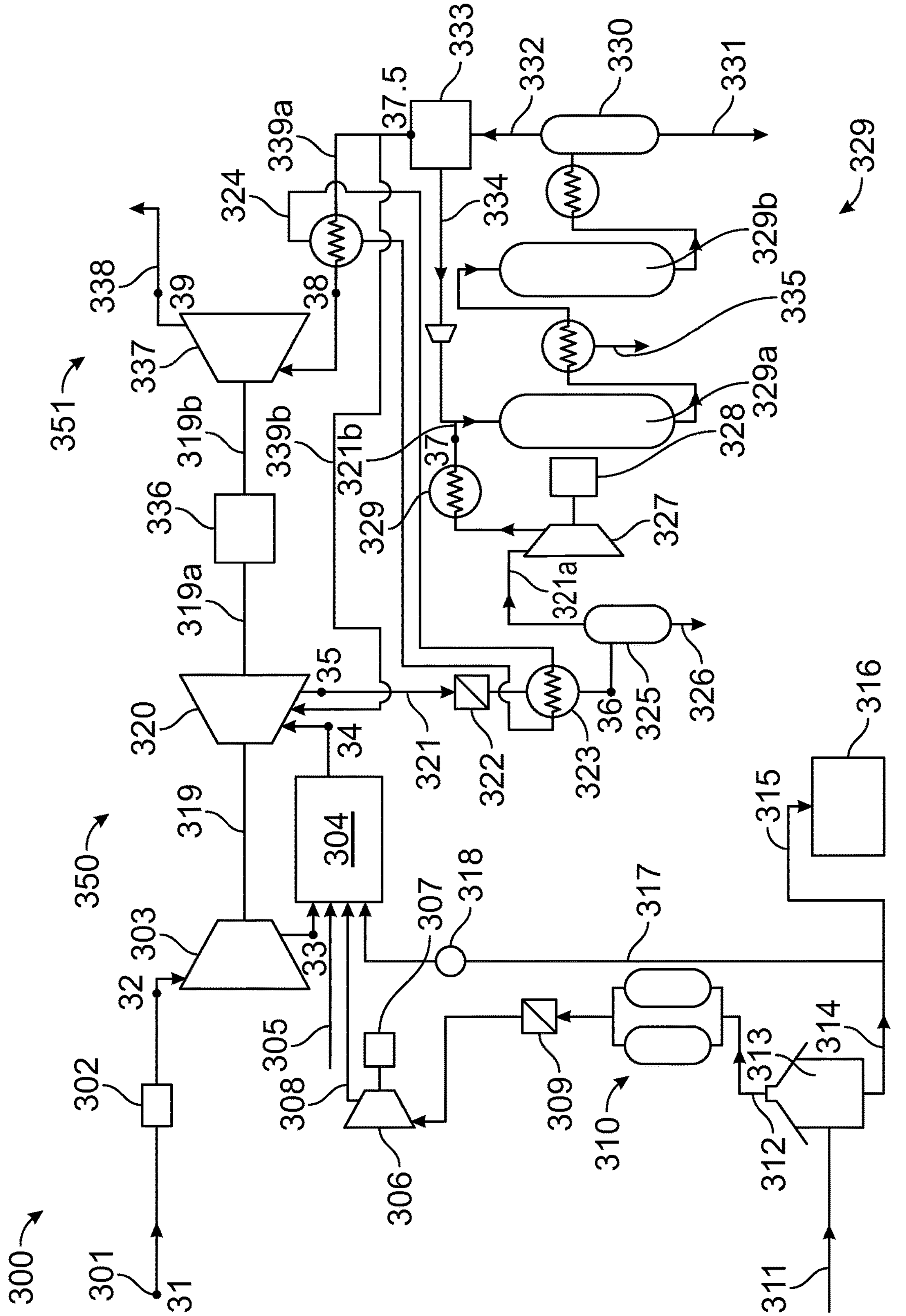
FIG. 3 is a schematic flow diagram of an embodiment of a system and process in accordance with the present inventions.
Figure 4:
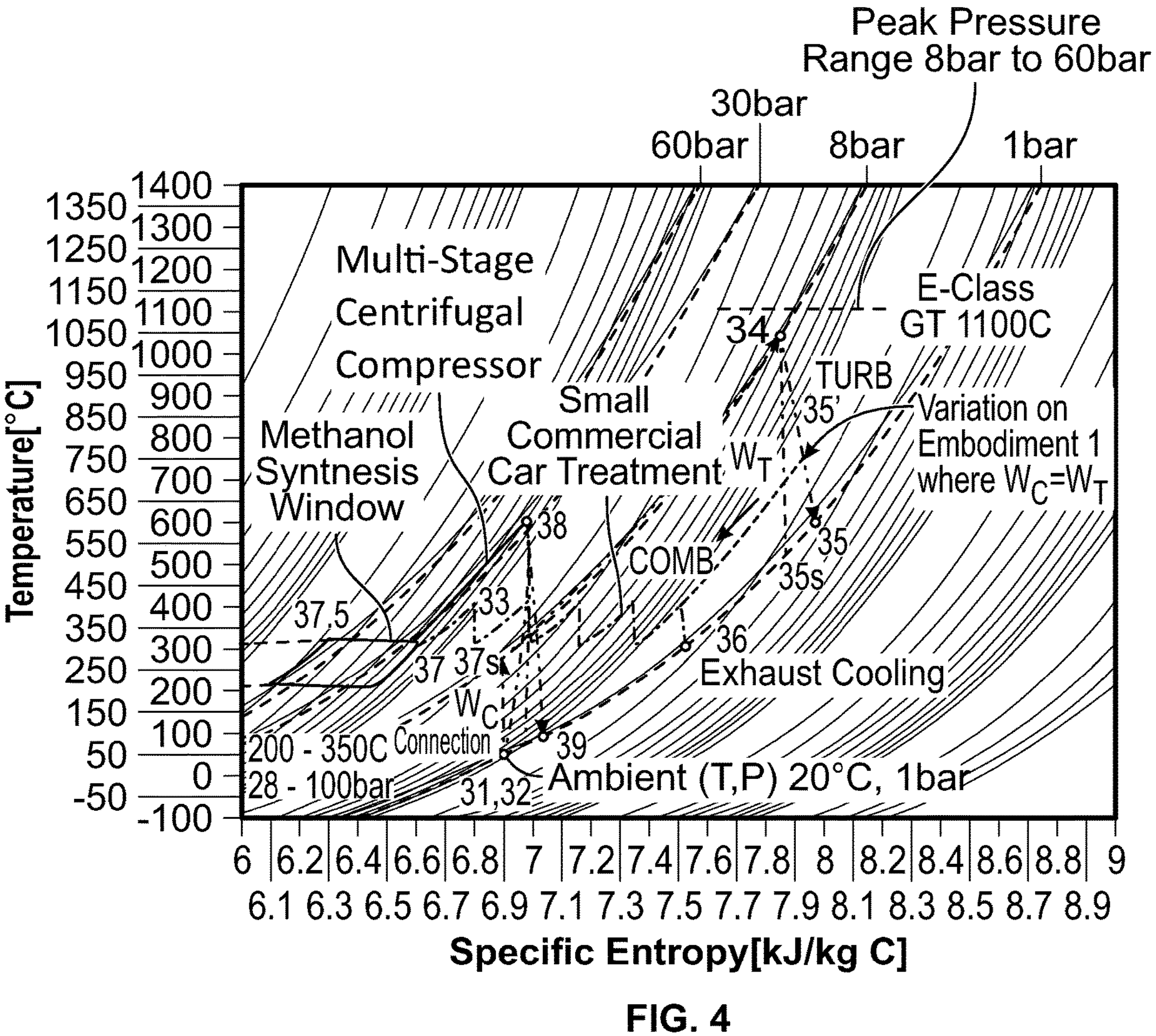
FIG. 4 is a T-S diagram showing an embodiment of a process, operating conditions and thermodynamic state points for converting flag gas to syngas to methanol, using the system of FIG. 3 in accordance with the present inventions.

Turning to FIG. 3 there is shown a schematic of a system and method, and preferably a modular plant and processes, for the recovery and conversion of flare gas into methane. FIG. 4 is a T-S graph showing a preferred operating conditions and thermodynamic state points of the process that can be used for the operation of the embodiment of FIG. 3. The reference points (numbers—31, 32, 33, 34, 35, 36, 37, 37.5, 38, 39, in FIG. 3) correspond to process conditions, i.e., state points, at those locations in the system of FIG. 3, and those process conditions are shown by corresponding reference points in FIG. 4. The prime reference points in FIG. 4 (e.g., 35', 36') indicate expected cycle points considering efficiency of the components. Reference point 7.5 indicates the discharge of the downstream synthesis process. And, reference points $\mathbf{33}_s$ and $\mathbf{35}_s$ indicates idealized isentropic processes (vertical process lines) conditions. The starting specific entropy for this process is at points 31, 32 (6.9 kJ/kg° C.) and the final specific entropy point for this process is 39 (7.04 kJ/kg° C.). Thus, the difference between the start and final specific entropy is 0.14 kJ/kg° C.).

Turning to FIG. 3 there is shown a combustion chamber system 300 for converting flared gas from a flare gas source (e.g., oil well, gas well, land fill, agriculture plant, waste water treatment plant, etc.) into methanol. The system 300 has a reformer section or stage 350 and a synthesis section or stage 351.

The system 300 has an air intake 301 that flows the air to a filter 302, where dust, sand, particulates, etc., are removed from the air, after which the air flows to compressor 303, where it is compressed. The compressed air leaves compressor 303 and flows to an air breathing combustion box 304, where the flare gas is partially oxidized. The combustion box 304 can be a single stage, two stages, or more.

Flare gas (e.g., raw flare gas) from a flare gas source (e.g., an oil or gas well or field) enters system 300 through line 311 and flows to a separator 313, where liquids and gas are separated. The separated liquids, including liquid hydrocarbons having 3 or more carbon atoms, and flow from the separator 313 through line 314. These liquids can flow through line 315 to a storage tank 316. The separated liquids can flow through line 317, and are pumped, by pump 318 into the combustion box 304.

The gases components of the flare gas exit the separator 313 via line 312 and flow to a gas conditioning unit 310. Gas conditioning unit 310 can remove harmful materials to the process, including $H_2S$ (hydrogen sulfide), as well as, any materials that would harm or poison any catalysts that are used in the system. The conditioned flare gas leaves conditioning unit 310 and flows to gas filter 309, where further harmful or detrimental materials are removed, e.g., iron sulfides, sulfur, as well as any materials that would harm or poison any catalysts that are used in the system. The conditioned and filtered flare gas leaves filter 309 and flows into gas compressor 306, which is driven by motor 307. The compressor 306, compresses the flare gas to a predetermined pressure and temperature as taught and disclosed in this specification and for example shown in FIG. 4, and flows this flare gas into combustion box 304. Water, steam, or oxygen may also be added to the combustion box 304 via line 305.

The compressed flare gas can be at a pressure of about 3 to about 60 bar, about 8 to about 35 bar (typically corresponding to about 1.2× the pressure ratio of the gas turbine air compressor), about 5 to about 40 bar, at least about 10 bar, at least about 20 bar, and at least about 1.1× the pressure ratio of the air compressor, from about 1.05× to about 1.8× the pressure ratio of the gas air compressor and greater and smaller values. The compressed flare gas (i.e., fuel for the system 300) is then mixed with the compressed air and ignited in the combustion box 304, where it is partially oxidized. The pressure of the air when mixed with the compressed flare gas, can be any of the above ranges of pressure for the flare gas; and preferably will be the same pressure as the flare gas. In the embodiment of the operation of the process as shown in FIG. 4, the pressure of the flare gas and air is 8 bar, when they are introduced into the combustion box 304 for partial oxidation to form syngas.

The syngas exits the combustion box 304 and flows into turbine 320, where its pressure is reduced (see, e.g., state points 34 (preferred 8 bar) and 35 (preferred 1 bar)). The turbine 320 is connect to compressor 303 by rotation shaft 329, where it turns compressor 303. The turbine 320 is connect to motor or generator 336 by rotating shaft 319*a*. Rotating shaft 319*b* contexts turbine 337 with motor or generator 336.

The syngas leaves turbine 320 via line 321 and flows into filter 322 where particulates, e.g., soot, are removed. The syngas then flows into heat exchange 323 where the temperature is lowered to the methanol synthesis window, preferably 200° C.-300° C. (see, e.g., FIG. 4). The heat exchanger 323 is part of a heat exchanger loop 324. The syngas then flows from heater exchanger 323 to a water separation unit 325. Water is removed from the water separation unit 325 via line 326. The syngas leaves unit 325 and flows via line 321*a* into compressor 327, which is driven by motor 328. The compressor compresses the syngas to about 30-100 bar. For the preferred operation shown in FIGS. 3 and 4, by state points 36 (1 bar) and 37 (30 bar).

The syngas leaves compressor 327 and flows to a heat exchanger 329, where the temperature is maintained for the methanol synthesis window, and flows from the heat exchanger 329 via line 321*b* to the synthesis unit 329. The synthesis unit has two reactors 329*a* and 329*b*. It is noted that a single stage or reactor can be used, and that more than two stages or reactors can be used. The synthesis unit 329 has a line 335 for discharging water, methanol or both. The synthesis unit 329 converts the syngas to methanol, which then flows to hold and separation unit 330. Unit 330 separates the liquid methanol from any remaining gas. The methanol is discharged through line 331 for storage, further processing, use, shipping, etc. The gases flow through line 332 to hydrogen separator unit 333. Hydrogen leaves separation unit 333 via line 334 and flows back to the synthesis unit 329, where it is used to adjust the $H_2$/CO ratio of the syngas. The remaining gases, e.g., low $H_2$ concentration stream, from the unit 333, flow through line 339*b* for injection into the turbine 320; and flow through line 339*a* to turbine 337 and then to exhaust line 338.

This arrangement of components in this example is an efficient way to achieve the particular state points of the process that produce methanol in an economic and effective manner. These state points include: 1) starting at ambient conditions, 2) raising temperature and pressure to achieve rich partial oxidation, and 3) cooling and pressurizing to achieve downstream synthesis. The carbon intensity and energy intensity of the process can be managed by tuning the cycle points to just match the POX and synthesis windows. Furthermore, the cycle points can be tuned to minimize the energy requirements for midstream and downstream separations processes.

The operation of the system of FIG. 3 under the embodiment of the state conditions of FIG. 4 revolves around a rich-burn reformer and a synthesis reactor. Unlike a traditional gas turbines and reciprocating engines, the combustor 304 runs at rich conditions, up to equivalence ratio of about 4 so the fuel, i.e., flare gas, experiences rich partial oxidation (POX). The system 300 has fuel, i.e., flare gas, conditioning system, heat exchangers, compressors, and turbines. The fuel conditioning system separates liquids from gases in the feed stream and removes compounds that can damage the gas turbine or synthesis reactor. The heat exchangers and compressors take the syngas mixture at the exit of the gas turbine and adjust the temperature and pressure to deliver the target conditions for the synthesis reactor. Within the synthesis sub-system is an optional $H_2$ recycle loop. The gas at the exit of the synthesis reactor is heated in a recuperating (e.g., counter-flow) heat exchanger to an elevated temperature and then expanded to ambient conditions.

Example 6

The system of FIG. 3, and other embodiments of the present systems, can be operated and configured in a manner that limits expansion of the gas through the turbine 337, such that the work from the compressor 303 and turbine sections 320 is matched. In this way, the exhaust gas from line 338 is pressurized above ambient pressure and less compression work, with compressors 303, and in particular 329, is required to meet the pressure required by the downstream synthesis reactor 329, thus reducing the compression stages and equipment complexity. For example, compressor 329 can be reduced in size, work required, and even eliminated.

Example 7

Figure 5:
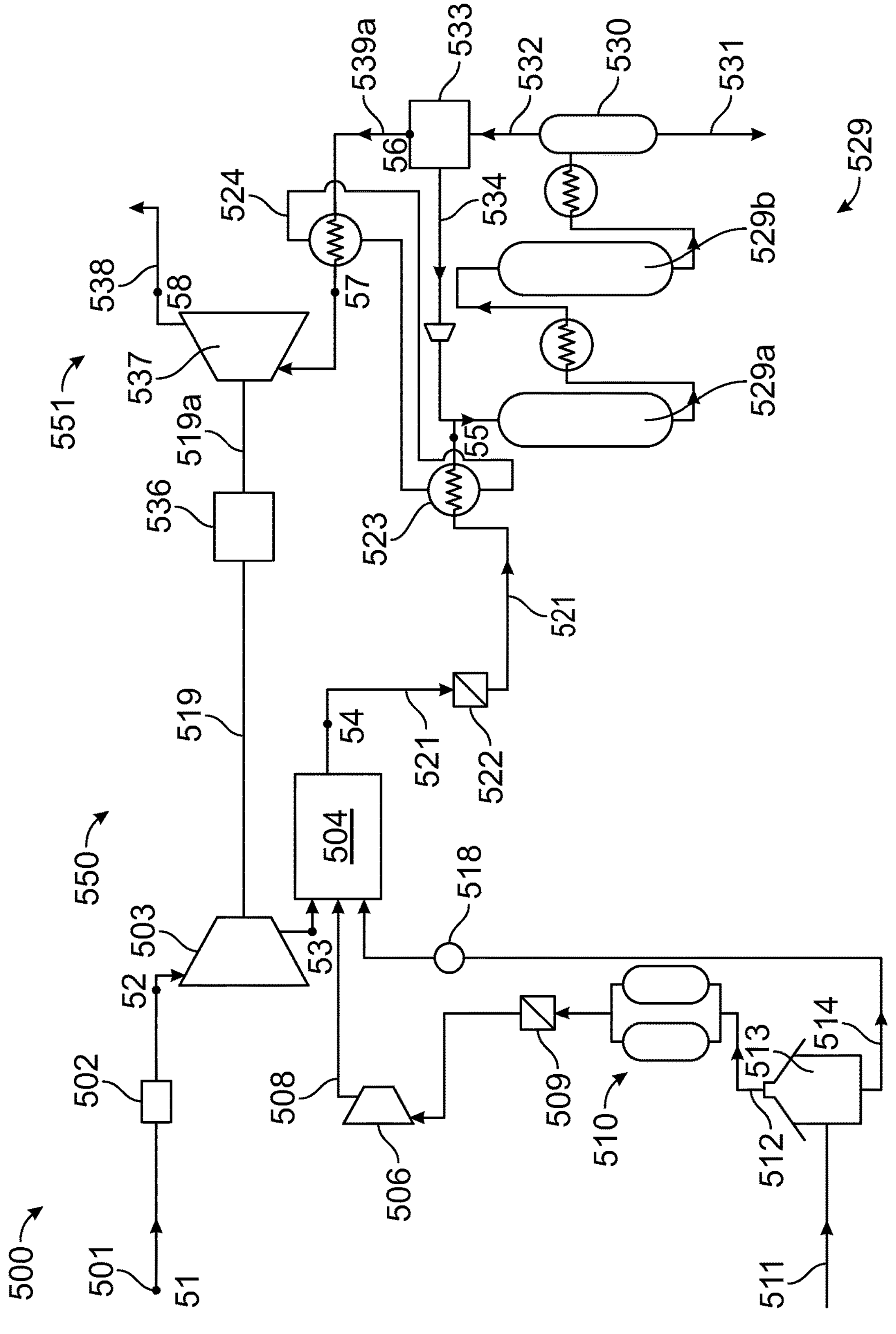
FIG. 5 is a schematic flow diagram of an embodiment of a system and process in accordance with the present inventions.
Figure 6:
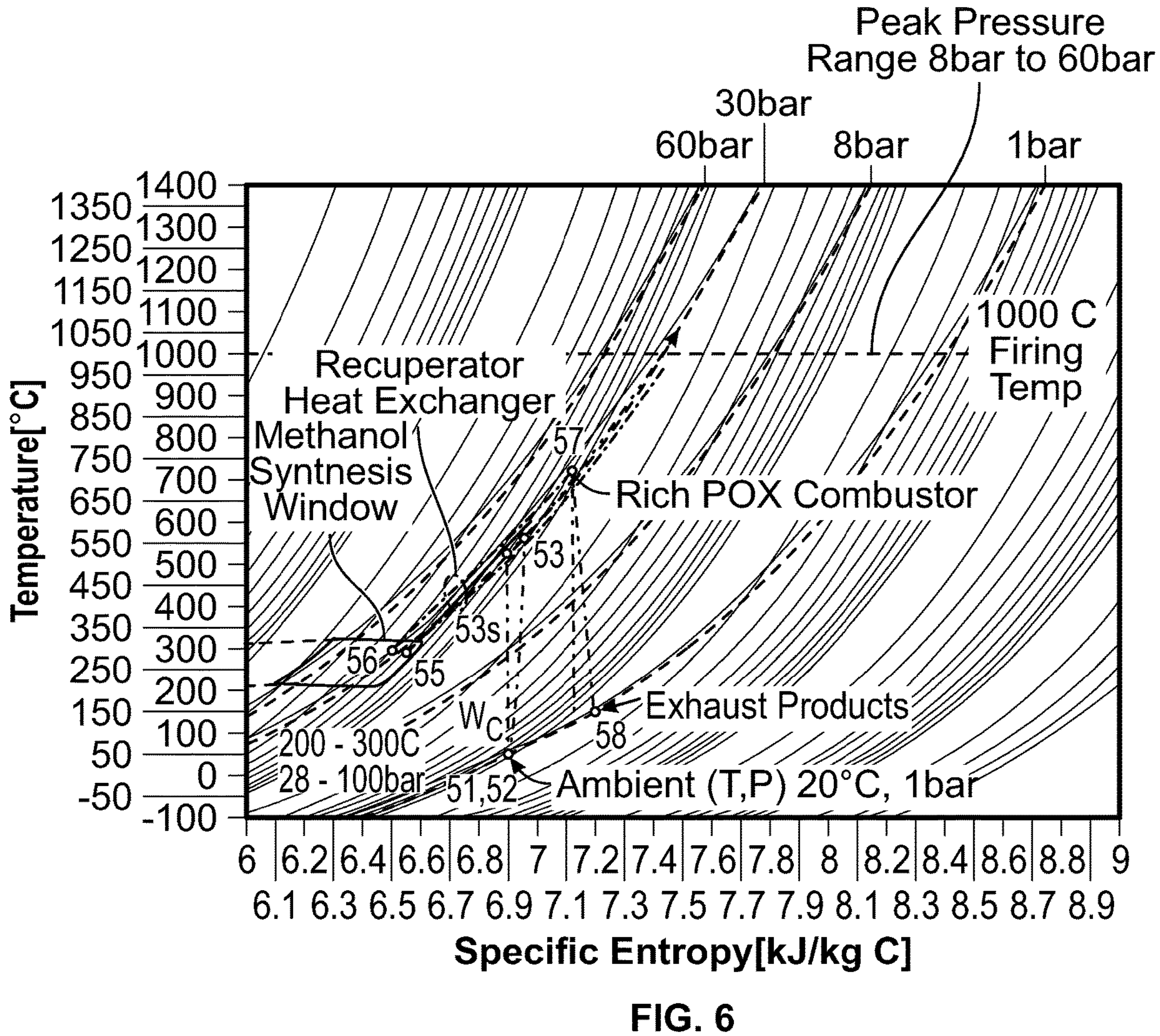
FIG. 6 is a T-S diagram showing an embodiment of a process, operating conditions and thermodynamic state points for converting flag gas to syngas to methanol, using the system of FIG. 5 in accordance with the present inventions.

Turning to FIG. 5 there is shown a schematic of a system and method, and preferably a modular plant and processes, for the recovery and conversion of flare gas into methane. FIG. 6 is a T-S graph showing a preferred operating conditions and thermodynamic state points of the process that can be used for the operation of the embodiment of FIG. 5. The reference points (numbers—51, 52, 53, 54, 55, 56, 57, 58, 59, in FIG. 5) correspond to process conditions, i.e., state points, at those locations in the system of FIG. 5, and those processes conditions are shown by corresponding reference points in FIG. 6. And, reference points 53$_s$ indicates idealized isentropic processes (vertical process lines) conditions. The starting specific entropy for this process is at points 51, 52 (6.9 kJ/kg° C.) and the final specific entropy point for this process is 58 (7.2 kJ/kg° C.). Thus, the difference between the start and final specific entropy is 0.3 kJ/kg° C.

Turning to FIG. 5 there is shown a combustion chamber system 500 for converting flared gas from a flare gas source (e.g., oil well, gas well, land fill, agriculture plant, waste water treatment plant, etc.) into methanol. The system 500 has a reformer section or stage 550 and a synthesis section or stage 551.

The system 500 has an air intake 501 that flows the air to a filter 502, where dust, sand, particulates, etc., are removed from the air, after which the air flows to compressor 503, where it is compressed. The compressed air leaves compressor 503 and flows to an air breathing combustion box 504, where the flare gas is partially oxidized. The combustion box 504 can be a single stage, two stages, or more.

Flare gas (e.g., raw flare gas) from a flare gas source (e.g., an oil or gas well or field) enters system 500 through line 511 and flows to a separator 513, where liquids and gas are separated. The separated liquids, including liquid hydrocarbons having 3 or more carbon atoms, and flow from the separator 513 through line 514. The separated liquids can flow through line 514, and are pumped, by pump 518 into the combustion box 504.

The gases components of the flare gas exit the separator 513 via line 512 and flow to a gas conditioning unit 510. Gas conditioning unit 510 can remove harmful materials to the process, including $H_2S$, as well as, any materials that would harm or poison any catalysts that are used in the system. The conditioned flare gas leases conditioning unit 510 and flows to gas filter 509, where further harmful or detrimental materials are removed, e.g., iron sulfides, sulfur, as well as any materials that would harm or poison any catalysts that are used in the system. The conditioned and filtered flare gas leaves filter 509 and flows into gas compressor 506. The compressor 506, compresses the flare gas to a predetermined pressure and temperature as disclosed and taught in this specification and for example shown in FIG. 6, and flows this flare gas into combustion box 504. Water, steam, or oxygen may also be added to the combustion box.

The compressed flare gas can be at a pressure of about 3 to about 60 bar, about 8 to about 35 bar (typically corresponding to about 1.2× the pressure ratio of the gas turbine air compressor), about 5 to about 40 bar, at least about 10 bar, at least about 20 bar, and at least about 1.1× the pressure ratio of the air compressor, from about 1.05× to about 1.8× the pressure ratio of the gas air compressor and greater and smaller values. The compressed flare gas (i.e., fuel for the system 500) is then mixed with the compressed air and ignited in the combustion box 504, where it is partially oxidized. The pressure of the air when mixed with the compressed flare gas, can be any of the above ranges of pressure for the flare gas; and preferably will be the same pressure as the flare gas. In the embodiment of the operation of the process as shown in FIG. 6, the pressure of the flare gas and air is 8 bar, when they are introduced into the combustion box 504 for partial oxidation to form syngas.

The compressor 503 is connected by rotation shaft 529, to motor or generator 536. Rotating shaft 519*b* contexts turbine 537 with motor or generator 536.

The syngas exits the combustion box 504 via line 521 and flows into filter 522 where particulates, e.g., soot, are removed. The syngas then flows into heat exchange 523 where the temperature is lowered to the methanol synthesis window, preferably 200° C.-500° C. (see, e.g., FIG. 6). The heat exchanger 523 is part of a heat exchanger loop 524. The syngas then flows from heater exchanger 523 to the synthesis unit 529. The synthesis unit has two reactors 529*a* and 529*b*. It is noted that a single stage or reactor can be used, and that more than two stages or reactors can be used. The synthesis unit 529 converts the syngas to methanol, which then flows to hold and separation unit 530. Unit 530 separates the liquid methanol from any remaining gas. The methanol is discharged through line 531 for storage, further processing, use, shipping, etc. The gases flow through line 532 to hydrogen separator unit 533. Hydrogen leaves separation unit 533 via line 534 and flows back to the synthesis unit 529, where it is used to adjust the $H_2/CO$ ratio of the syngas. The remaining gases, e.g., low $H_2$ concentration exhaust products stream, from the unit 533, flow into the turbine 537 and then to exhaust line 538.

The operation of the system of FIG. 5 under the state conditions of FIG. 6 revolves around the integration of the synthesis reactor within the gas turbine cycle. The fuel system, compressor, and rich combustor are similar to the systems of Example 5. However, instead of delivering combustion products into the turbine, in this Example 7 the syngas at the exit of the combustor 504 flows through a recuperating heat exchanger 523 until the syngas temperature is acceptable for the synthesis reactor 529. At the exit of the synthesis reactor 529, the spent gas is returned through the recuperating heat exchanger system 524, and delivered to the turbine 537 to expand back to ambient pressure. An advantage of this embodiment is fewer components, but it requires a high-temperature recuperating heat exchanger and more sophisticated controls, than the embodiment of Example 5.

Example 8

An embodiment of these systems and methods includes the use of water in the waste gas, e.g., flare gas, or added directly into the POX combustor to raise the $H_2/CO$ ratio to enhance the efficiency and effectiveness of the downstream synthesis reactor. This embodiment can be used with any of the present systems, including the Examples.

Example 9

An embodiment of these systems and methods includes the addition of substantially oxygen-free gas, to the reformer, e.g., the turbine, including such as that at the exit of the high pressure side of hydrogen separator, to pressurize seals and ensure that no air is entrained into the secondary passages of the turbine. This embodiment can be used with any of the present systems, including the Examples.

Example 10

A hybrid system, consisting of reciprocating engine(s) and gas turbine(s), whereby the reciprocating engine(s) may be used for auxiliary power generation, or to supply additional synthesis gas is also contemplated. The hybrid system may contain reciprocating engines and gas turbines at scales sized to match the inlet gas feed.

Example 11

Figure 7A:
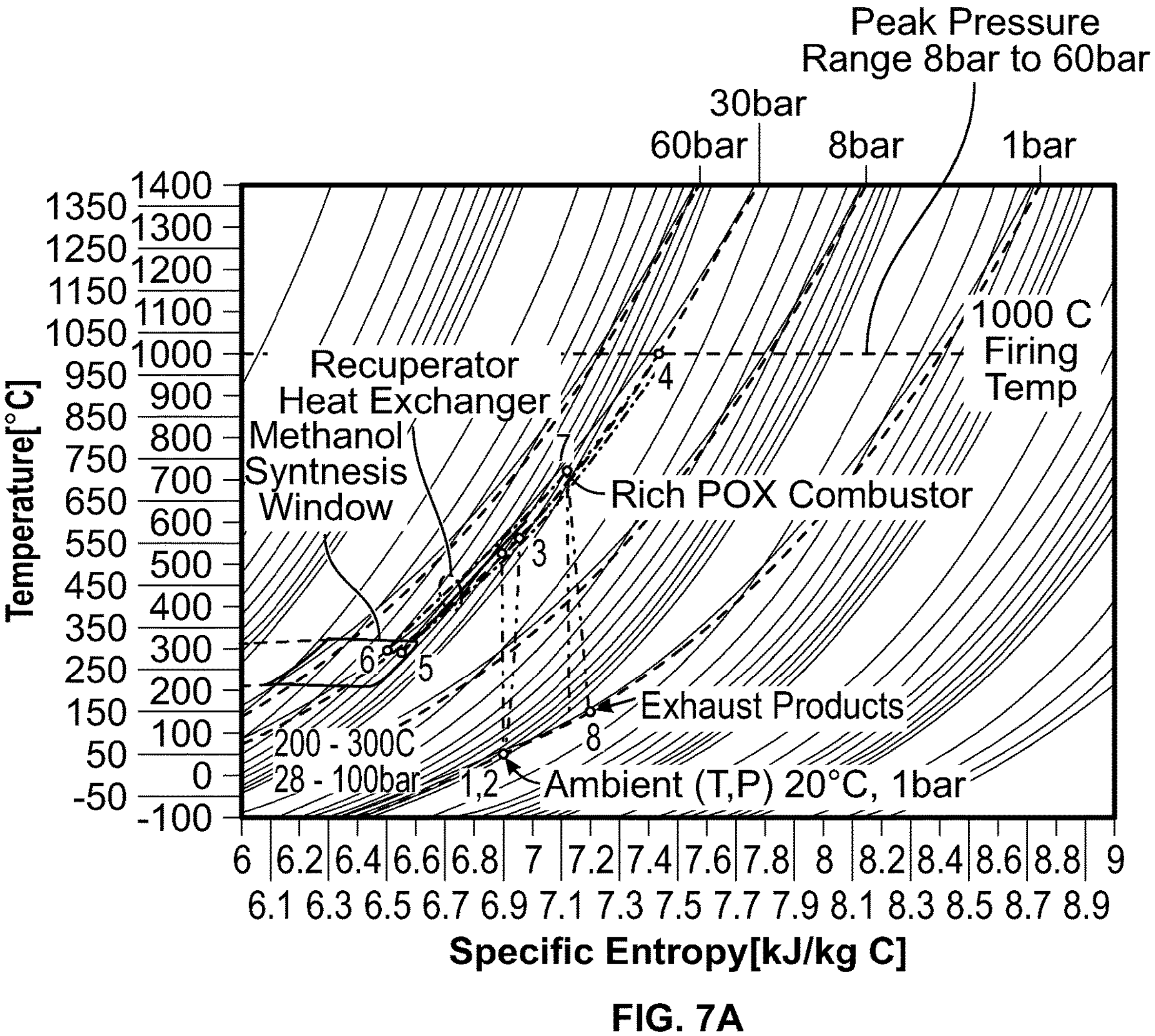
FIG. 7A is a T-S diagram showing an embodiment of a process, operating conditions and thermodynamic state points for converting flaRE gas to syngas to methanol, using an embodiment of the present system in accordance with the present inventions.

In an embodiment of the system of FIG. 1, the reformer is the gas jet turbine of FIG. 7. This system can be preferably operated as set forth in the T-S diagram of FIG. 7A. The reference points (numbers—3, 4, 5, 6, 7, 8, in FIG. 7) correspond to process conditions, i.e., state points, at those locations in the system of FIG. 7, and those process conditions are shown by corresponding reference points in FIG. 7A. The state point 1 (not shown in FIG. 7), is the conditions of the flare gas as it is injected at 742. The starting specific entropy for this process is at points 1, 2 (6.9 kJ/kg° C.) and the final specific entropy point for this process is 8 (7.2 kJ/kg° C.). Thus, the difference between the start and final specific entropy is 0.3 kJ/kg° C.

Example 12

Figure 8:
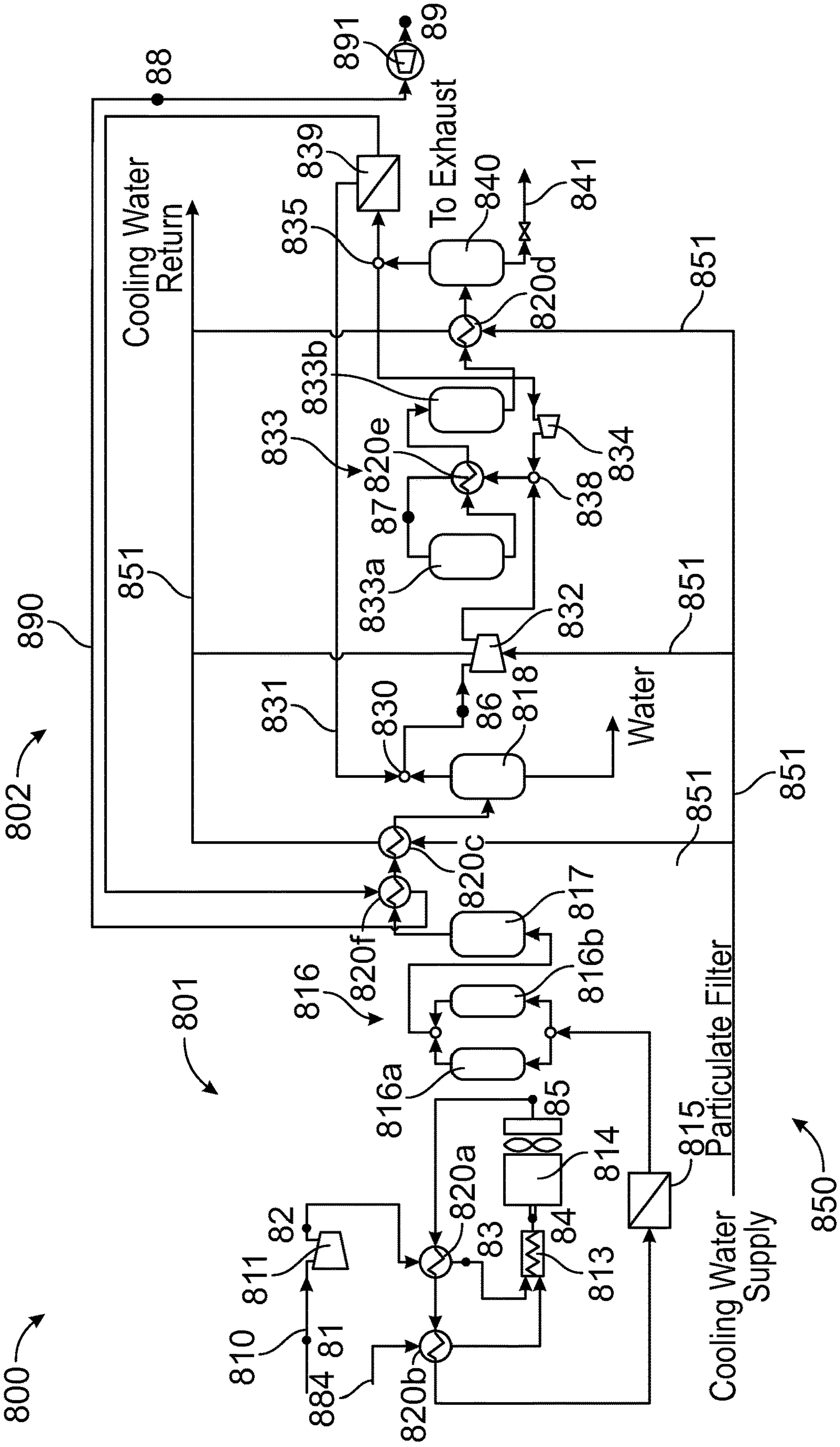
FIG. 8 is a schematic flow diagram of an embodiment of a system and process in accordance with the present inventions.

Turning to FIG. 8 there is shown an embodiment of a system and method for the conversion of flare gas into a value-added product. The system 800 has a reformer stage 801 and a synthesis stage 802. The system 800 has an air intake 810, that feeds air through into a compressor 811, which compresses the air. The compressed air is feed through heat exchanger 820*a* into a mixer 813. The system has a flare gas intake 884. The flare gas flows through a heat exchanger 820*b* into the mixer 813. The mixer 813, provides a predetermined mix of air and flare gas, as disclosed and taught in greater detail in this specification, to a reformer 814, which is a reciprocating engine.

The fuel-air mixture that is formed in mixer 813 is preferably rich, more preferably having an overall fuel/air equivalence ratio (ϕ or ER) greater than 1, greater than 1.5, greater than 2, greater than 3, from about 1.5 to about 4.0, about 1.1 to about 3.5, about 2 to about 4.5, and about 1.1 to about 3, and greater values.

It being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing" reformers, and air breathing engines as used herein are understood to also include engines using air modified with the addition of water, oxygen or both.

The reciprocating engine 814 combusts the predetermined mixture of flare gas and air to form syngas. The syngas flows through heat exchangers 820*a*, 820*b* and into a filter 815, e.g., a particulate filter.

After passing through the filter 815, the syngas flows to a guard bed reactor assembly 816, having two guard bed reactors 816*a*, 816*b*. The guard bed reactor 816 has materials, e.g., catalysts, that remove contaminates and other materials from the syngas that would harm, inhibit or foul later apparatus and processes in the system. For example, the guard bed reactor 816 may contain catalyst or other materials to remove sulfur (e.g., iron sponge, zinc oxide or similar) and halogenated compounds.

After leaving the guard bed reactor 816, the syngas flows to a deoxo reactor 817. The deoxo reactor 817 removes excess oxygen from the reprocessed gas (e.g., syngas) by oxidizing combustible compounds in the mixture such as methane, CO, and $H_2$, where the oxygen is converted to water. Catalyst for the deoxo reaction are platinum, palladium, and other active materials supported on alumina or other catalyst support materials.

The system 800 has a cooling system 850, which uses a cooling fluid, e.g., cooling water, that is flow through cooling lines, e.g., 851.

After leaving the deoxo reactor 817, the syngas flows to heat exchanger 820*c*. The reprocessed gas (e.g., syngas) then flows from heat exchanger 820*f* and 820*c* to a water removal unit 818, e.g., a water knockout drum, demister, dryer, membrane, cyclone, desiccant or similar, where water is removed from the syngas. In general, the syngas upon leaving unit 818 should have less than about 5% water by weight, less than about 2%, less than about 1% and less than about 0.1% water.

After leaving unit 818, the now dry syngas is in the synthesis stage 802. In stage 802 the now dry syngas flows to an assembly 830. Assembly 830 provides for the controlled addition of hydrogen from line 831 into the now dry syngas. In this manner the ratio of the syngas components can be adjusted and controlled to a predetermined ratio. The hydrogen is provided from hydrogen separate 839. The ratio adjusted dry syngas leaves assembly 830 and flow to compressor 832. Compressor 832 compresses the syngas to an optimum pressure as taught and disclosed in this specification, for use the synthesis unit 833. Preferably, the synthesis unit 833 is a two-stage unit with a first reactor unit 833*a* and a second reactor unit 833*b*. Synthesis unit 833 also has heat exchanger 820*e*.

The synthesis unit 833 converts the ratio adjusted dry syngas into a value-added product, methanol. The methanol flows into to heat exchanger 820*d*. The methanol flows to a collection unit 840. The collection unit 840 collects the methanol and flows it through line 841 for sale, holding, or further processing.

Generally, the syngas is compressed to a pressure of about 15 to about 100 bar and preferably 30-50 bar, and about 25 to about 80 bar, at least about 10 bar, at least about 25 bar and at least about 50 bar, and greater and lower pressures. The temperature of the pressurized syngas is adjusted to a temperature of about 150° C. to about 350° C. and preferably 250° C., about 200° C. to about 300° C., about 250° C. to about 375° C., greater than 125° C., greater than 150° C., greater than 200° C., greater than 250° C., greater than 350° C., and less than 400° C., and higher and lower temperatures. The pressure and temperature-controlled syngas is then feed to reactors for transforming the syngas into a more useful, more easily transportable, and economically viable product such as methanol, ethanol, ammonia, dimethylether, F-T liquids, and other fuels or chemicals. In a preferred embodiment methanol is produced using the reaction of syngas to methanol, reactions for hydrogenation of CO, hydrogenation of $CO_2$, and reverse water-gas shift using actively cooled reactors, such as a heat-exchanged reactor or boiling water reactor, and a copper containing catalyst such as $Cu/ZnO/Al_2O_3$ or the like.

Generally, and in preferred embodiments, the characteristic length scale of the reactors used in this system are sufficiently small (e.g., micro-channel or mini-channels) that they can be shaped into unconventional shapes and topologies using new 3D printing techniques for metals and other high-temperature materials, thus allowing compact packaging and tight control over reaction conditions. Other strategies for intensification of the downstream synthesis reactions can also be considered, such as selectively removing the product from the reactor in-situ, or in a closely coupled fashion, to shift the equilibrium-limited reaction to higher conversion. This process intensification may minimize the need for large recycle streams or allow the reaction to proceed at milder conditions (e.g., lower pressure) thereby increasing process safety margins.

In general, the ratio of $H_2/CO$ in the syngas produced by the engine can be tailored to the downstream conversion process. For example, for methanol synthesis or Fischer-Tropsch (F-T) synthesis the ideal $H_2/CO$ ratio is 2-3. For ammonia synthesis or for hydrogen production, the maximum possible $H_2/CO$ ratio is desirable and can be enhanced by, for example, steam addition to promote the water-gas shift reaction. For ammonia and hydrogen production, the CO is not required by the downstream synthesis. As such, CO and $CO_2$ byproducts can be collected, sequestered, stored or utilized for other purposes.

The collection unit 840 also has a line that flows gas separated from the methanol to tee-connector 835, where it is sent to hydrogen separate 839, to a recycle loop or both. Recycle loop has compressor 834 and valve 838 to feed the methanol back into the synthesis unit 833. Hydrogen separation can be achieved by via membrane separation or pressure swing absorption (PSA) or the like in the hydrogen separation unit 839.

The remaining gas after hydrogen separation is sent through loop 890 and through heat exchanger 820*f* to turbine expander 891, where the gas is then sent to exhaust.

Example 13

In an embodiment of the system of FIG. 8, the reformer 814 is a spark ignition (otto cycle) reciprocating engine. This system can be preferably operated as set forth in the T-S diagram of FIG. 9. The reference points (numbers—81, 82, 83, 84, 85, 86, 87, 88, 89 in FIG. 8) correspond to process conditions, i.e., state points, at those locations in the system of FIG. 8, and those process conditions are shown by corresponding reference points in FIG. 9. The line from state point 84*a*' to 84*b*' represents a reduction in compression ratio that occurs in response to a more reactive flare gas fuel. State point 85*b* relates to the syngas exiting the syngas reformer after the expansion of the turbocharger. The expansion from 85 to 85*b* occurs within the turbocharger. The starting specific entropy for this process is at points 81, 82 (6.9 kJ/kg° C.) and the final specific entropy point for this process is 89 (6.95 kJ/kg° C.). Thus, the difference between the start and final specific entropy is 0.05 kJ/kg° C.

Figures 9, 9A:
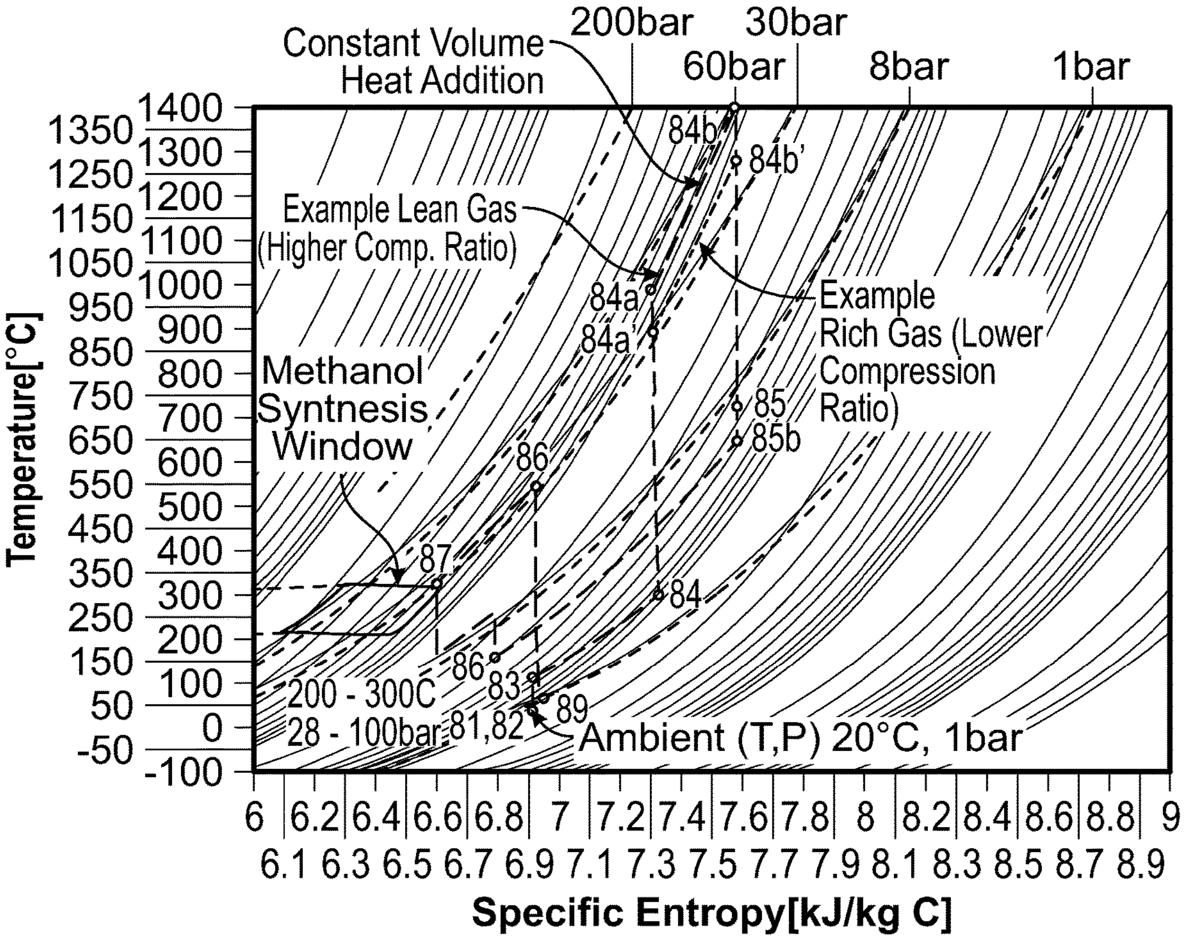
FIG. 9 is a T-S diagram showing an embodiment of a process, operating conditions and thermodynamic state points for converting flag gas to syngas to methanol, using the system of FIG. 8 having a spark ignition reciprocating engine in accordance with the present inventions.
FIG. 9A is a table setting out an embodiment of operating conditions for the system of FIG. 8 having a spark ignition reciprocating engine, and the operating conditions of FIG. 9 in accordance with the present inventions.

FIG. 9A is a table set out further operating conditions for the system of this Example. FIG. 9A shows the compression power (gross and net) for flare gas to methanol process using the turbo expander 891 under the conditions of a 3 bar backpressure and a 50 bar methanol synthesis pressure.

Example 14

Figure 11:
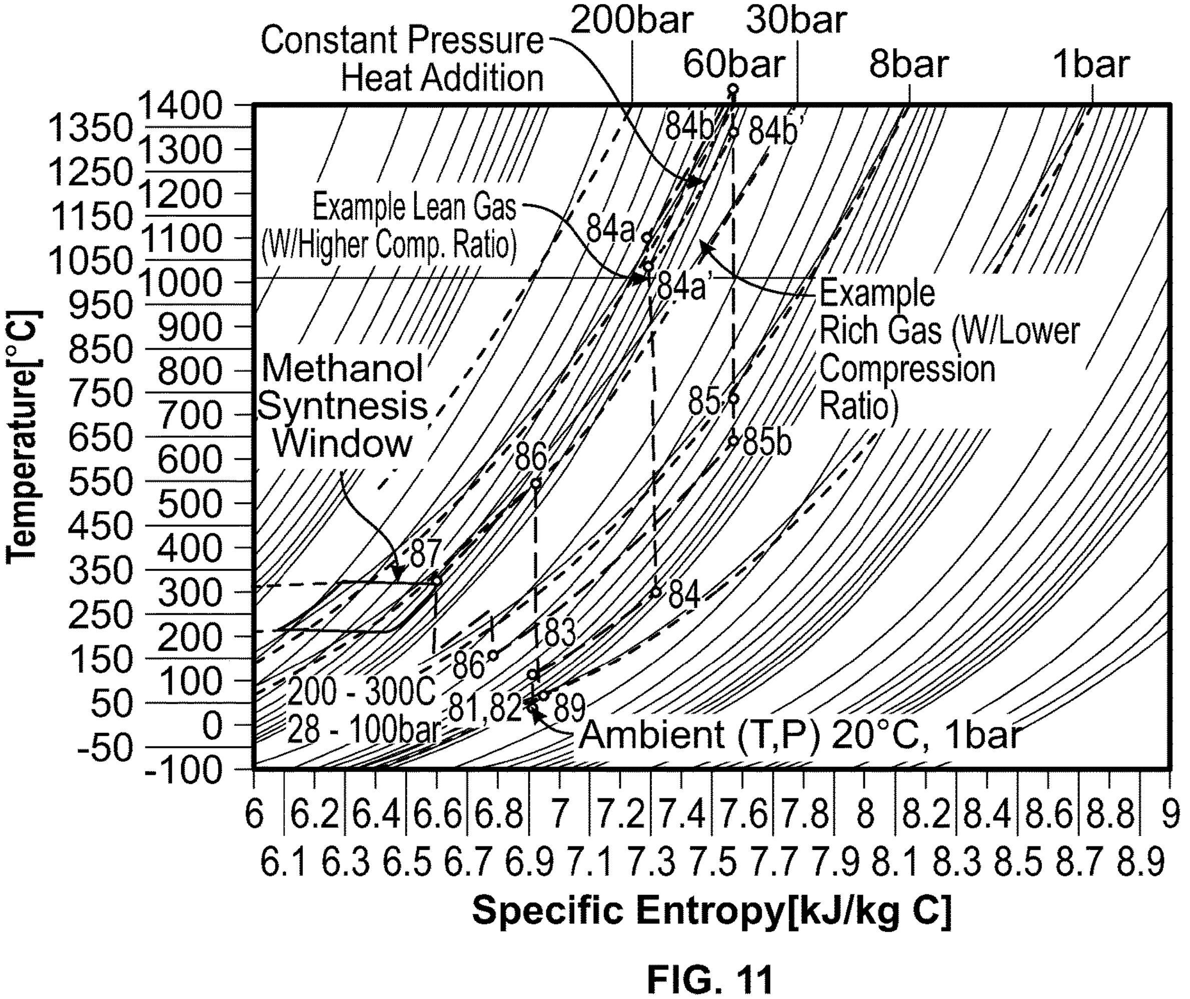
FIG. 11 is a T-S diagram showing an embodiment of a process, operating conditions and thermodynamic state points for converting flag gas to syngas to methanol, using the system of FIG. 8 having a compression ignition reciprocating engine in accordance with the present inventions.

In an embodiment of the system of FIG. 8, the reformer 814 is a compression ignition (diesel cycle) reciprocating engine. This system can be preferably operated as set forth in the T-S diagram of FIG. 11. The reference points (numbers—81, 82, 83, 84, 85, 86, 87, 88, 89 in FIG. 8) correspond to process conditions, i.e., state points, at those locations in the system of FIG. 8, and those process conditions are shown by corresponding reference points in FIG. 11. The line from state point 84*a*' to 84*b*' represents a reduction in compression ratio that occurs in response to a more reactive flare gas fuel. State point 85*b* relates to the syngas exiting the syngas reformer after the expansion of the turbocharger. The expansion from 85 to 85*b* occurs within the turbocharger. The starting specific entropy for this process is at points 81, 82 (6.9 kJ/kg° C.) and the final specific entropy point for this process is 89 (6.95 kJ/kg° C.). Thus, the difference between the start and final specific entropy is 0.05 kJ/kg° C.

Example 15

Figure 10A:
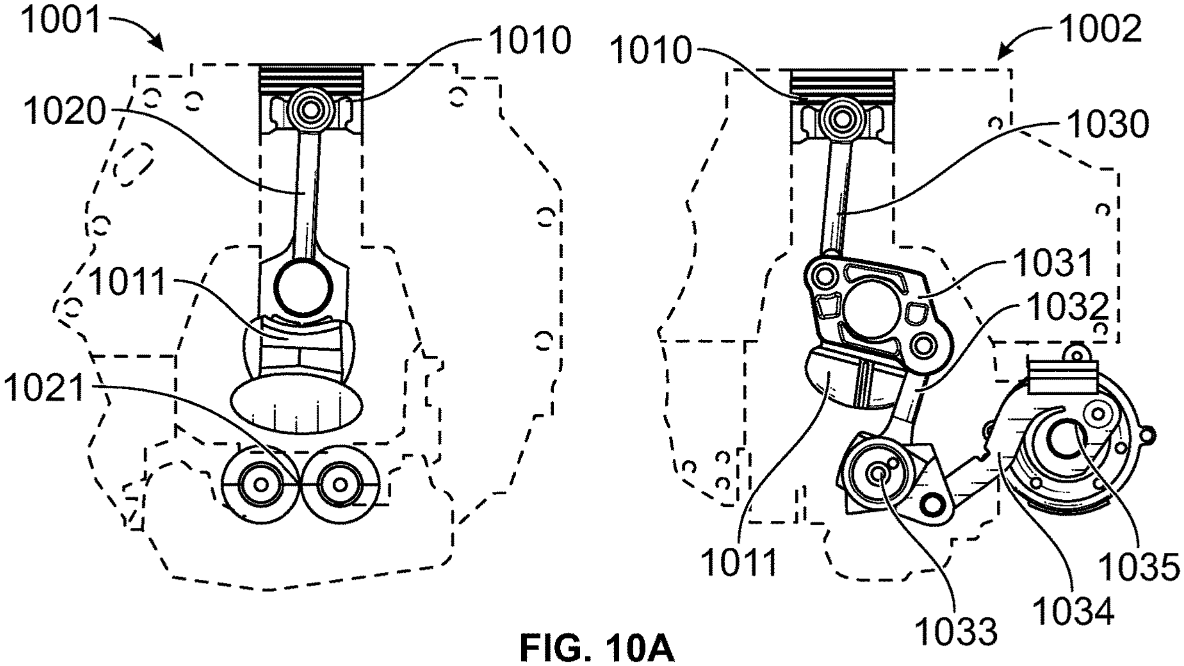
FIG. 10A is a cross section view of embodiments of engine reformer s accordance with the present inventions.
Figure 10B:
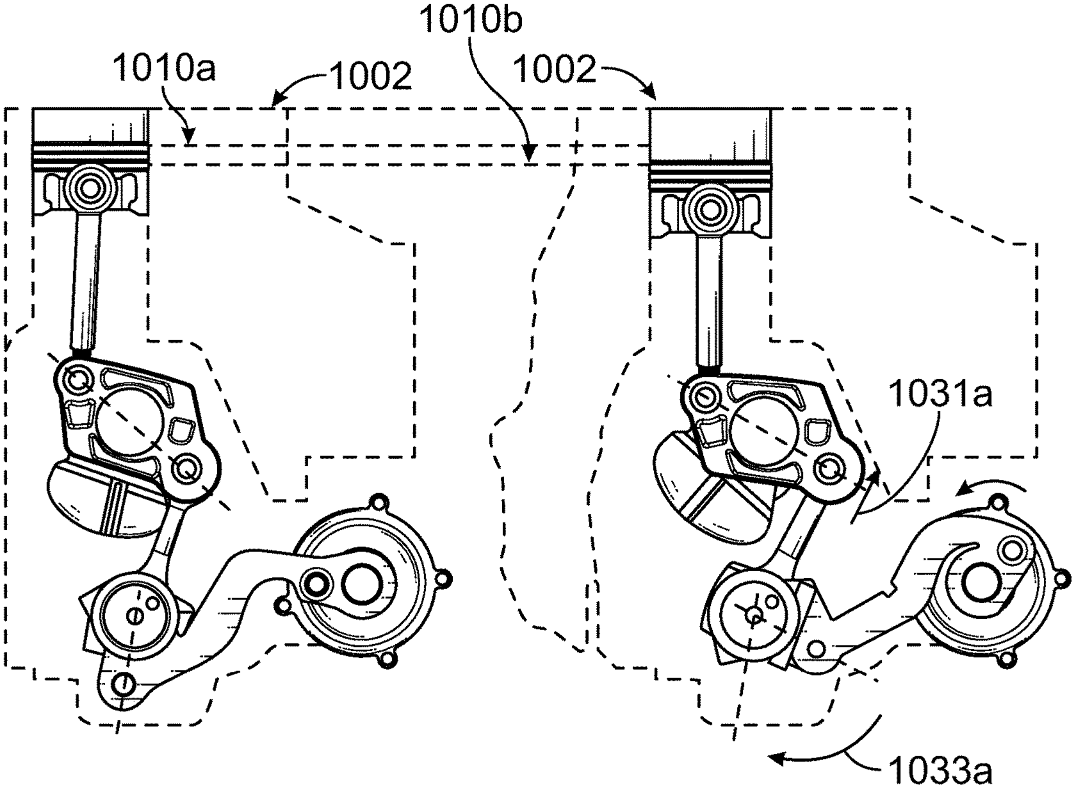
FIG. 10B is a cross sectional view of an embodiment of a variable compression engine reformer, showing the piston heights, in accordance with the present inventions.

Turning to FIGS. 10A and 10B there is shown an embodiment of a variable compression ratio engine that can be used as a reformer in embodiments of the present systems, including the Examples. The variable compression ration engine, 1002 can be one such as the Nissan VC-turbo engine, that uses a multi-link system in place of a traditional connecting rod to rotate the crankshaft, and an actuator motor changes the multi-link system endpoint in order to vary the pistons' reach to transform the compression ratio.

FIG. 10A is a cutaway view of a conventional engine 1001 compared to a partial cutaway view of a variable compression engine 1002. The piston 1010 are the crank 1011 are the same. The conventional engine 1001 has a connection rod 1020, and a $2^{nd}$ balancer 1021. The variable compression engine 1002 has a U-link 1030, an L-link 1031, a C-link 1032, a control shaft 1033, an A-link 1034 and an actuator Motor 1035.

The components of the variable compression engine 1002 make it possible to vary the compression ratio continuously as needed within the range of about 8:1 (for high load) to about 14:1 (for low load). For an automobile engine made by Nissan, the optimal compression ratio can be continuously set to match the operation of the accelerator pedal by the driver. A schematic of this linkage is shown on FIGS. 10A and 10B. The effects of this linkage on on piston height is shown on FIG. 10B. This approach can be applied to a two-stroke or four-stroke reciprocating engine, although an engine as described here is preferably operated as a four-stroke. Thus, using the variable compression engine as a reformer, the optimal compression ratio for producing syngas can be continuously set to accommodate combustion properties from variation in the flare gas with variable compression ratio. In this manner, in embodiments, an engine with a linkage to rotate the crankshafts to vary the compression ratio to run rich with variable flare gas compositions is utilized to produce synthetic gas.

Thus, and for illustration, turning to FIG. 10B, the relative adjustments for the variable compression reciprocating engine reformer 1002 are shown. Piston height 1010*a* is for 14:1 compression ratio. Piston height 1010*b* is for 8:1 compression ratio. The adjustment of the linkages are shown by arrows 1031*a* and 1033*a*.

Example 16

Figure 12:
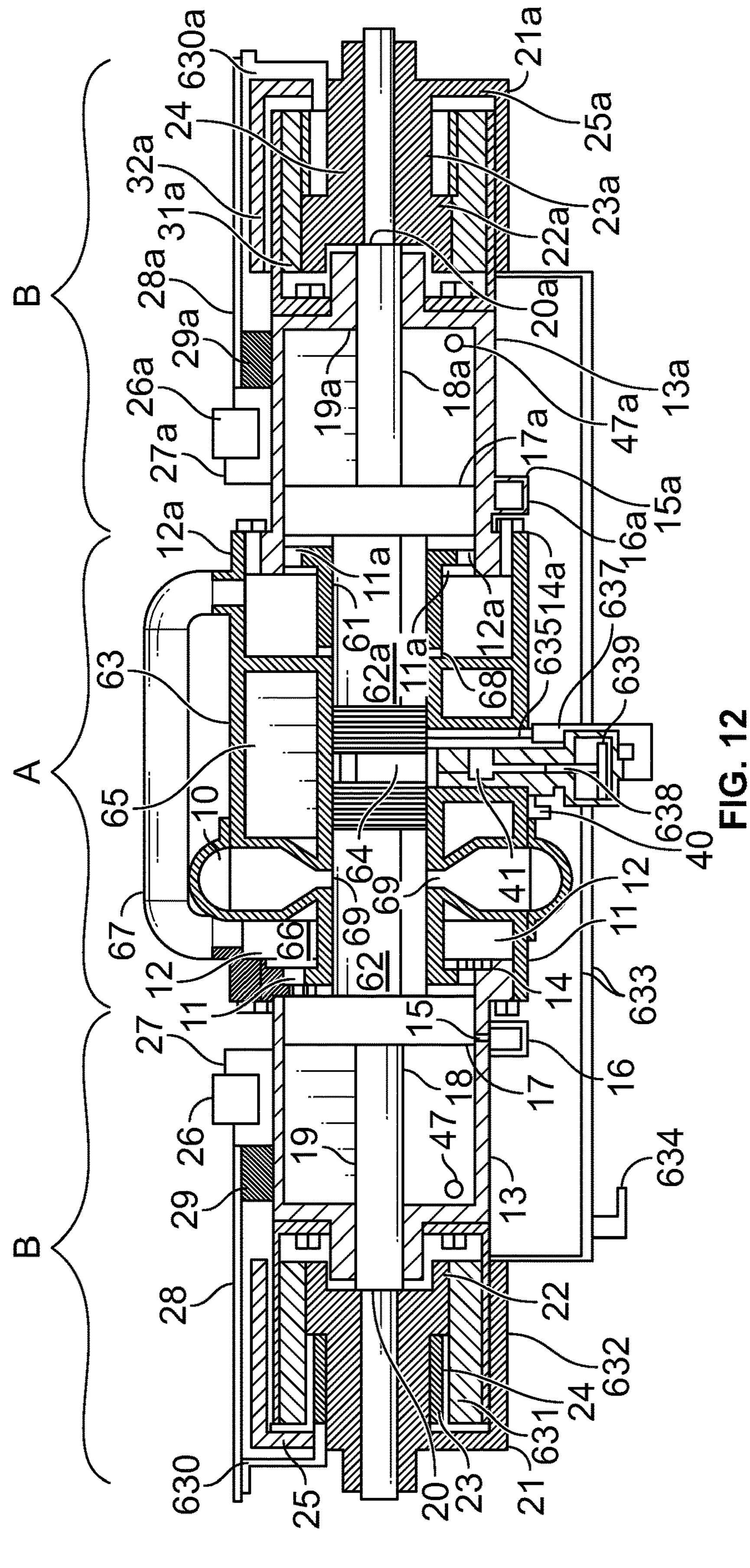
FIG. 12 is a cross sectional view of an opposed-piston internal combustion reciprocating reformer engine in accordance with the present inventions.
Figure 13:
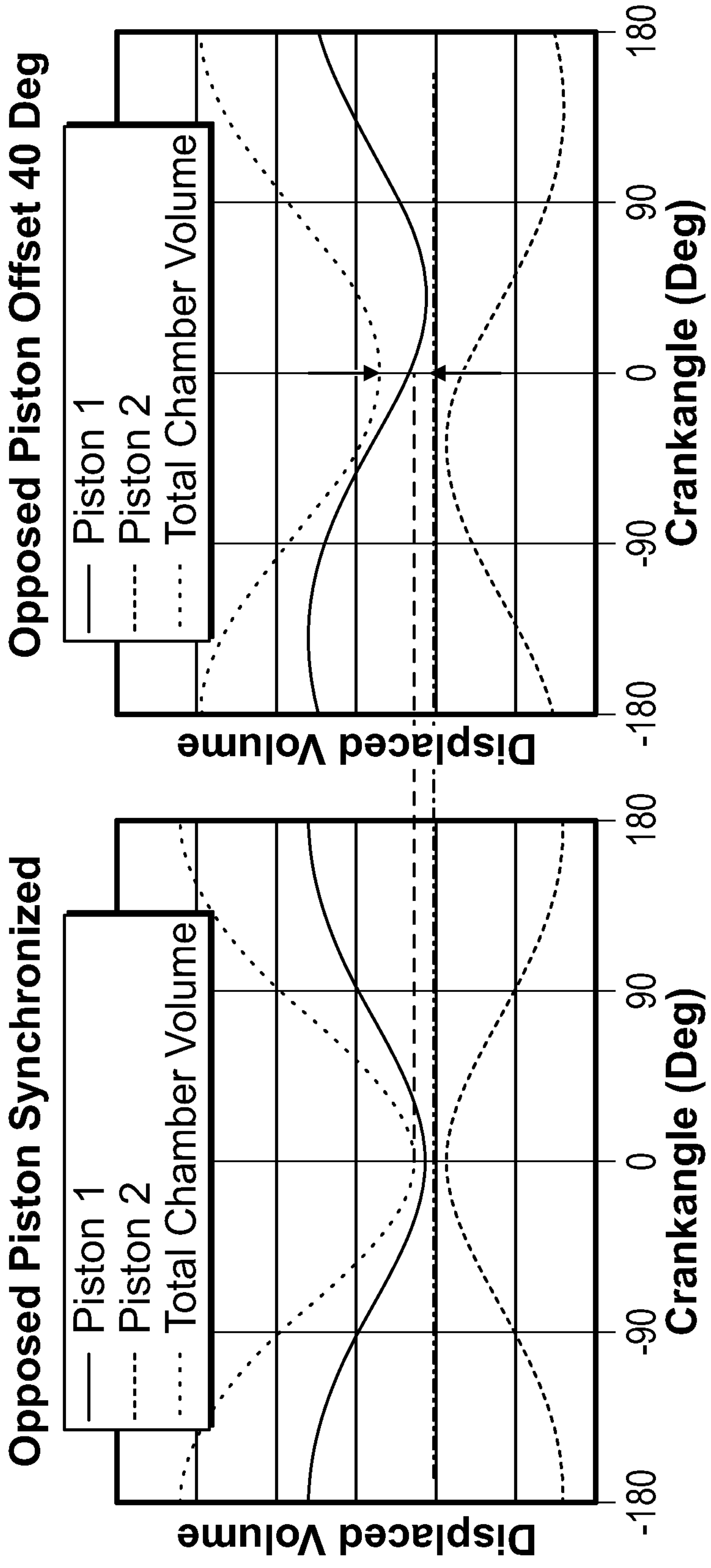
FIG. 13 is a graph comparing the displaced volumes of an opposed piston engine reformer in accordance with the present inventions.

Turning to FIG. 12, there is shown an embodiment on an engine for production of syngas from compression-ignition of rich fuel-air mixtures is preferred due to simplicity (lower part count) and better performance (high compression ratio yielding faster burn times). This engine reformer can be used in embodiments of the present systems, including the Examples. An example architecture is the opposed-piston free-piston linear internal combustion engine with integrated linear motor/generator, such as that produced by MainSpring Energy (aka Etagen). U.S. Pat. No. 2,362,151 discloses a basic engine configuration for modification in accordance with the teachings of the present specification, the entire disclosure of which is incorporated herein by reference.

Thus, turning to FIG. 12, the a free piston engine "A" is connected to two single phase generators "B" and "B", which can be operated by the engine. When used as a reformer the generators may not be present, or can be used to power components in the system.

The free piston engine A has a cylinder 61 in which the pistons 62-62*a* reciprocate, and which is surrounded by a second cylinder 63 having the annular water chamber 65 therein encompassing the explosion chamber 64 of the engine. Annular air chambers 66 are formed in the end portions of cylinder 63 as shown and are connected by a passage 67 whereby the air pressure in the two chambers is equalized. Intake passages 68 lead from chamber 66*a* to the interior of cylinder 61, and discharge passages 69 lead from the opposite end portion of the cylinder 61 to discharge into manifold 10.

Inasmuch as the two ends of the device are duplicates one end only will be described in detail and similar parts on the other end will be indicated by similar characters followed by the character "a".

Through the outer end of chamber 66 are formed passages 11 fitted with inwardly opening check valves 12, the said passages leading to an annular cylinder 13 axially disposed relative to cylinder 61 and somewhat larger In diameter than said cylinder- and mounted end wise thereon as at 14. This cylinder 13 is provided with an air intake passage at 15 fitted with an inwardly operating check valve as at 18 and disposed adjacent the inner end of said cylinder.

The piston 12 has an enlarged head 17 thereon to reciprocate in chamber 13, and a stem 18 projects axially outwardly from said head and through the bearing 19 in the outer end of the chamber 13 and has a shoulder 20 formed therein as shown, exteriorly of chamber 13 to form a seat for the magnet 21.

The magnet 21 is a field magnet, and in the present instance comprises a part 22, circular in form, seated on the shoulder 20, a second member 24 of smaller diameter seated on the member 22, and a winding of wire on the second member as indicated at 23 and grounded to said second part. This second member 24 is also provided with a flange 25 extending outwardly from its outer end at right anglers to its axis, and then turned backwardly in parallel relation with the axis and with a diameter slightly greater than the chamber 13 to encompass the magnet parts 22 and 24 as shown. The winding 23 is energized by means of a battery at 26 grounded to the engine at 21 and connected to a bar 28 mounted upon the engine at 29 and extending forwardly thereof as indicated, in parallel relation with its axis. A shoe 630 slidably engages the bar 28 and is in fixed contact with the coil 23 so that the magnet is energized at all times regardless of its position with relation to the fixed end of the device.

The armature comprises a coil of wire as 631 within a supporting cylinder 632 mounted upon the outer end of chamber 11 to encompass the magnet parts 22 and 24. Wires as 633 connect the armatures 631 and 631*a*, and electricity is taken off of these wires as at 34.

When the device is in operation the outward movement or the piston heads 17-17*a* draw air into the chambers 13-13*a* through valves 16-16*a*, and on their inward movement push the air through valves 12 into chamber 66-66*a*. The air in chamber 68*a* is sufficiently compressed to flow forcibly into the cylinder 61 when the piston 62*a* uncovers the passages 68. The exhaust passages 69 are uncovered at substantially the same time as the passages 68 so that the air entering the cylinder 61 at 68 will scavenge the same and carry out all of the burnt gases at 69 leaving the cylinder filled with fresh air.

But in the movement of pistons 12-12*a* just described the piston heads 17-17*a* compress the air entrapped in the chamber 13-13*a*, which form cushions which forcibly drive the said pistons back in cylinder 61 compressing the air therein. As the pistons approach each other the compressed air trapped between them, or at least a small portion thereof, is discharged through passage 635 and pipe 637 to actuate a plunger 638 in injector 639 in which the fuel oil is admitted at 49 and discharged through valve 41 into combustion chamber 64. These parts are proportioned and arranged to form a combustible mixture at the moment when the pistons 62-62*a* approach each other most closely, the resulting explosion diving the pistons outwardly again to repeat the cycle. The valves at 47-47*a* are inserted in chambers 13-13*a* to permit the drawing of air into said chambers to compensate for such air as may leak out of the same past the heads 17-17*a* or paste bearings 19-19*a*.

In an engine of this kind the pistons 62-62*a* are reciprocated at high speed, upwards of some ten thousand times a minute, and the magnets 21-21*a* are, or course, reciprocated at the same high speed. In this manner the mechanical energy of the engine is converted into electrical energy, since the rapid reciprocation of the magnetic fields about the magnets 21-21*a* through the induction cons 631-631*a* will rapidly after the number of lines or force passing through the coils.

This engine is modified with digital electronic controls (sensor and control system) to achieve a practical and high efficiency engine for small-scale power generation. This approach can be applied to a two-stroke or four-stroke reciprocating engine, although a linear engine with fixed ports in the side walls is generally operated as a two-stroke. Thus, this linear engine operating under rich conditions can be a reformer in any of the Examples of systems to produce syngas. Preferably this linear engine reformer is a free-piston configuration with an electronically-control linear motor/generator that allows the compression ratio to be varied according the properties of the incoming fuel. This linear engine reformer may also have a free-piston configuration with sensors to detect the in-cylinder combustion behavior under rich conditions and automatically adjust the compression ratio.

Example 17

An embodiment of a variable compression ratio engine reformer, for use in embodiments of the present systems, including the Examples, is through a crankshaft-driven opposed-piston engine utilizing a variable phaser on the crankshafts. Combustion chamber volume in such an engine is dictated by the relative positions of the pistons. Offsetting motion of one piston to the other increases minimum volume, thereby reducing compression ratio. Turning to FIG. 8 there is shown a comparison of displaced volume when the opposed pistons are synchronized (left) vs offset by 40 degrees (right). The compression ratio is higher when the pistons are synchronized, and reduces when the pistons are offset. An example of an opposed-piston linear engine with crank shafts is an engine developed by Achates Engines.

In an embodiment the opposed piston engine reformer has a variable phaser on the crankshafts to run rich with variable fuel to produce synthetic gas is novel.

This approach can be applied to a two-stroke or four-stroke reciprocating engine, although a linear engine with fixed ports in the side walls is generally operated as a two-stroke.

Example 18

Figure 14:
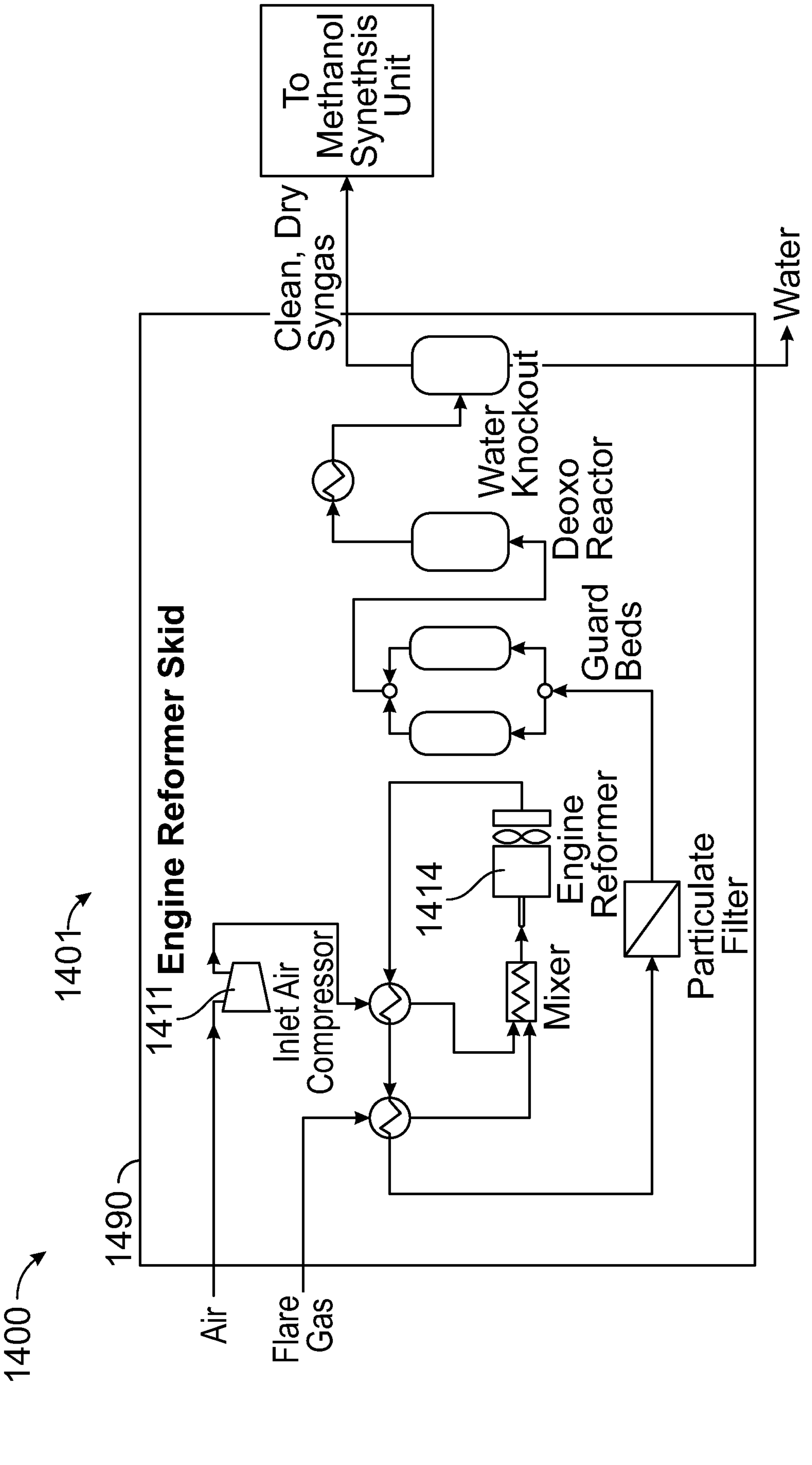
FIG. 14 is a schematic flow diagram of an embodiment of a system and process of a modular reformer stage in accordance with the present inventions.

Turning to FIG. 14 there is shown a modular reformer system and process that is a portion of a liquid-to-gas system 1400. This system 1400 has a reformer stage 1401, that is placed on a transport system 1490 (e.g. skid, truck bed, rail car, ship deck, barge, drilling platform, drill ship, container, or other platform, base or container), that can be readily moved by rail, air, truck or ship. The stage 1401 has a compressor 1411 and an engine reformer 1414, as well as other components as labeled on the drawing as taught and disclosed in this specification. It being understood that any of the engine reformers of the present systems and Examples could be used in the stage 1401. The stage 1401 provides clean syngas.

This stage can be used, or positioned with any unit that can further process the syngas into move valuable products. For example, this stage 1401 can be used with the modular methanol synthesis unit of the present inventions, such as the unit of Example 19.

Example 19

Figure 15:
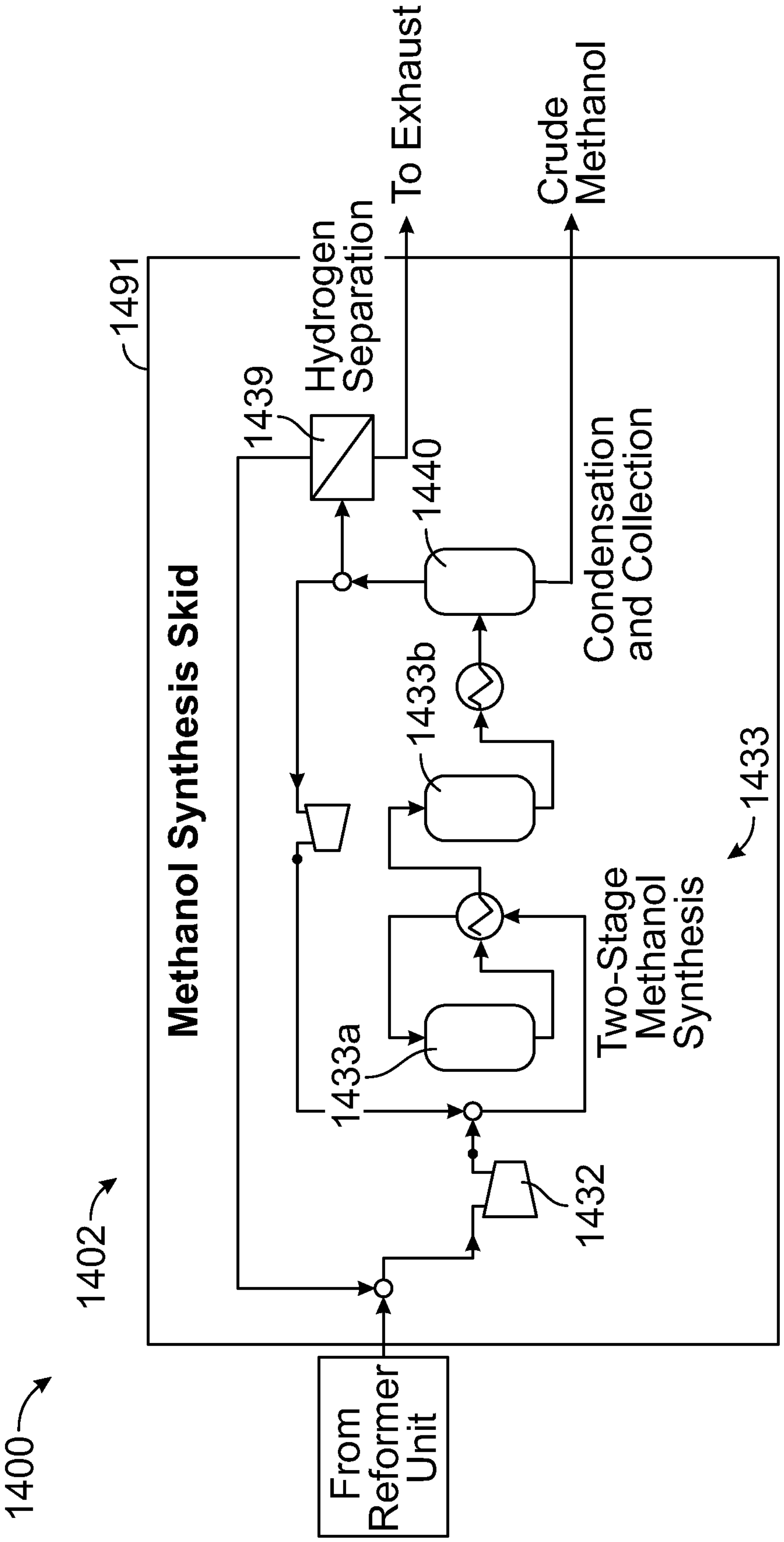
FIG. 15 is a schematic flow diagram of an embodiment of a system and process of a modular synthesis stage in accordance with the present inventions.

Turning to FIG. 15 there is shown a modular methanol synthesis system and process that is a portion of a liquid-to-gas system 1400. This system 1400, has a synthesis stage 1402, that can be placed on a transport system 1491 (e.g., skid, truck bed, rail car, ship deck, barge, drilling platform, drill ship, container, or other platform, base or container), that can be readily moved by rail, air, truck or ship. This stage 1402 is configured to receive clean, syngas. This stage 1402 can be used with the reformer stage 1401 of Example 18, as well as with other reformer stages as taught and disclosed in this specification, including the Examples. The stage 1402 produces an end product, e.g., methanol, from syngas.

The stage 1402 has a synthesis unit 1433, which is a two-stage unit with a first reactor unit 1433*a* and a second reactor unit 1433*b*. The stage has a hydrogen separator 1439, a collection unit 1440, as well as, other components as labeled on the drawing and as taught and disclosed in this specification. It being understood that any of the configurations of synthesis stages of the present systems and Examples could be used in stage 1402.

This stage 1402 can be positioned near a tank, storage container, or source of syngas and process that syngas into methanol.

Example 20

Figure 16:
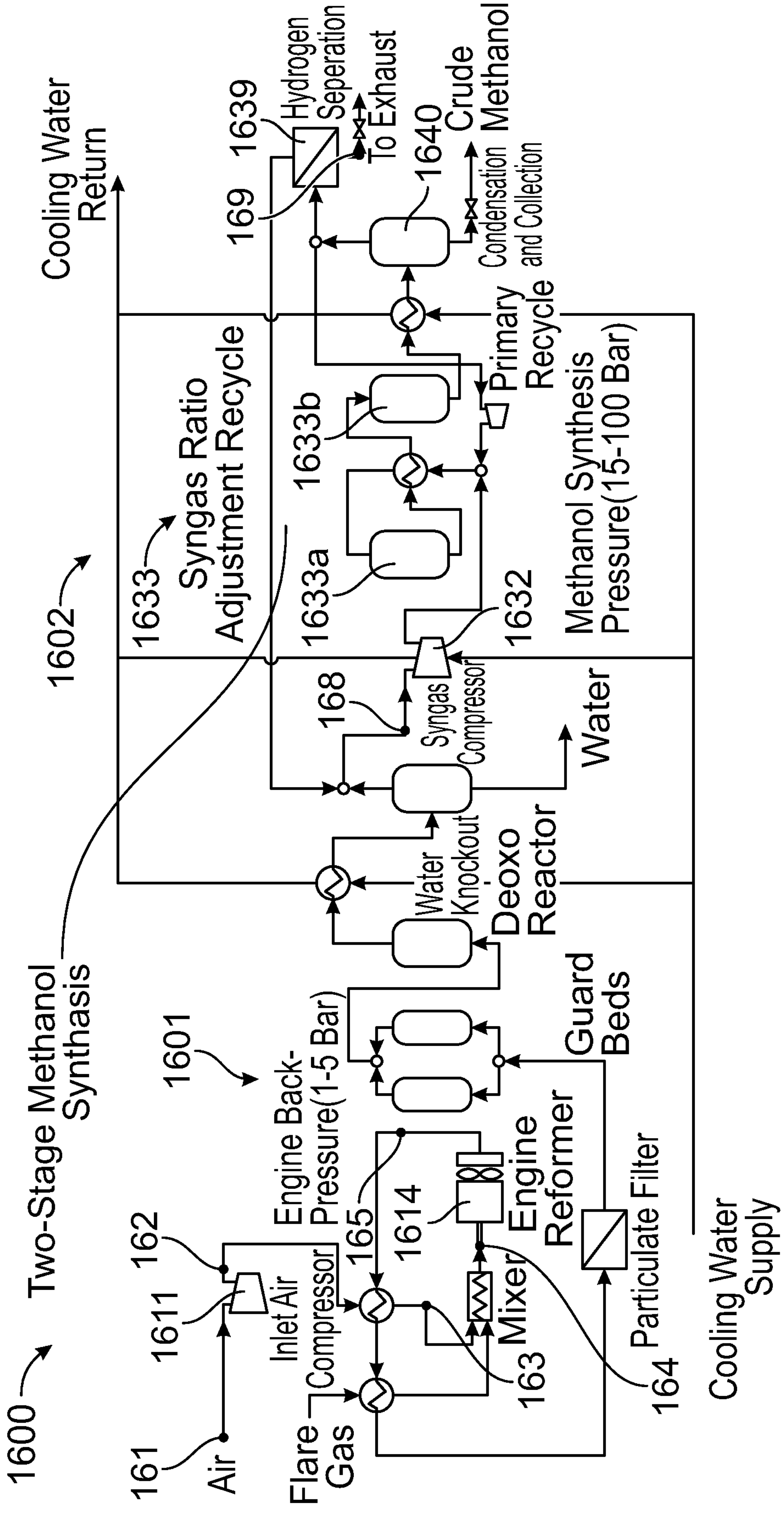
FIG. 16 is a schematic flow diagram of an embodiment of a system and process in accordance with the present inventions.
Figures 17, 17A:
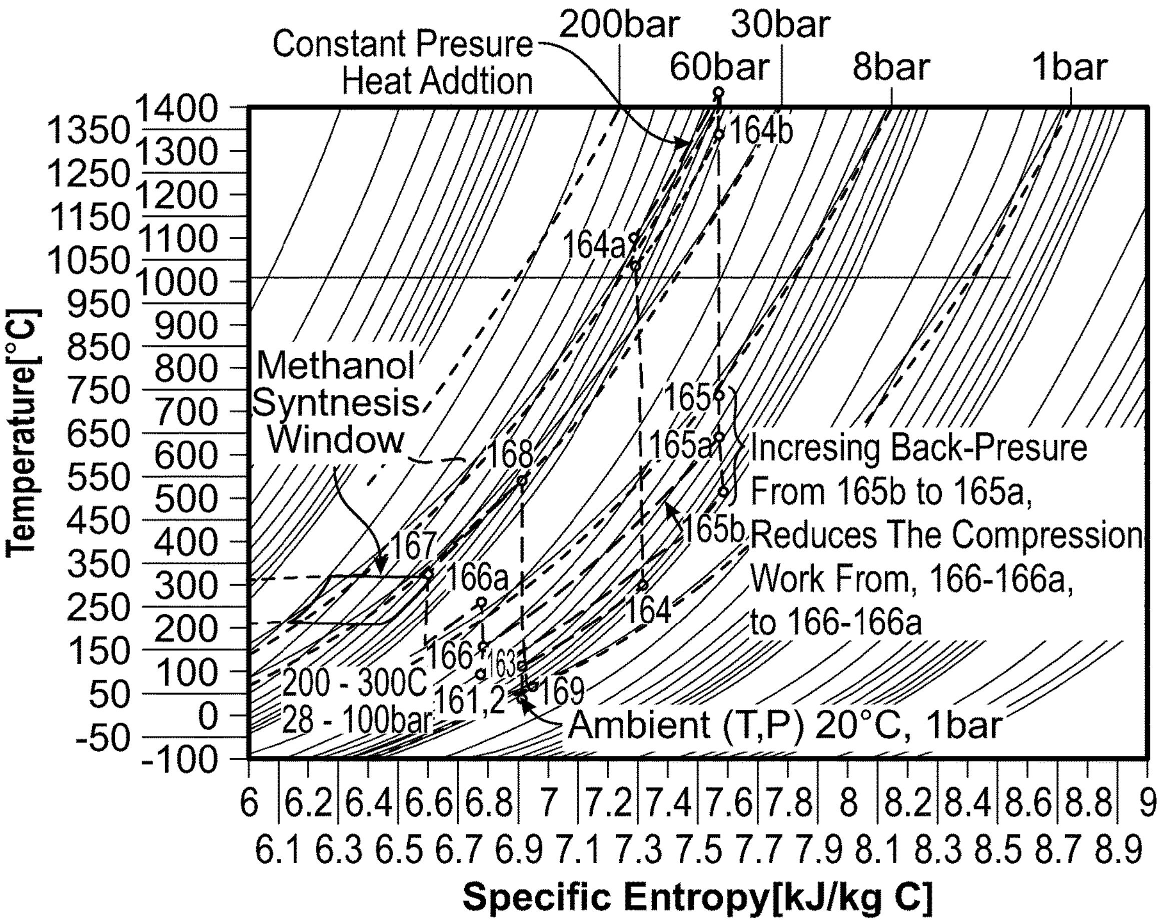
FIG. 17 is a T-S diagram showing an embodiment of a process, operating conditions and thermodynamic state points for converting flag gas to syngas to methanol, using the system of FIG. 16 in accordance with the present inventions.
FIG. 17A is a chart showing compressor power as function of engine backpressure for embodiments of the present systems in accordance with the present invention.

Turning to FIGS. 16, 17 and 17A. FIG. 16 shows an embodiment of a system and method for the conversion of flare gas into a value-added product, e.g., methanol. The system 1600 has a reformer stage 1601 and a synthesis stage 1602. The system 1600 has an air intake, that feeds air through into a compressor 1611, which compresses the air. The compressed air is feed through a heat exchanger into a mixer. The system has a flare gas intake. The flare gas flows through a heat exchanger into the mixer. The mixer provides a predetermined mix of air and waste gas, as taught and disclosed in this specification, to a reformer 1614, which is a reciprocating engine.

The fuel-air mixture that is formed in mixer is preferably rich, more preferably having an overall fuel/air equivalence ratio (ϕ or ER) greater than 1, greater than 1.5, greater than 2, greater than 3, from about 1.5 to about 4.0, about 1.1 to about 3.5, about 2 to about 4.5, and about 1.1 to about 3, and greater values.

It being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing" reformers, and air breathing engines as used herein are understood to also include engines using air modified with the addition of water, oxygen or both.

The reciprocating engine 1614 combusts the predetermined mixture of flare gas and air to form syngas. The syngas flows through heat exchangers and into a filter, e.g., a particulate filter.

After passing through the filter, the syngas flows to a guard bed reactor assembly, having two guard bed reactors. After leaving the guard bed reactor, the syngas flows to a deoxo reactor. The deoxo reactor removes excess oxygen from the reprocessed gas (e.g., syngas).

The system has a cooling system, which uses a cooling fluid, e.g., cooling water, that is flow through cooling lines.

After leaving the deoxo reactor, the syngas flows to heat exchanger. The reprocessed gas (e.g., syngas) then flows from the heat exchanger to a water removal unit, e.g., a water knockout drum, demister, dryer, membrane, cyclone, desiccant or similar, where water is removed from the syngas. In general, the syngas upon leaving unit the water removal unit should have less than about 5% water by weight, less than about 2%, less than about 1% and less than about 0.1% water.

After leaving the water removal unit, the now dry syngas flows into in the synthesis stage 1602. In stage 1602 the now dry syngas flows to an assembly that provides for the controlled addition of hydrogen from line into the now dry syngas. In this manner the ratio of the syngas components can be adjusted and controlled to a predetermined ratio. The hydrogen is provided from hydrogen separate 1639. The ratio adjusted dry syngas leaves the assembly and flows to compressor 1632. Compressor 1632 compresses the syngas to an optimum pressure as taught and disclosed in this specification, for use the synthesis unit 1633, which is a two-stage unit with a first reactor unit **1633*a* and a second reactor unit 1633*b*. Synthesis unit 1633** also has heat exchanger.

The synthesis unit 1633 converts the ratio adjusted dry syngas into a value-added product, e.g., methanol. The methanol flows into to heat exchanger and then to a collection unit 1640. The collection unit 1640 collects the methanol and flows it through a line for sale, holding, or further processing.

The collection unit 1640 also has a line that flows gas separated from the methanol to tee-connector, where it is sent to hydrogen separate 1639, to a recycle loop or both. Recycle loop has a compressor and a valve to feed the methanol back into the synthesis unit 1633.

The system 1600 can be preferably operated as set forth in the T-S diagram of FIG. 17. The reference points (numbers—161, 162, 163, 164, 165, 166, 167, 168, 169 in FIG. 17) correspond to process conditions, i.e., state points, at those locations in the system of FIG. 16, and those process conditions are shown by corresponding reference points in FIG. 17. The starting specific entropy for this process is at points 161, (6.9 kJ/kg° C.) and the final specific entropy point for this process is 169 (6.95 kJ/kg° C.). Thus, the difference between the start and final specific entropy is 0.05 kJ/kg° C.

Further, turning to FIG. 17A there is shown the predicted compressor work (total and for syngas compression only), as a function of the engine exhaust backpressure for a 50 bar downstream synthesis pressure. These data are generated using a chemical process simulation that performed the mass and energy balances for the embodiment of a liquid-to-gas system and method of the type shown in FIG. 16. The syngas compressor is treated as a three-stage compressor with interstage cooling. The isentropic efficiency of the compressor is assumed to be 75%, representative of industrial centrifugal and reciprocating compressors. The syngas ratio adjustment recycle stream enters the compressor at the inlet to the second stage. Increasing the engine exhaust backpressure from 2 bar up to 3 bar decreases the compression work by 20.4%. Further increasing the backpressure from 2 bar to 4 bar decreases the compression work by 28.0%. This trend suggests a diminishing return and therefore optimal value of engine exhaust backpressure for the embodiment of FIG. 16 would be in the 2-5 bar range to balance reduction in compression work with reduction in engine reformer breathing and performance.

Example 21

Figure 18:
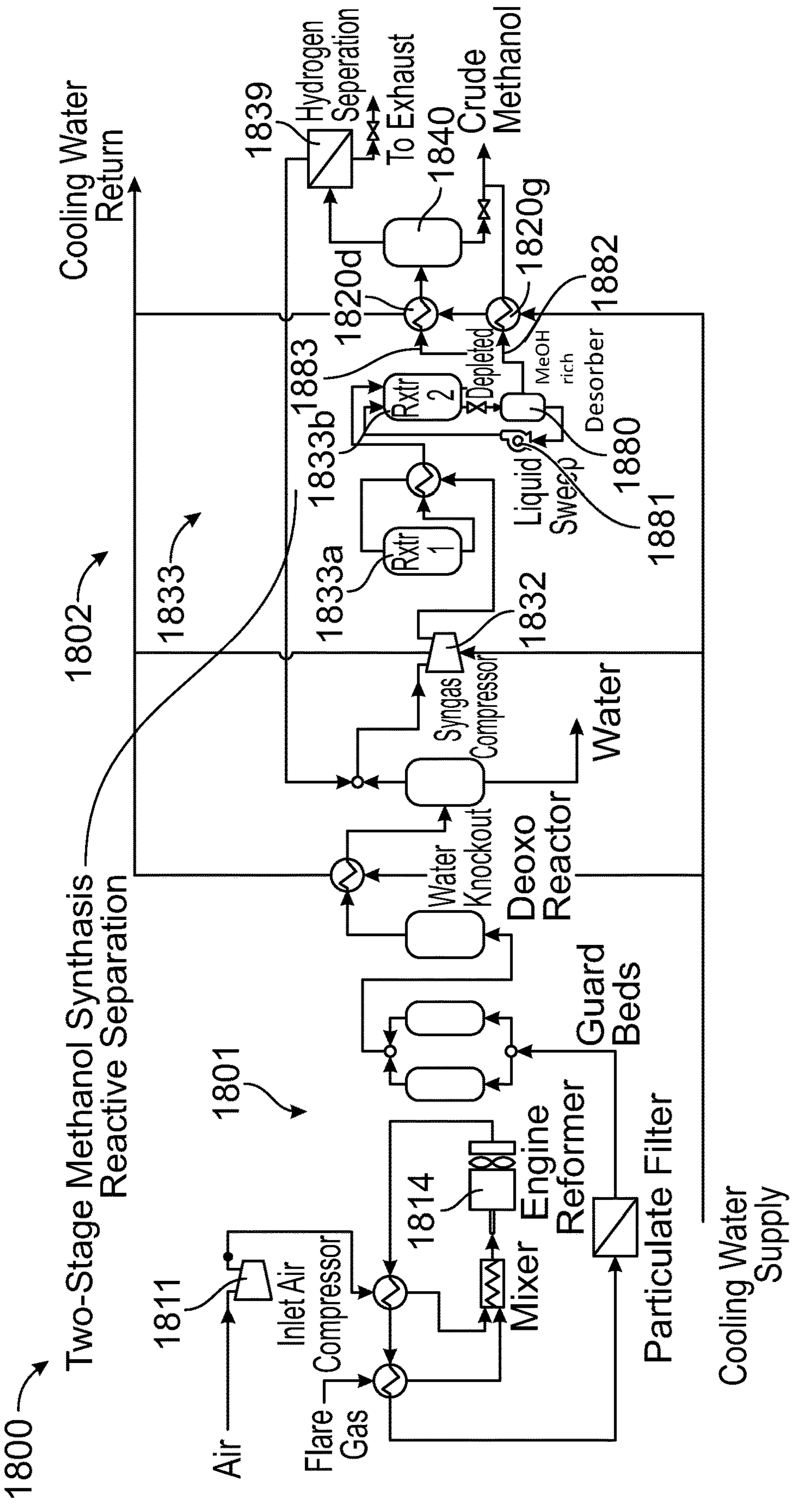
FIG. 18 is a schematic flow diagram of an embodiment of a system and process in accordance with the present inventions.

Turning to FIG. 18 there is shown an embodiment of a system and method for the conversion of flare gas into a value-added product, e.g., methanol. The system 1800 is configured to reduce the compression work required by raising the back pressure of the engine above ambient, to about 5 bar.

The system 1800 has a reformer stage 1801 and a synthesis stage 1802. The system 1800 has an air intake, that feeds air through into a compressor 1811, which compresses the air. The compressed air is fed through heat exchanger in to a mixer. The system has a flare gas intake. The flare gas flows through a heat exchanger **1820*b* into the mixer 1813. The mixer 1813, provides a predetermined mix of air and waste gas, as taught and disclosed in this specification, to a reformer 1814**, which is a reciprocating engine.

The fuel-air mixture that is formed in mixer is preferably rich, more preferably having an overall fuel/air equivalence ratio (ϕ or ER) greater than 1, greater than 1.5, greater than 2, greater than 3, from about 1.5 to about 4.0, about 1.1 to about 3.5, about 2 to about 4.5, and about 1.1 to about 3, and greater values.

It being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. “Air-breathing” reformers, and air breathing engines as used herein are understood to also include engines using air modified with the addition of water, oxygen or both.

The reciprocating engine 1814 combusts the predetermined mixture of flare gas and air to form syngas. The syngas flows through heat exchangers and into a filter, e.g., a particulate filter.

After passing through the filter, the syngas flows to a guard bed reactor assembly, having two guard bed reactors. After leaving the guard bed reactor, the syngas flows to a deoxo reactor. The deoxo reactor removes excess oxygen from the reprocessed gas (e.g., syngas).

The system has a cooling system, which uses a cooling fluid, e.g., cooling water, that is flow through cooling lines.

After leaving the deoxo reactor, the syngas flows to heat exchanger. The reprocessed gas (e.g., syngas) then flows from the heat exchanger to a water removal unit, e.g., a water knockout drum, demister, dryer, membrane, cyclone, desiccant or similar, where water is removed from the syngas. In general, the syngas upon leaving unit the water removal unit should have less than about 5% water by weight, less than about 2%, less than about 1% and less than about 0.1% water.

After leaving the water removal unit, the now dry syngas is in the synthesis stage 1802. In stage 1802 the now dry syngas flows to an assembly that provides for the controlled addition of hydrogen from line into the now dry syngas. In this manner the ratio of the syngas components can be adjusted and controlled to a predetermined ratio. The hydrogen is provided from hydrogen separate 1839. The ratio adjusted dry syngas leaves the assembly and flows to compressor 1832. Compressor 1832 compresses the syngas to an optimum pressure as taught and disclosed in this specification, for use the synthesis unit 1833, which is a two-stage unit with a first reactor unit 1833*a* and a second reactor unit 1833*b*. Synthesis unit 1833 also has heat exchanger.

The synthesis unit 1833 converts the ratio adjusted dry syngas into a value-added product, e.g., methanol. The methanol flows into to heat exchanger and then to a collection unit 1840. The collection unit 1840 collects the methanol and flows it through a line for sale, holding, or further processing.

The collection unit 1840 also has a line that flows gas separated from the methanol to tee-connector, where it is sent to hydrogen separate 1839, to a recycle loop or both. Recycle loop has a compressor and a valve to feed the methanol back into the synthesis unit 1833.

Stage 1802 has a line 1883 for taking depleted methanol from unit 1833*b* and sending it through heat exchanger 1820*d*. The stage 1802 has a methanol desorber 1880 that has pump 1881. Line 1882 for desorber 1880 flows methanol rich product to heat exchanger 1820*g*.

In the operation of system 1800 the preferred process uses a two-stage methanol synthesis reactor with reactive separation in the second stage (Rxtr 2) 1833*b* only. The first stage (Rxtr 1) 1833*a* is generally far from equilibrium and does not warrant reactive separation. The example shown in this figure is reactive absorption or membrane separation with a liquid sweep. Methanol is selectively removed from the reactor in situ resulting in a methanol-depleted gaseous stream containing primarily unreacted syngas and a methanol-rich absorbent stream. Compared to other embodiments, the primary recycle loop is not used because of the improved single-pass conversion. The methane-rich absorbent stream passes through a valve to reduce the pressure and desorb the methanol which is then condensed and sent the product stream. The absorbent, now in a regenerated state, is pumped back to the synthesis pressure and recirculated to the reactor. The pumping work for the absorbent is minimal compared to the syngas compressor work because the liquid absorbent is nearly incompressible. The reactor could be a trickle bed or a membrane reactor with the liquid absorbent (sweep) on the permeate side of the membrane. Any methanol that does not partition into the absorbent is condensed out of the gas phase in a downstream separation step and combined with the methanol product stream Example 22

Figure 19:
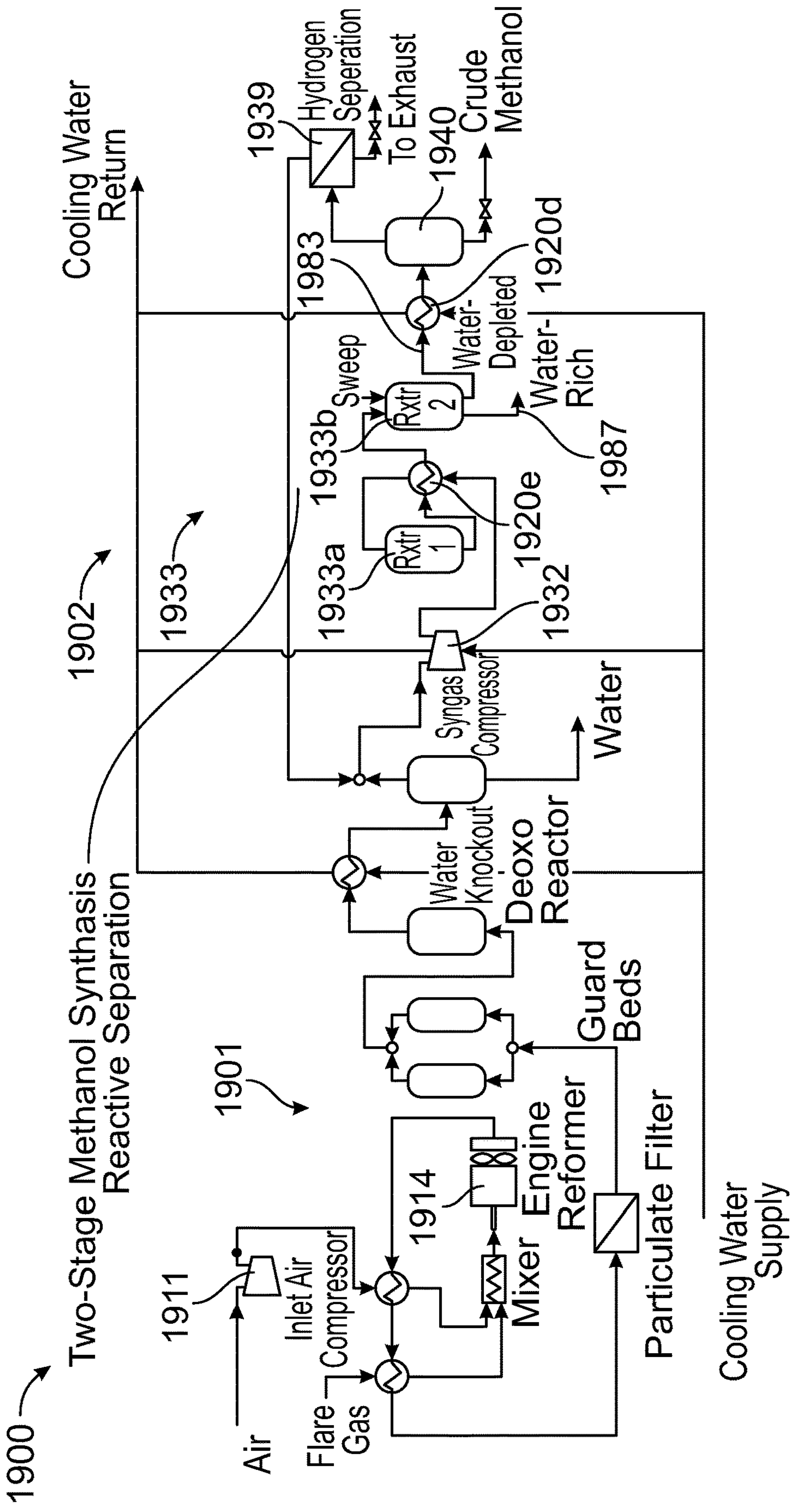
FIG. 19 is a schematic flow diagram of an embodiment of a system and process in accordance with the present inventions.

Turning to FIG. 19 there is shown an embodiment of a system and method for the conversion of flare gas into a value-added product, e.g., methanol. The system 1900 has a reformer stage 1901 and a synthesis stage 1902. The system 1900 has an air intake, that feeds air through into a compressor 1911, which compresses the air. The compressed air is feed through heat exchanger into a mixer. The system has a flare gas intake. The flare gas flows through a heat exchanger 1920*b* into the mixer 1913. The mixer 1913, provides a predetermined mix of air and waste gas, as taught and disclosed in this specification, to a reformer 1914, which is a reciprocating engine.

The fuel-air mixture that is formed in mixer is preferably rich, more preferably having an overall fuel/air equivalence ratio ($\phi$ or ER) greater than 1, greater than 1.5, greater than 2, greater than 3, from about 1.5 to about 4.0, about 1.1 to about 3.5, about 2 to about 4.5, and about 1.1 to about 3, and greater values.

It being understood that oxygen can be added to the air. And that water or steam may also be injected into the mixture of air and fuel, or to air or fuel individually. From about 1 to about 20% (molar) water can be injected, from about 10 to about 15% (molar water), from about 5 to about 17% (molar) water, more than 5% (molar) water, more than 10% (molar) water, more than 15% (molar) water, and less than 25% (molar) water, water can be injected. Following oxygen enrichment, the combustion air can have from about 21% to about 90% oxygen. "Air-breathing" reformers, and air breathing engines as used herein are understood to also include engines using air modified with the addition of water, oxygen or both.

The reciprocating engine 1914 combusts the predetermined mixture of flare gas and air to form syngas. The syngas flows through heat exchangers and into a filter, e.g., a particulate filter.

After passing through the filter, the syngas flows to a guard bed reactor assembly, having two guard bed reactors. After leaving the guard bed reactor, the syngas flows to a deoxo reactor. The deoxo reactor removes excess oxygen from the reprocessed gas (e.g., syngas).

The system has a cooling system, which uses a cooling fluid, e.g., cooling water, that is flow through cooling lines.

After leaving the deoxo reactor, the syngas flows to heat exchanger. The reprocessed gas (e.g., syngas) then flows from the heat exchanger to a water removal unit, e.g., a water knockout drum, demister, dryer, membrane, cyclone, desiccant or similar, where water is removed from the syngas. In general, the syngas upon leaving unit the water removal unit should have less than about 5% water by weight, less than about 2%, less than about 1% and less than about 0.1% water.

After leaving the water removal unit, the now dry syngas is in the synthesis stage 1902. In stage 1902 the now dry syngas flows to an assembly that provides for the controlled addition of hydrogen from line into the now dry syngas. In this manner the ratio of the syngas components can be adjusted and controlled to a predetermined ratio. The hydrogen is provided from hydrogen separate 1939. The ratio adjusted dry syngas leaves the assembly and flows to compressor 1932. Compressor 1932 compresses the syngas to an optimum pressure as taught and disclosed in this specification, for use the synthesis unit 1933, which is a two-stage unit with a first reactor unit 1933*a* and a second reactor unit 1933*b*. Synthesis unit 1933 also has heat exchanger 1920*e*.

The synthesis unit 1933 converts the ratio adjusted dry syngas into a value-added product, e.g., methanol. The methanol flows into to heat exchanger and then to a collection unit 1940. The collection unit 1940 collects the methanol and flows it through a line for sale, holding, or further processing.

The collection unit 1940 also has a line that flows gas separated from the methanol to tee-connector, where it is sent to hydrogen separate 1939, to a recycle loop or both.

Recycle loop has a compressor and a valve to feed the methanol back into the synthesis unit 1933.

Stage 1902 has a line 1983 for taking water depleted methanol from unit 1933*b* and sending it through heat exchanger 1920*d*. The stage 1902 has a line 1987 from unit 1833*b* that removes water rich product.

The system 1900 is for the gas-to-liquids process with reactive separation of byproducts. The process uses a two-stage methanol synthesis reactor with reactive separation in the second stage (Rxtr 2) 1933*b* only. The first stage (Rxtr 1) 1833*a* is generally far from equilibrium and does not warrant reactive separation. The example shown in this figure is membrane separation with a gaseous sweep. Water (a byproduct of $CO_2$ hydrogenation to methanol) is selectively removed from the reactor 1833*b* (via line 1987) in situ resulting in a water-depleted gaseous stream containing primarily unreacted syngas and a water-rich sweep gas. In this embodiment a primary recycle loop is not use because of the improved single-pass conversion. Further, in this embodiment, regeneration of the sweep stream (e.g., air in this embodiment) is not performed. The membrane reactor could use a polymeric or ceramic membrane material that is perm-selective to water and a sweep gas (e.g., air) on the permeate side of the membrane. Removing the water shifts the equilibrium towards the products. The reverse water-gas shift reaction converts $CO_2$ to CO, and so this approach also helps convert $CO_2$ to more reactive CO. As such, this approach is especially attractive for $CO_2$-rich syngas streams such as those produced from partial oxidation. Methanol is condensed out of the gas phase in a downstream separation step and combined with the methanol product stream.

Example 23

An embodiment of a methanol synthesis unit, for use with any of the present systems including the systems of the Examples, is a quench style methanol reactor. A cool reactor feed gas is injected between catalyst beds to quench the gas exiting each catalyst bed and control the feed temperature of reactants to each catalyst bed. The following parameters set the basis for the sizing of the Methanol Reactor.

4 catalyst beds.

225° C. inlet temperature to each bed, consistent with expected catalyst supplier end of life feed temperature. This sets the required quench gas flowrates.

Average gas velocity within the reactor<=1 ft/s. This parameter sets the minimum required reactor diameter.

Average gas residence time per catalyst bed>=2.5 seconds. This parameter sets the minimum average catalyst bed depth, which in turns sets the minimum tangent-to-tangent length of the reactor.

A parameter for methanol synthesis is the ratio of hydrogen to carbon oxides in the feed to the methanol reactor. The gas stoichiometry is defined using the S ratio as follows.

$$S = \frac{\mathrm{H2} - \mathrm{CO2}}{\mathrm{CO} + \mathrm{CO2}}$$

The preferred S ratio is between 2-2.3. Typical steam methane reformers produce a syngas with an S ratio of approximately 3. However, the engine reformers of the present systems can produce a syngas with an S ratio closer to 1. The target S ratio, for the embodiment of this Example, is 2.1. To achieve this S ratio at the feed to the methanol reactor it is required that a portion of the recycled loop gas is sent through a hydrogen purification step. Therefore, the target S ratio defines the sizing basis for the Hydrogen Recovery Package.

Example 23

An embodiment of a control system for the operation and monitoring of the present systems and processes, including the Examples. This control system also has components for calculation, obtaining and storing data and information about the operation of the system and process, e.g. process information and data. This process data and information can, among other things, include: mass balance data and information (e.g., kg of flare gas into system, kg of methanel produced, kg of exhaust produced, etc.), carbon capture data and information, $CO_2$e related data and information, and combinations and variations thereof and well as other types of data and information. This data and information among other things can be used to validate or obtain carbon credits on for example a carbon exchange, or to meet environmental regulatory reporting or monitoring requirements.

A control has a control panel located on site at the system (e.g., on a skid, on one or both stages in a modular system). The control panel will house control equipment such as controllers, marshaling panels, power supplies, network switches, etc. The control panel will include the basic process control and the safety shutdown system. Preferably all information will be available for monitoring and control from the control panel.

The process information and data on the on-site control panel will preferably be available for remote monitoring and limited remote control from a remote-control room via cellular (4G/5G) network, satellite, or other hardwired or wireless communication mode.

Preferably, the level of automation provided by the control panel shall be such that under normal plant operating conditions, manual intervention of the operators is minimized. Manual intervention can be required for abnormal events and conditions that occur during module start up and shutdown. Preferably the control panel shall always be active and provide full control, monitoring, and safeguarding of the module at all times.

Preferably, the control systems shall be designed to be fail-safe such that upon the loss of power, instrument air supply, or control signal to/from instrument device shall cause the plant to move to a predetermined safe operating state.

Preferably, the control systems shall support a level of redundancy and fault tolerance such that the failure of any single component of the system shall have no significant adverse effect on the processes being controlled.

Preferably, the control panel serves as the Integrated Control & Safety System (ICSS) and thus provides basic process control and basic safety functions for the system, and preferably includes one, more than one and all of the following functions:

Basic Process Control System (BPCS),

Safety Instrumented System (SIS), if determined required in future phases of the project, Corresponding Human-Machine Interfaces (HMI) displays, Communications systems, Mechanical vendor system interfaces (such as Anti-Surge Control systems (ASC)).

Preferably, all field instruments shall be "smart" type device in which, for example, the HART protocol is available for instrument diagnostic. Instrument designs and selections shall follow industrial standards such as ISA (International Society of Automation) and PIP (Process Industry Practices). IEC61508 certified instruments shall be used for SIFs that are SIL 1 or above.

Example 24

Figure 24:
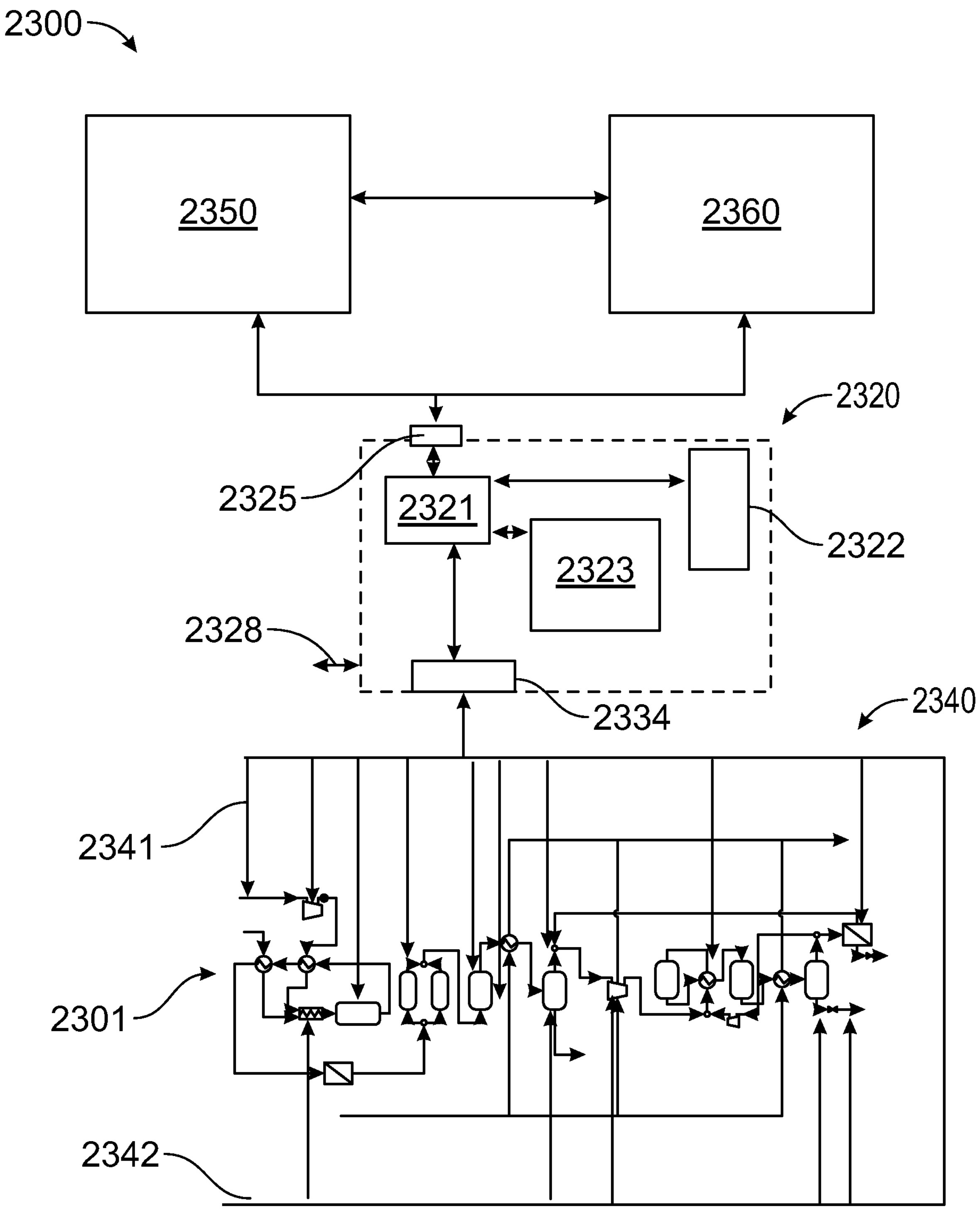
FIG. 24 is a schematic diagram of an embodiment of a control system for use with embodiments of the present systems and methods in accordance with the present inventions.

Turning to FIG. 24 there is provided a control and communication system network 2300 for the use with the present systems and processes, including the Examples. Network 2300 includes and is control communication with a flare gas to syngas to methanol system 2301, generally of the type disclosed and taught in the specification, including the Examples.

The system 2300 has a local, e.g., on-site control system 2320. The components of the on-site control system 2320 can be in a box or housing located on or attached to the system 2301. The components of system 2320 may be located in separate housings and enclosures or in a single enclosure. The system 2320 has a controller 2321, having a processor and memory, a storage device 2322, a HMI (human machine interface) 2323, and an input/output (I/O) 2324, and a communication module 2325.

The system 2300 has numerous on-site communication pathways, e.g., 2341 that make up local, or on-site sub-network 2340. The Sub-network 2340 can also communicate with other sub-networks via pathway 2342. These on-site communication pathways. e.g. 2341, transmit communications, including control communication, data and information, to and from one, more than one, and preferably all the devices and components of the system 2301. Additionally, these on-site-pathways, e.g., 2341, transmit communications, including control communications, data and information, to and from one, more than one, and preferably all of the sensors and monitoring devices and instruments in system 2301. In this manner on-site sub-network 2340 can send and receive control communications, as well as, sensor data and information from system 2301 to the control system 2320. In this manner the on-site control system 2320 is in control communications with the flare gas to syngas to methanol system 2301. In this manner the on-site control system 2320 can operation and control the system 2301, and receive data and information about the processes and operations of the system 2301. The on-site control system 2320 can be, for example, configured along the lines of the control system in Example 23.

The on-site control system is in control communication with a remote-control system 2350. In this manner, the remote-control system 2350 can configure, control, change, monitor the on-site control system 2320, the system 2300, and both. The remote-control system has The system 2320 has a controller, having a processor and memory, a storage device, a HMI, and a communication module.

The remote-control system 2350, the control system 2320 and both are configured to monitor, calculate, record, store and transmit, information about any and all aspects of the operation of system 2301, e.g., flow rates, mass flow, density, temperature, settings of equipment, exhaust conditions, etc. Among of things, these operation aspects would include: mass balance data and information (e.g., kg of flare gas into system, kg of methanal produced, kg of exhaust produced, etc.). This information and data can be and processed to determine and record, preferably real time, GWP information and data, carbon capture information and data, CO2e information and data, for the operation of system 2301, and preferably for the real time operation of system 2301. This data and information among other things can be used to validate or obtain carbon credits on for example a carbon exchange, or to meet environmental regulatory reporting or monitoring requirements. Preferably this GWP type information is encrypted using block chain, or some other encryption methodology, to insure its validity.

Thus, the control system 2320, the remote-control system 2350 and both can be in control communication with another entity 2360. For example, entity 2360 can be a carbon exchange, it can be a government regulatory agency, it can be a trade regulatory agency, or other entities, such as a class room. It should be noted that while the communications pathways between entity 2360 and the control can be two-way communication, these pathways do not send or receive any control communication. In this manner the entity 2360 has no capability to control the system 2301. Further, the other information about system 2301 can be provided to entity 2360, as may be needed or required.

Example 25

Figure 25:
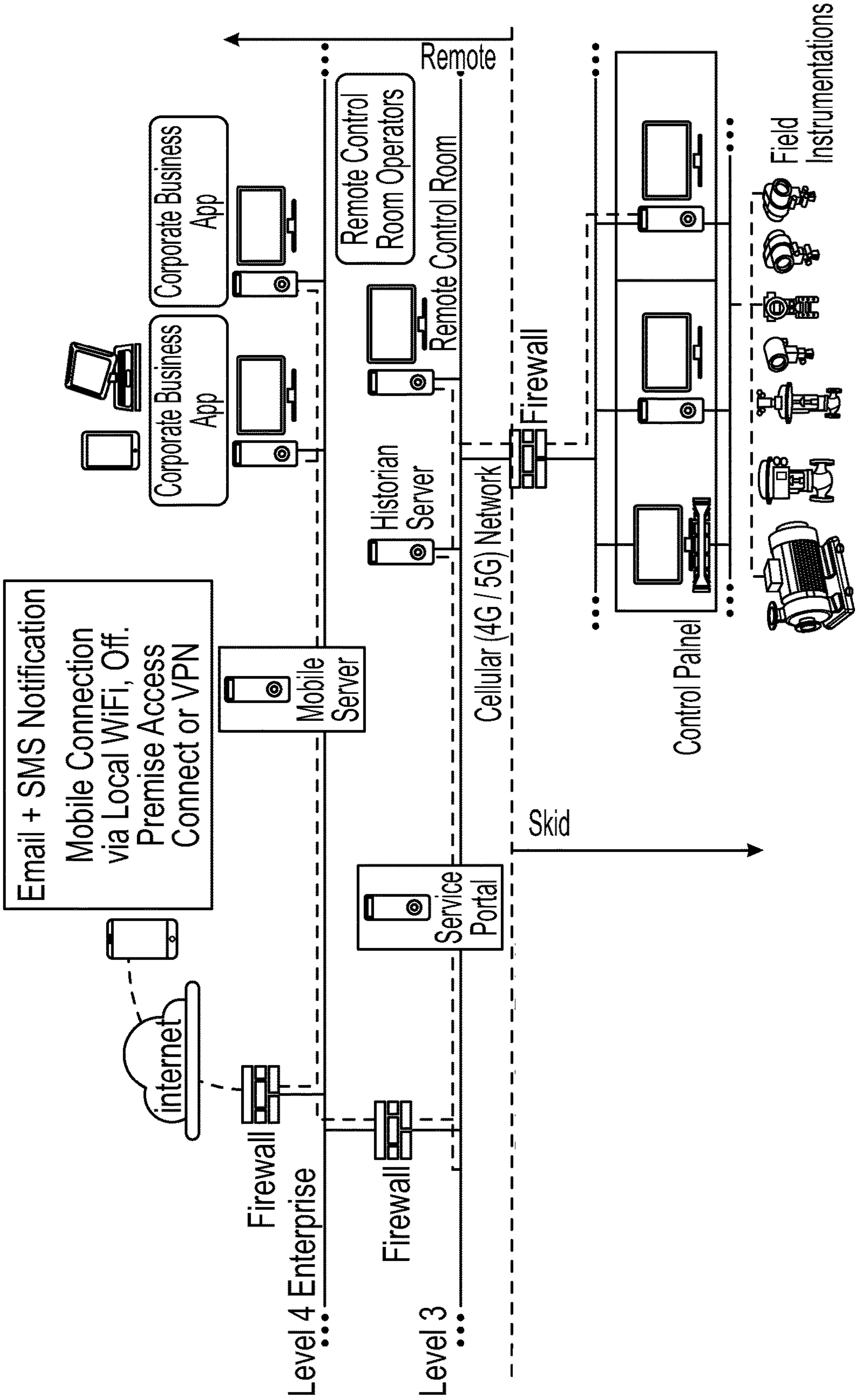
FIG. 25 is a detailed schematic diagram of an embodiment of a control system for use with embodiments of the present systems and methods in accordance with the present inventions.

Turning to FIG. 25 there is shown a schematic of the architecture of a control communication network for use with the present systems and processes, including the Examples.

Example 26

In situations where the flare gas contains $H_2S$, is preferably is removed prior to processing the flare gas into syngas. Batch And cyclic process technology can be used to remove the $H_2S$, which would include a packed bed with solid adsorbent/scavenger material. Liquid solvents can be used, most commonly an amine like methyl diethanolamine (MDEA) to remove the $H_2S$ and $CO_2$ from flare gas streams. A typical configuration is to flow the amine solution through an absorption tower countercurrent to the flare gas. The amine stays in a closed loop and is regenerated with heat.

Example 27

The present systems and processes, including the Examples are operated to convert flare gas into methanol having a purity of about 80% and greater, at least about 85%, at least about 90%, at least about 93%, at least 95%, from about 80% to 95%, and from about 85% to about 90%.

Example 28

A system and process to convert otherwise uneconomic hydrocarbon-based fuel such as flare gas to value-added, easily transported products (such as methanol, ethanol, ammonia, dimethyl-ether, F-T liquids, and other fuels or chemicals) using an autonomous, modular system comprising the following elements: (1) a fuel conditioning system to meet requirements of downstream components; (2) an air-breathing gas turbine, modified to operate a rich, partial-oxidation reformer, to produce a syngas mixture with a $H_2/CO$ ratio suitable for synthesis of liquids; (3) a combination of integrated heat exchangers, compression system components, and heat exchangers to prepare the syngas for the downstream synthesis reactors; and (4) a downstream synthesis reactor system to produce useful liquid hydrocarbon products.

Example 29

A system and process to convert otherwise uneconomic hydrocarbon-based fuel such as flare gas to value-added, easily transported products (such as methanol, ethanol, ammonia, dimethyl-ether, F-T liquids, and other fuels or chemicals) using an autonomous, modular system comprising the following elements: (1) a fuel conditioning system to meet requirements of downstream components; (2) an air-breathing gas turbine, modified to operate a rich, partial-oxidation reformer, to produce a syngas mixture with a H2/CO ratio suitable for synthesis of liquids; (3) a combination of integrated heat exchangers, compression system components, and heat exchangers to prepare the syngas for the downstream synthesis reactors; (4) a downstream synthesis reactor system to produce useful liquid hydrocarbon products; and, (5) a hydrogen recycle loop to improve overall system process performance.

Example 30

The systems and process of Examples 28 and 29, can also have one, or more, or all of the following additional features: (6) optional substantially oxygen-free gas recirculation loop to cool and protect downstream components of the combustor, such as seals, bearings, and secondary cavities; (7) optional $O_2$ enrichment of the inlet stream to the gas turbine via membrane separation or partial air separation unit; (8) a recuperator heat exchanger (from (3)) and a turbo expander to recover energy from the high pressure exhaust gas from the downstream synthesis reactor; (9) integration of a closed-loop operating system with custom instrumentation; (10) a cloud-based remote monitoring system, including AI-trained anomaly detection for dynamic preventative maintenance and operations control; (11) optional offtake pathways to utilize byproducts, such as nitrogen, water, and $CO_2$ for reinjection, well recompletions, or other purposes; (12) optional water (or steam) injection into the rich combustor to improve $H_2$/CO ratio and reduce carbon build-up on surfaces within the combustor and turbine.

Example 31

Embodiments of these inventions, provide modular systems that can be positioned near sources of uneconomical hydrocarbons (e.g., flare gas), syngas, product gas, and reprocessed gas to convert these materials into higher value products. These inventions will be used to take uneconomic hydrocarbon-based fuels at a well-head (e.g, flare gas) and remote locations that are primarily gaseous hydrocarbons and convert them to a more valuable easily condensable or liquid compounds, such as methanol. One source of source fuel could be associated gas or flare gas, which is produced as a byproduct at oil wells. Another source could be biogas from landfill or anaerobic digesters.

A small-scale plant, targeting 3,000,000 scfd (standard cubic feet per day) of inlet gas. The size of such a plant could vary from 300,000 scfd to 15,000,000 scfd. The plant is incorporated into one or more modular, interconnected skids or containers that are built at a central fabricator shop location and then installed at a field location. A small number of modules comprise the system and when connected at site they form an integrated system. The modular nature of the assembly enables application to remote locations under a range of inlet gas feed volumes, with a minimum of field labor. The modular nature further improves flexibility to deploy or redeploy these assets, reduces initial capital outlay and project financial risks, allows matching of the process throughput to the flare gas supply, and reduces time-to-market by allowing module fabrication and site preparation to occur in parallel.

Example 32

A modular unit having a collection of unit-scale engine reformers and unit-scale MeOH synthesis systems, with no common BOP (balance of plant).

Example 33

A modular unit having a collection of unit-scale engine reformers and unit-scale MeOH synthesis systems, with common BOP.

Example 34

A modular unit having a collection of unit-scale engine reformers that supply a common, unitary MeOH synthesis system.

Example 35

A modular unit having 900 scfd (standard cubic feet per day) of feed gas, (e.g., flare gas).

Example 36

A modular unit having 75,000 scfd of feed gas (e.g., flare gas), scale right-sized for a single engine reformer.

Example 37

A modular reformer stage having 2 or more, 3 or more, at least 5, at least 6, or 2 to 10 reformers. The reformers can be one or more of a gas turbine engine, a combustion box, an internal combustion engine, an otto cycle reciprocating engine, a diesel cycle reciprocating engine and combinations of these. This modular reformer stage can be skid mounted, truck mounted, etc.

Example 38

In an embodiment of the present inventions have a rich-burn reciprocating engine and a synthesis reactor. Unlike a traditional reciprocating engine, the engine runs at rich conditions, up to equivalence ratio of 2.5, so the fuel experiences rich partial oxidation (POX). Additional components include the fuel conditioning system, heat exchangers, compressors, and turbines. The fuel conditioning system separates liquids from gases in the feed stream and removes compounds that can damage the reciprocating engine or synthesis reactor. The heat exchangers and compressors take the syngas mixture at the exit of the reciprocating engine and adjust the temperature and pressure to deliver the target conditions for the synthesis reactor. Within the synthesis sub-system is an optional $H_2$ recycle loop. The gas at the exit of the synthesis reactor is heated in a recuperating (e.g., counter-flow) heat exchanger to an elevated temperature and then expanded to ambient conditions.

Example 39

In this embodiment it is preferable that in configuring and operating a syngas engine for achieving preferred engine operation under conditions sufficiently rich to produce a syngas with the desired H2/CO ratio near 2. Even if acceptable operability is achieved with one fixed fuel composition, changes to the fuel composition, which will arise during operation in the field, for example at an oil well, will change the combustion properties and lead to poor engine operation. Thus, the engine has sensors and control systems that detect changes in the combustion properties of the fuel and adapt its parameters to achieve desired engine operation. An engine with a combination of sensing and variable compression ratio can overcome these challenges. A variable compression ratio engine adjusts the compression ratio of an internal combustion engine while the engine is in operation. Variable compression engines allow the volume above the piston at top dead center to be changed.

Example 40

An embodiment of a variable compression ratio engine reformer is through the use of variable valve timing, such as cam phasers. Twin Independent Variable Camshaft Timing (Ti-VCT) is the name given by Ford to engines with the ability to advance or retard the timing of both the intake and exhaust camshafts independently, unlike the original versions of VCT, which only operated on a single camshaft. This allows for improved power and torque, particularly at lower engine RPM, as well as improved fuel economy and reduced emissions A "cam phaser" is an adjustable camshaft sprocket that can be turned by means of a computer-controlled servo. Rather than operating with a fixed amount of advance or retard, the computer can advance or retard the cam or cams continuously. An embodiment of this application is to enhance drivability at light load and low engine speed (by reducing overlap of the intake and exhaust events to minimize residual dilution), and generate more power at high engine speed (by retarding the intake valve event to increase volumetric efficiency).

For rich combustion operation to produce syngas, when the fuel composition is richer (greater fraction of low-octane constituents) the purpose of retarding the timing of the intake valve event is to retard valve closing sufficiently to shorten the effective compression stroke and thus reduce the effective compression ratio.

When the fuel composition is leaner (greater fraction of high-octane constituents) the purpose of advancing the timing of the intake valves is to advance intake valve opening sufficiently to extend the effective compression strokes and thus increase the effective compression ratio. Operating at a higher effective compression ratio increases pressure and temperature in the combustion chamber and thus extends the rich combustion limit with lean gas.

Example 41

An VVT/cam (variable valve timing/cam) phaser engine that allows, among other things, the compression ratio to be varied according the properties of the incoming fuel for rich combustion to produce syngas.

Example 42

A VVT/cam phaser engine with sensors to detect the in-cylinder combustion behavior under rich conditions and automatically adjust the compression.

This approach can be applied to a two-stroke or four-stroke reciprocating engine.

Example 43

A system and process to convert otherwise uneconomic hydrocarbon-based fuel such as flare gas to value-added, easily transported products (such as methanol, ethanol, ammonia, dimethyl-ether, F-T liquids, and other fuels or chemicals) using an autonomous, modular system comprising the following elements: (1) a fuel conditioning system to meet requirements of downstream components; (2) an air-breathing gas engine, modified to operate a rich, partial-oxidation reformer, to produce a syngas mixture with a H2/CO ratio suitable for synthesis of liquids; (3) a combination of integrated heat exchangers, compression system components, and heat exchangers to prepare the syngas for the downstream synthesis reactors; (4) a downstream synthesis reactor system to produce useful liquid hydrocarbon products; and, (5) a hydrogen recycle loop to improve overall system process performance.

Example 44

A embodiment of a variable compression ratio engine is through an opposed-piston free-piston linear internal combustion engine. A free-piston engine is linear, 'crankless' internal combustion engine. The power delivered by the engine is not delivered via a crankshaft, but instead through exhaust gases driving a turbine or a linear motor/generator directly coupled to the pistons to produce electric power.

Example 45

A rich-burn reciprocating engine and a synthesis reactor. Unlike a traditional reciprocating engine, the engine runs at fuel-rich conditions, up to equivalence ratio of 2.5 so the fuel experiences rich partial oxidation (POX). Additional components include the fuel conditioning system, heat exchangers, compressors, and synthesis reactor. The fuel conditioning system separates liquids from gases in the feed stream and removes compounds that can damage the reciprocating engine or synthesis reactor. The heat exchangers and compressors take the syngas mixture at the exit of the reciprocating engine and adjust the temperature and pressure to deliver the target conditions for the synthesis reactor. Within the synthesis sub-system is an $H_2$ recycle loop or $CO_2$ scrubber for syngas ratio adjustment. Optionally, the gas at the exit of the synthesis processes is heated in a recuperating (e.g., counter-flow) heat exchanger to an elevated temperature and then expanded to ambient pressure, thus providing shaft work for compression of the synthesis gas.

Example 46

The embodiments of the systems of the above Examples are operated in a carbon neutral-to-negative manner, producing and releasing less than or equal to zero $CO_2$e from a lifecycle perspective.

Example 47

One or more of the systems of the above Examples are placed at an oil field having a large number of oil wells. The flare gas from these oil wells is captured at the wellhead of each of the oil wells and flows in a piping and manifold system to the units where it is processed into an end product, such as methanol.

Example 48

One or more of the systems of the above Examples are placed at a livestock production farm, handling or production facility. The methane-rich biogas from anaerobic digestion of the livestock manure is collected and processed by the systems into an end product, such as methanol.

Example 49

One or more of the systems of the above Examples are placed at municipal waste-water treatment facilities where anaerobic digesters produce fuel for the syngas unit, and methanol produced by the process is consumed by the denitrification process as part of the treatment process. This approach results in a local and circular process for waste water treatment.

Example 50

In an oil filed have several oil, gas or both wells, (e.g., 5 wells, 10 wells, 20 wells or more) piping and distribution headers are used to collect and transfer the flare gas from each of the wells, to one or of the present waste gas, e.g., flare gas, processing units, such as one or more of systems of the above Examples.

Example 51

Hydrocarbon production activity, e.g., exploration, drilling, workover and completion of a hydrocarbon well, e.g., an oil or gas well, can including the planning for, and use of, the present systems and methods, including the systems of the above Examples. In this manner the overall effect of the hydrocarbon production activity on global warming, e.g., GWP, can be mitigated or reduced. Thus, the use of the present systems and methods, including the Examples, can be included in the planning hydrocarbon activity, as well as, in the obtaining of regulatory approval for such activity.

Example 52

The present systems and methods, including the systems and methods of the Examples, where the source of the flare gas is one, or more than one, of a hydrocarbon well, an oil well, an unconventional oil well, a conventional oil well, an off-shore well, or an on-shore well.

Example 53

The present systems and methods, including the systems and methods of the Examples, where the source of the flare gas is selected from the group consisting of petrochemical processing, refining, landfills, waste water treatment, and livestock.

Example 54

The embodiments of the systems of the above Examples are operated in an energy positive manner, producing more power, in the form of electricity, than is required to operate the system.

Headings and Embodiments

It should be understood that the use of headings in this specification is for the purpose of clarity, reference, and is not limiting in any way. Thus, the processes compositions, and disclosures described under a heading should be read in context with the entirely of this specification, including the various Examples. The use of headings in this specification should not limit the scope of protection afforded the present inventions.

It is noted that there is no requirement to provide or address the theory underlying the novel and groundbreaking production rates, performance or other beneficial features and properties that are the subject of, or associated with, embodiments of the present inventions. Nevertheless, various theories are provided in this specification to further advance the art in this important area, and in particular in the important area of hydrocarbon exploration and production. These theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the conductivities, fractures, drainages, resource production, and function-features of embodiments of the methods, articles, materials, devices and system of the present inventions; and such later developed theories shall not limit the scope of protection afforded the present inventions.

The various embodiments of devices, systems, activities, methods and operations set forth in this specification may be used with, in or by, various processes, industries and operations, in addition to those embodiments of the Figures and disclosed in this specification. The various embodiments of devices, systems, methods, activities, and operations set forth in this specification may be used with: other processes industries and operations that may be developed in the future: with existing processes industries and operations, which may be modified, in-part, based on the teachings of this specification; and with other types of gas recovery systems and methods. Further, the various embodiments of devices, systems, activities, methods and operations set forth in this specification may be used with each other in different and various combinations. Thus, for example, the configurations provided in the various embodiments of this specification may be used with each other. For example, the components of an embodiment having A, A' and B and the components of an embodiment having A", C and D can be used with each other in various combination, e.g., A, C, D, and A. A" C and D, etc., in accordance with the teaching of this specification. Thus, the scope of protection afforded the present inventions should not be limited to a particular embodiment, configuration or arrangement that is set forth in a particular embodiment, example, or in an embodiment in a particular Figure.

The invention may be embodied in other forms than those specifically disclosed herein without departing from its spirit or essential characteristics. The described embodiments are to be considered in all respects only as illustrative and not restrictive.

What is claimed:

1. A carbon-neutral method of converting a flare gas to an end product, the method comprises:

a. receiving a flow of a flare gas from a source;

b. compressing the flare gas;

c. partially oxidizing the flare gas to provide a reprocessed gas;

wherein the partial oxidation of the flare gas is conducted at a specific entropy of greater than about 7.1 KJ/kg° C., wherein a reference state for the specific entropy is based upon 25° C. and 1 atmosphere; and, d. converting the reprocessed gas into an end product;

e. wherein steps a to d produce less than 2.0 kg of $CO_2$ per kg of flare gas received.

2. The method of claim 1, wherein the step of partially oxidizing the flare gas, comprises combusting a mixture of the flare gas and a source of oxygen.

3. The method of claim 2, wherein the oxygen source comprises air, and the mixture has a fuel/air equivalence ratio of greater than 1.

4. The method of claim 2, wherein the oxygen source comprises air, and the mixture has a fuel/air equivalence ratio of from 1.1 to about 4.

5. The method of claim 2, wherein the oxygen source comprises air, and the mixture has a fuel/air equivalence ratio of from about 1.5 to about 3.0.

6. The method of claim 5, wherein the specific entropy is about 7.1 KJ/kg° C. to about 8.6 KJ/kg° C.

7. The method of claim 1, further comprising one or more of: (a) using, water, steam, or both in the step of partially oxidizing the flare gas; and (b) wherein the step of partially oxidizing the flare gas occurs in an air-breathing reformer.

8. The method of claim 1, wherein the step of partially oxidizing the flare gas takes place in a reformer stage of a liquid-to-gas system; and wherein, the reformer stage comprises one or more of a gas turbine engine, a combustion box, and a reciprocating engine.

9. The method of claim 8, wherein the specific entropy is about 7.1 KJ/kg° C. to about 8.6 KJ/kg° C.

10. The method of claim 1, wherein the step of converting the reprocessed gas into an end product takes place under a predetermined synthesis temperature and a predetermined synthesis pressure.

11. The method of claim 10, further comprising one or more of: (a) wherein the predetermined synthesis temperature is from about 200° C. to about 300° C.; and (b) wherein the predetermined synthesis pressure is from about 30 bar to about 100 bar.

12. The method of claim 10, wherein the specific entropy is about 7.1 KJ/kg° C. to about 8.6 KJ/kg° C.

13. The method of claim 10, wherein the step of partially oxidizing the flare gas takes place under a predetermined reformer temperature and a predetermined reformer pressure; and further comprising one or more of: (a) wherein the predetermined reformer temperature is from about 700° C. to about 1,200° C.; and (b) wherein the predetermined reformer pressure is from about 1 bar to about 70 bar.

14. The method of claim 13, wherein the step of converting the reprocessed gas into an end product takes place under a predetermined synthesis temperature and a predetermined synthesis pressure; and the predetermined synthesis temperature is from about 200° C. to about 300° C. and the predetermined synthesis pressure is from about 30 bar to about 100 bar.

15. The method of claim 13, wherein the specific entropy is about 7.1 KJ/kg° C. to about 8.6 KJ/kg° C.

16. The method of claim 1, comprising one or more of: (a) the step of removing oxygen from the reprocessed gas; (b) the step of removing any excess oxygen from the reprocessed gas; (c) wherein the reprocessed gas comprises a synthesis gas; and (d) wherein a variation in a composition of the flare gas does not change a composition of the end product.

17. The method of claim 1, wherein the step of converting the reprocessed gas into an end product takes place under a predetermined synthesis temperature and a predetermined synthesis pressure; wherein the step of partially oxidizing the flare takes place under a predetermined reformer temperature and a predetermined reformer pressure; wherein a variation in a composition of the flare gas does not change a composition of the end product; and wherein the variation in the composition of the flare gas does not require a change in one or more than one, of the predetermined synthesis temperature and the predetermined synthesis pressure.

18. The method of claim 17, wherein the specific entropy is about 7.1 KJ/kg° C. to about 8.6 KJ/kg° C.

19. The method of claim 1, wherein less than 1.0 kg of $CO_2$ per kg of flare gas is produced.

20. The method of claim 19, wherein the specific entropy is about 7.1 KJ/kg° C. to about 8.6 KJ/kg° C.

21. The method of claim 1, wherein less than 0.5 kg of $CO_2$ per kg of flare gas is produced.

22. The method of claim 1, wherein the reprocessed gas comprises a syngas.

23. The method of claim 1, wherein the reprocessed gas consists essentially of a syngas.

24. The method of claim 1, wherein the end product is a liquid.

25. The method of claim 1, wherein the end product comprises a compound selected from the group consisting of methanol, ethanol, mixed alcohols, ammonia, dimethyl-ether, and F-T liquids.

26. The method of claim 25, wherein the specific entropy is about 7.1 KJ/kg° C. to about 8.6 KJ/kg° C.

27. The method of claim 1, wherein steps a) to d) are net carbon-negative, whereby these steps produce less than about −40 kg CO2e per kg of end product produced.

28. The method of claim 27, wherein the specific entropy is about 7.1 KJ/kg° C. to about 8.6 KJ/kg° C.

29. The method of claim 1, wherein steps a) to d) are net carbon-negative, whereby these steps produce from about −20 kg CO2e to about −150 kg CO2e, per kg of end product produced, wherein the end product comprises methanol.

30. The method of claim 1, wherein the source of the flare gas is selected from the group consisting of petrochemical processing, refining, landfills, waste water treatment, livestock and combinations of one or more of these.

31. The method of claim 1, wherein the specific entropy is greater than about 7.5 KJ/kg° C.

32. The method of claim 1, wherein the specific entropy about 7.1 KJ/kg° C. to about 8.6 KJ/kg° C.

33. A carbon-neutral method of making an end product, the method comprises:

a. partially oxidizing a flare gas to provide a reprocessed gas; wherein the partial oxidation of the flare gas is conducted at a specific entropy of about 7.1 KJ/kg° C. to about 8.6 KJ/kg° C., wherein a reference state for the specific entropy is based upon −273.15° C. and 1 atmosphere;
b. converting the reprocessed gas into an end product;
c. wherein steps a) to b) produce less than 2.0 kg of $CO_2$ per kg of flare gas partially oxidized; and,
d. wherein steps a) to b) are net carbon-negative, whereby these steps produce less than about −20 kg CO2e per kg of end product produced.

34. The method of claim 33, further comprising one or more of: (a) wherein the reprocessed gas is a syngas; and (b) wherein the end product comprises a compound selected from the group consisting of methanol, ethanol, mixed alcohols, ammonia, dimethyl-ether, and F-T liquids.

35. The method of claim 33, wherein the partial oxidation of step a) is conducted at a predetermined partial oxidation pressure and a predetermined partial oxidation temperature; and the conversion of step b) is conducted at a predetermined synthesis pressure and a predetermined synthesis temperature; wherein the predetermined temperatures and pressures comprises one, more than one, or all of: (i) the predetermined partial oxidation temperature is from about 900° C. to about 1,150° C.; (ii) the predetermined partial oxidation pressure is from about 1 bar to about 70 bar; (iii) the predetermined synthesis temperature is from about 200° C. to about 300° C.; and, (iv) the predetermined synthesis pressure is from about 30 bar to about 100 bar.

36. A carbon-neutral method of making an end product, the method comprises:

a. partially oxidizing a flare gas to provide a reprocessed gas; wherein the partial oxidation of the flare gas is conducted at a specific entropy greater than about 7.5 KJ/kg° C., wherein a reference state for the specific entropy is based upon −273.15° C. and 1 atmosphere;
b. converting the reprocessed gas into an end product;
c. wherein steps a) to b) produce less than 2.0 kg of $CO_2$ per kg of flare gas partially oxidized; and,
d. wherein steps a) to b) are net carbon-negative, whereby these steps produce less than about −20 kg CO2e per kg of end product produced.

* * * * *